(12) United States Patent
Horseman et al.

(10) Patent No.: US 10,475,351 B2
(45) Date of Patent: Nov. 12, 2019

(54) SYSTEMS, COMPUTER MEDIUM AND METHODS FOR MANAGEMENT TRAINING SYSTEMS

(71) Applicant: Saudi Arabian Oil Company, Dhahran (SA)

(72) Inventors: Samantha J. Horseman, Dhahran (SA); Brent Mattson, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 533 days.

(21) Appl. No.: 14/959,244

(22) Filed: Dec. 4, 2015

(65) Prior Publication Data

US 2017/0162072 A1   Jun. 8, 2017

(51) Int. Cl.
*G09B 19/00* (2006.01)
*G09B 9/00* (2006.01)
(Continued)

(52) U.S. Cl.
CPC .............. *G09B 19/00* (2013.01); *A61B 5/002* (2013.01); *A61B 5/02* (2013.01); *A61B 5/0205* (2013.01); *A61B 5/1176* (2013.01); *A61B 5/162* (2013.01); *A61B 5/165* (2013.01); *A61B 5/486* (2013.01); *A61B 5/4884* (2013.01); *A61B 5/681* (2013.01); *A61B 5/6803* (2013.01); *A61B 5/7267* (2013.01); *A61B 5/7278* (2013.01); *A61B 5/746* (2013.01); *A61B 5/7425* (2013.01); *G06Q 10/0639* (2013.01); *G09B 7/02* (2013.01); *G09B 9/00* (2013.01); *A61B 5/01* (2013.01); *A61B 5/021* (2013.01); *A61B 5/024* (2013.01); *A61B 5/0402* (2013.01); *A61B 5/0476* (2013.01); *A61B 5/0488* (2013.01);
(Continued)

(58) Field of Classification Search
CPC ..................................................... G09B 19/00
USPC ......................................................... 434/236
See application file for complete search history.

(56) References Cited

U.S. PATENT DOCUMENTS 4,951,963 A   8/1990   Behr et al.
4,998,534 A   3/1991   Claxton et al.
(Continued)

FOREIGN PATENT DOCUMENTS

AU        767533 B2      11/2003
CN      101065752 A      10/2007
(Continued)

OTHER PUBLICATIONS

"40 Best Companies for Leaders—2014" Chief Executive, available as of Dec. 13, 2015 at the website: http://chiefexecutive.net/40-best-companies-for-leaders-2014/; pp. 1-3.
(Continued)

*Primary Examiner* — Thomas J Hong
(74) *Attorney, Agent, or Firm* — Bracewell LLP; Constance G. Rhebergen; Christopher L. Drymalla

(57) ABSTRACT

A training system, including a plurality of sensors to obtain a plurality of biometrics from a first user. A stress level, a level of interest, a level of engagement, a level of alertness, and a level of excitement are determined responsive to analysis of ones of the plurality of biometrics. An indication is displayed of the obtained biometrics, the determined stress level, and the determined levels of interest, engagement, alertness, and excitement.

20 Claims, 17 Drawing Sheets

(51) Int. Cl.

| | | |
|---|---|---|
| *A61B 5/0205* | (2006.01) | |
| *A61B 5/1171* | (2016.01) | |
| *A61B 5/00* | (2006.01) | |
| *A61B 5/16* | (2006.01) | |
| *A61B 5/02* | (2006.01) | |
| *G06Q 10/06* | (2012.01) | |
| *G09B 7/02* | (2006.01) | |
| *A61B 5/0476* | (2006.01) | |
| *A61B 5/024* | (2006.01) | |
| *A61B 5/08* | (2006.01) | |
| *A61B 5/053* | (2006.01) | |
| *A61B 5/145* | (2006.01) | |
| *A61B 5/021* | (2006.01) | |
| *A61B 5/01* | (2006.01) | |
| *A61B 5/0402* | (2006.01) | |
| *A61B 5/0488* | (2006.01) | |
| *A61B 5/1455* | (2006.01) | |

(52) U.S. Cl.
 CPC ........... *A61B 5/0531* (2013.01); *A61B 5/0816* (2013.01); *A61B 5/14532* (2013.01); *A61B 5/14551* (2013.01); *A61B 2503/12* (2013.01); *A61B 2505/09* (2013.01)

(56) References Cited

U.S. PATENT DOCUMENTS

| | | |
|---|---|---|
| 5,000,188 A | 3/1991 | Kojima |
| 5,111,539 A | 5/1992 | Hiruta et al. |
| 5,253,656 A | 10/1993 | Rincoe et al. |
| 5,304,112 A | 4/1994 | Mrklas et al. |
| 5,305,238 A | 4/1994 | Starr, III |
| 5,323,650 A | 6/1994 | Fullen et al. |
| 5,331,549 A | 7/1994 | Crawford, Jr. |
| 5,343,869 A | 9/1994 | Pross et al. |
| 5,410,471 A | 4/1995 | Alyfuku et al. |
| 5,435,315 A | 7/1995 | McPhee et al. |
| 5,441,047 A | 8/1995 | David |
| 5,542,420 A | 8/1996 | Goldman et al. |
| 5,570,301 A | 10/1996 | Barrus |
| 5,573,269 A | 11/1996 | Gentry et al. |
| 5,626,145 A | 5/1997 | Clapp et al. |
| 5,673,691 A | 10/1997 | Abrams et al. |
| 5,722,418 A | 3/1998 | Bro |
| 5,792,047 A | 8/1998 | Coggins |
| 5,813,993 A | 9/1998 | Kaplan et al. |
| 5,926,806 A | 7/1999 | Marshall et al. |
| 5,937,387 A | 8/1999 | Summerell et al. |
| 6,033,344 A | 3/2000 | Trulaske et al. |
| 6,049,281 A | 4/2000 | Osterweil |
| 6,080,106 A | 6/2000 | Lloyd et al. |
| 6,083,156 A | 7/2000 | Lisiecki |
| 6,104,296 A | 8/2000 | Yasuchi et al. |
| 6,148,280 A | 11/2000 | Kramer |
| 6,149,586 A | 11/2000 | Elkind |
| 6,190,314 B1 | 2/2001 | Ark et al. |
| 6,198,394 B1 | 3/2001 | Jacobsen et al. |
| 6,203,495 B1 | 3/2001 | Bardy |
| 6,269,339 B1 | 7/2001 | Silver |
| 6,281,594 B1 | 8/2001 | Sarich |
| 6,291,900 B1 | 9/2001 | Tiemann et al. |
| 6,293,771 B1 | 9/2001 | Haney et al. |
| 6,307,476 B1 | 10/2001 | Smith et al. |
| 6,309,342 B1 | 10/2001 | Blazey et al. |
| 6,334,837 B1 | 1/2002 | Hein et al. |
| 6,345,839 B1 | 2/2002 | Kuboki et al. |
| 6,353,764 B1 | 3/2002 | Imagawa et al. |
| 6,369,337 B1 | 4/2002 | Machiyama |
| 6,381,577 B1 | 4/2002 | Brown |
| 6,383,136 B1 | 5/2002 | Jordan |
| 6,408,263 B1 | 6/2002 | Summers |
| 6,425,862 B1 | 7/2002 | Brown |
| 6,450,530 B1 | 9/2002 | Frasher et al. |
| 6,452,862 B1 | 9/2002 | Tomotani |
| 6,546,286 B2 | 4/2003 | Olson |
| 6,572,558 B2 | 6/2003 | Masakov et al. |
| 6,585,645 B2 | 7/2003 | Hutchinson |
| 6,594,607 B2 | 7/2003 | Lavery |
| 6,646,556 B1 | 11/2003 | Smith et al. |
| 6,648,820 B1 | 11/2003 | Sarel |
| 6,658,572 B1 | 12/2003 | Craig |
| 6,669,286 B2 | 12/2003 | Iusim |
| 6,673,027 B2 | 1/2004 | Fischer |
| 6,675,130 B2 | 1/2004 | Kanevsky et al. |
| 6,692,258 B1 | 2/2004 | Kurzweil et al. |
| 6,705,990 B1 | 3/2004 | Gallant et al. |
| 6,736,642 B2 | 5/2004 | Bajer et al. |
| 6,767,330 B2 | 7/2004 | Lavery et al. |
| 6,768,246 B2 | 7/2004 | Pelrine et al. |
| 6,781,067 B2 | 8/2004 | Montagnino et al. |
| 6,828,908 B2 | 12/2004 | Clark |
| 6,832,987 B2 | 12/2004 | David et al. |
| 6,850,798 B2 | 2/2005 | Morgan |
| 6,918,769 B2 | 7/2005 | Rink |
| 6,931,359 B2 | 8/2005 | Tamada |
| 6,982,497 B2 | 1/2006 | Rome |
| 7,005,757 B2 | 2/2006 | Pandian |
| 7,027,621 B2 | 4/2006 | Prokoski |
| 7,063,665 B2 | 6/2006 | Hasegawa et al. |
| 7,074,198 B2 | 7/2006 | Krullaards |
| 7,104,965 B1 | 9/2006 | Jiang et al. |
| 7,109,872 B2 | 9/2006 | Balaban et al. |
| 7,128,577 B2 | 10/2006 | Renaud |
| 7,152,024 B2 | 12/2006 | Marschner et al. |
| 7,155,158 B1 | 12/2006 | Iuppa et al. |
| 7,163,489 B1 | 1/2007 | Nelson |
| 7,188,151 B2 | 3/2007 | Kumar et al. |
| 7,233,312 B2 | 6/2007 | Stern et al. |
| 7,273,453 B2 | 9/2007 | Shallengerger |
| 7,304,580 B2 | 12/2007 | Sullivan et al. |
| 7,315,249 B2 | 1/2008 | Littell |
| 7,351,206 B2 | 4/2008 | Suzuki |
| 7,399,276 B1 | 7/2008 | Brown et al. |
| 7,407,484 B2 | 8/2008 | Korman |
| 7,481,779 B2 | 1/2009 | Large |
| 7,598,881 B2 | 10/2009 | Morgan |
| 7,624,037 B2 | 11/2009 | Bost |
| 7,652,582 B2 | 1/2010 | Littell |
| 7,689,271 B1 | 3/2010 | Sullivan |
| 7,717,866 B2 | 5/2010 | Damen |
| 7,771,318 B2 | 8/2010 | Narayanaswami |
| 7,830,249 B2 | 11/2010 | Dorneich et al. |
| 7,844,347 B2 | 11/2010 | Brabec et al. |
| 7,849,115 B2 | 12/2010 | Reiner |
| 7,901,324 B2 | 3/2011 | Kodama |
| 7,958,002 B2 | 6/2011 | Bost |
| 7,972,266 B2 | 7/2011 | Gobeyn et al. |
| 7,988,627 B2 | 8/2011 | Bagan |
| 8,015,022 B2 | 9/2011 | Gore |
| 8,018,346 B2 | 9/2011 | Gottlieb et al. |
| 8,019,121 B2 | 9/2011 | Marks |
| 8,021,298 B2 | 9/2011 | Baird et al. |
| 8,024,202 B2 | 9/2011 | Carroll |
| 8,030,786 B2 | 10/2011 | Jackson et al. |
| 8,038,615 B2 | 10/2011 | Gobeyn |
| 8,081,083 B2 | 12/2011 | Hinterlong |
| 8,083,676 B2 | 12/2011 | Halliday |
| 8,092,226 B2 | 1/2012 | Findlay |
| 8,095,641 B2 | 1/2012 | Aggarwal et al. |
| 8,103,333 B2 | 1/2012 | Tran |
| 8,179,269 B2 | 5/2012 | Yanagi et al. |
| 8,180,457 B2 | 5/2012 | Matos |
| 8,200,323 B2 | 6/2012 | Dibenedetto et al. |
| 8,203,454 B2 | 6/2012 | Knight et al. |
| 8,219,184 B2 | 7/2012 | Stelzer et al. |
| 8,235,895 B2 | 8/2012 | David |
| 8,308,562 B2 | 11/2012 | Patton |
| 8,359,231 B2 | 1/2013 | Fitzpatrick et al. |
| 8,428,962 B1 | 4/2013 | Brinkley et al. |
| 8,477,039 B2 | 7/2013 | Gleckler et al. |
| 8,487,456 B2 | 7/2013 | Donelan et al. |
| 8,597,121 B2 | 12/2013 | Andres Del Valle |

(56) References Cited

U.S. PATENT DOCUMENTS

| | | |
|---|---|---|
| 8,597,142 B2 | 12/2013 | Mayles et al. |
| 8,612,247 B2 | 12/2013 | Sawano |
| 8,636,670 B2 | 1/2014 | Ferren et al. |
| 8,704,110 B2 | 4/2014 | Forshaw et al. |
| 8,738,129 B2 | 5/2014 | Packer et al. |
| 8,775,196 B2 | 7/2014 | Simpson et al. |
| 8,956,292 B2 | 2/2015 | Wekell et al. |
| 9,043,217 B2 | 5/2015 | Cashman et al. |
| 9,044,172 B2 | 6/2015 | Baxi et al. |
| 9,364,714 B2 | 6/2016 | Koduri et al. |
| 2001/0039372 A1 | 11/2001 | Yasushi et al. |
| 2001/0040591 A1 | 11/2001 | Abbott et al. |
| 2001/0041845 A1 | 11/2001 | Kim |
| 2001/0042004 A1 | 11/2001 | Taub |
| 2002/0050924 A1 | 5/2002 | Mahbub |
| 2002/0062069 A1 | 5/2002 | Mault |
| 2002/0077534 A1 | 6/2002 | Durousseau |
| 2002/0087093 A1 | 7/2002 | Chai |
| 2002/0095099 A1 | 7/2002 | Quyen et al. |
| 2002/0108576 A1 | 8/2002 | Lely et al. |
| 2002/0132092 A1 | 9/2002 | Wagner |
| 2002/0156351 A1 | 10/2002 | Sagel |
| 2002/0167486 A1 | 11/2002 | Tan et al. |
| 2002/0183644 A1 | 12/2002 | Levendowski et al. |
| 2002/0193707 A1 | 12/2002 | Atlas et al. |
| 2002/0197591 A1 | 12/2002 | Ebersole et al. |
| 2003/0010345 A1 | 1/2003 | Koblasz et al. |
| 2003/0058111 A1 | 3/2003 | Lee et al. |
| 2003/0060957 A1 | 3/2003 | Okamura et al. |
| 2003/0073552 A1 | 4/2003 | Knight |
| 2003/0109322 A1 | 6/2003 | Funk et al. |
| 2003/0113698 A1 | 6/2003 | Von Der Geest et al. |
| 2003/0149379 A1 | 8/2003 | Krullaards |
| 2003/0154107 A1 | 8/2003 | Medvedeff |
| 2003/0163351 A1 | 8/2003 | Brown et al. |
| 2003/0173120 A1 | 9/2003 | Desrochers et al. |
| 2003/0181830 A1 | 9/2003 | Guimond et al. |
| 2003/0201978 A1 | 10/2003 | Lee et al. |
| 2003/0204130 A1 | 10/2003 | Colston, Jr. et al. |
| 2003/0209113 A1 | 11/2003 | Brooks et al. |
| 2003/0212579 A1 | 11/2003 | Brown et al. |
| 2003/0214408 A1 | 11/2003 | Grajales et al. |
| 2003/0222440 A1 | 12/2003 | Basir |
| 2003/0226695 A1 | 12/2003 | Mault |
| 2004/0002634 A1 | 1/2004 | Nihtila |
| 2004/0004547 A1 | 1/2004 | Appelt et al. |
| 2004/0015191 A1 | 1/2004 | Otman et al. |
| 2004/0095378 A1 | 5/2004 | Vigue et al. |
| 2004/0100283 A1 | 5/2004 | Meyer et al. |
| 2004/0148140 A1 | 7/2004 | Tarassenko et al. |
| 2004/0152956 A1 | 8/2004 | Korman |
| 2004/0162466 A1 | 8/2004 | Quy |
| 2004/0167381 A1 | 8/2004 | Lichter et al. |
| 2004/0193068 A1 | 9/2004 | Burton et al. |
| 2004/0195876 A1 | 10/2004 | Huiban |
| 2004/0214148 A1 | 10/2004 | Salvino et al. |
| 2004/0222892 A1 | 11/2004 | Balaban |
| 2004/0242976 A1 | 12/2004 | Abreu |
| 2004/0260156 A1 | 12/2004 | David |
| 2004/0263633 A1 | 12/2004 | Shinohara et al. |
| 2005/0075542 A1 | 4/2005 | Goldreich |
| 2005/0101845 A1 | 5/2005 | Nihtila |
| 2005/0108086 A1 | 5/2005 | Kosman |
| 2005/0113650 A1 | 5/2005 | Pacione et al. |
| 2005/0124864 A1 | 6/2005 | Mack et al. |
| 2005/0164833 A1 | 7/2005 | Florio |
| 2005/0165284 A1 | 7/2005 | Gefen |
| 2005/0181347 A1 | 8/2005 | Barnes |
| 2005/0237385 A1 | 10/2005 | Kosaka et al. |
| 2005/0250996 A1 | 11/2005 | Shirai et al. |
| 2005/0260548 A1 | 11/2005 | Nava |
| 2005/0268401 A1 | 12/2005 | Dixon et al. |
| 2005/0270163 A1 | 12/2005 | Littell |
| 2005/0273890 A1 | 12/2005 | Flaherty et al. |
| 2006/0001545 A1 | 1/2006 | Wolf |
| 2006/0026036 A1 | 2/2006 | Mahmood |
| 2006/0030783 A1 | 2/2006 | Tsai et al. |
| 2006/0047188 A1 | 3/2006 | Bohan |
| 2006/0074708 A1 | 4/2006 | Woods |
| 2006/0090135 A1 | 4/2006 | Fukuda |
| 2006/0122863 A1 | 6/2006 | Gottesman et al. |
| 2006/0135857 A1 | 6/2006 | Ho et al. |
| 2006/0155175 A1 | 7/2006 | Ogino et al. |
| 2006/0183980 A1 | 8/2006 | Yang |
| 2006/0203991 A1 | 9/2006 | Kramer et al. |
| 2006/0240395 A1 | 10/2006 | Faist et al. |
| 2006/0241977 A1 | 10/2006 | Fitzgerald et al. |
| 2006/0253303 A1 | 11/2006 | Brown |
| 2006/0267747 A1 | 11/2006 | Kondo |
| 2006/0287883 A1 | 12/2006 | Turgiss et al. |
| 2007/0004969 A1 | 1/2007 | Kong et al. |
| 2007/0011273 A1 | 1/2007 | Greenstein et al. |
| 2007/0016449 A1 | 1/2007 | Cohen et al. |
| 2007/0017531 A1 | 1/2007 | Large |
| 2007/0038153 A1 | 2/2007 | Basson et al. |
| 2007/0050715 A1 | 3/2007 | Behar |
| 2007/0055185 A1 | 3/2007 | Trandafir et al. |
| 2007/0055549 A1 | 3/2007 | Moore et al. |
| 2007/0083384 A1 | 4/2007 | Geslak et al. |
| 2007/0118398 A1 | 5/2007 | Perls |
| 2007/0136093 A1 | 6/2007 | Rankin |
| 2007/0139362 A1 | 6/2007 | Colton et al. |
| 2007/0146131 A1 | 6/2007 | Boverie |
| 2007/0149360 A1 | 6/2007 | Narayanaswami |
| 2007/0169364 A1 | 7/2007 | Townsend et al. |
| 2007/0179360 A1 | 8/2007 | Mikat |
| 2007/0191727 A1 | 8/2007 | Fadem |
| 2007/0193811 A1 | 8/2007 | Breed et al. |
| 2007/0219419 A1 | 9/2007 | Kenknight et al. |
| 2007/0225118 A1 | 9/2007 | Giorno |
| 2007/0225585 A1 | 9/2007 | Washbon et al. |
| 2007/0244724 A1 | 10/2007 | Pendergast et al. |
| 2007/0256494 A1 | 11/2007 | Nakamura et al. |
| 2007/0270909 A1 | 11/2007 | Saketkhou |
| 2007/0276202 A1 | 11/2007 | Raisanen et al. |
| 2007/0282177 A1 | 12/2007 | Pilz |
| 2007/0296556 A1 | 12/2007 | Wang et al. |
| 2007/0299325 A1 | 12/2007 | Farrell et al. |
| 2008/0001735 A1 | 1/2008 | Tran |
| 2008/0001736 A1 | 1/2008 | Steadman et al. |
| 2008/0052837 A1 | 3/2008 | Blumberg |
| 2008/0077620 A1 | 3/2008 | Gilley et al. |
| 2008/0081963 A1 | 4/2008 | Naghavi et al. |
| 2008/0083416 A1 | 4/2008 | Xia et al. |
| 2008/0015422 A1 | 6/2008 | Wessel |
| 2008/0140140 A1 | 6/2008 | Grimley et al. |
| 2008/0146892 A1 | 6/2008 | Leboeuf et al. |
| 2008/0150889 A1 | 6/2008 | Stern |
| 2008/0161654 A1 | 7/2008 | Teller et al. |
| 2008/0171914 A1 | 7/2008 | Ouwekerk et al. |
| 2008/0177158 A1 | 7/2008 | Teller et al. |
| 2008/0177341 A1 | 7/2008 | Bowers |
| 2008/0177614 A1 | 7/2008 | An et al. |
| 2008/0177836 A1 | 7/2008 | Bennett |
| 2008/0188777 A1 | 8/2008 | Bedziouk |
| 2008/0193905 A1 | 8/2008 | Leung |
| 2008/0194995 A1 | 8/2008 | Grady-Van Den Nieuwboer |
| 2008/0200774 A1 | 8/2008 | Luo |
| 2008/0218331 A1 | 9/2008 | Baillot |
| 2008/0228046 A1 | 9/2008 | Futatsuyama et al. |
| 2008/0242521 A1 | 10/2008 | Einav |
| 2008/0242951 A1 | 10/2008 | Jung et al. |
| 2008/0242952 A1 | 10/2008 | Jung et al. |
| 2008/0258921 A1 | 10/2008 | Woo et al. |
| 2008/0292151 A1 | 11/2008 | Kurtz et al. |
| 2008/0294018 A1 | 11/2008 | Kurtz et al. |
| 2008/0304712 A1 | 12/2008 | Rowe et al. |
| 2008/0306357 A1 | 12/2008 | Korman |
| 2008/0306762 A1 | 12/2008 | James |
| 2009/0002178 A1 | 1/2009 | Guday et al. |
| 2009/0030290 A1 | 1/2009 | Kozuch et al. |
| 2009/0030767 A1 | 1/2009 | Morris et al. |
| 2009/0040196 A1 | 2/2009 | Duckstein |
| 2009/0047644 A1 | 2/2009 | Mensah |

(56) References Cited

U.S. PATENT DOCUMENTS

| | | |
|---|---|---|
| 2009/0047645 A1 | 2/2009 | Dibenedetto et al. |
| 2009/0055204 A1 | 2/2009 | Pennington et al. |
| 2009/0058661 A1 | 3/2009 | Glecker et al. |
| 2009/0137882 A1 | 5/2009 | Baudino et al. |
| 2009/0149721 A1 | 6/2009 | Yang |
| 2009/0149799 A1 | 6/2009 | Dacey, Jr. et al. |
| 2009/0156888 A1 | 6/2009 | Su et al. |
| 2009/0160640 A1 | 6/2009 | Leung et al. |
| 2009/0173549 A1 | 7/2009 | Lev |
| 2009/0177688 A1 | 7/2009 | Karlsen et al. |
| 2009/0178858 A1 | 7/2009 | Daniels et al. |
| 2009/0198521 A1 | 8/2009 | Barker |
| 2009/0209829 A1 | 8/2009 | Yanagidaira et al. |
| 2009/0216558 A1 | 8/2009 | Reisman et al. |
| 2009/0231145 A1 | 9/2009 | Wada et al. |
| 2009/0241177 A1 | 9/2009 | Bluth |
| 2009/0287101 A1 | 11/2009 | Ferren et al. |
| 2009/0287191 A1 | 11/2009 | Ferren |
| 2009/0298025 A1 | 12/2009 | Raber |
| 2009/0300616 A1 | 12/2009 | Sicurello et al. |
| 2009/0307025 A1 | 12/2009 | Menon |
| 2009/0319297 A1 | 12/2009 | Hernandez et al. |
| 2009/0324024 A1 | 12/2009 | Worthington |
| 2010/0010365 A1 | 1/2010 | Terao et al. |
| 2010/0014711 A1 | 1/2010 | Camhi et al. |
| 2010/0049004 A1 | 2/2010 | Edman et al. |
| 2010/0049541 A1 | 2/2010 | Pollard et al. |
| 2010/0063837 A1 | 3/2010 | Bellante et al. |
| 2010/0130808 A1 | 5/2010 | Hattori |
| 2010/0131283 A1 | 5/2010 | Linthicum et al. |
| 2010/0169118 A1 | 7/2010 | Rottsolk et al. |
| 2010/0169219 A1 | 7/2010 | Sellers et al. |
| 2010/0205541 A1 | 8/2010 | Rapaport et al. |
| 2010/0225489 A1 | 9/2010 | Hinterlong |
| 2010/0240458 A1 | 9/2010 | Gaiba et al. |
| 2010/0259043 A1 | 10/2010 | Balsamo |
| 2010/0261978 A1 | 10/2010 | Lithgow |
| 2010/0283265 A1 | 11/2010 | Rastegar et al. |
| 2010/0286567 A1 | 11/2010 | Wolfe et al. |
| 2010/0292545 A1 | 11/2010 | Berka et al. |
| 2010/0293267 A1 | 11/2010 | Ribak et al. |
| 2010/0298656 A1 | 11/2010 | McCombie et al. |
| 2010/0299257 A1 | 11/2010 | Turk |
| 2010/0305480 A1 | 12/2010 | Guoyi et al. |
| 2010/0312606 A1 | 12/2010 | Gala |
| 2010/0332250 A1 | 12/2010 | Simpson |
| 2011/0030838 A1 | 2/2011 | Turiello |
| 2011/0033830 A1 | 2/2011 | Cherian |
| 2011/0035231 A1 | 2/2011 | Firminger et al. |
| 2011/0046688 A1 | 2/2011 | Schwibner et al. |
| 2011/0055720 A1 | 3/2011 | Potter et al. |
| 2011/0060252 A1 | 3/2011 | Simonsen et al. |
| 2011/0080290 A1 | 4/2011 | Baxi et al. |
| 2011/0098056 A1 | 4/2011 | Rhoads et al. |
| 2011/0119075 A1 | 5/2011 | Dhoble |
| 2011/0125662 A1 | 5/2011 | Perry et al. |
| 2011/0137211 A1 | 6/2011 | Weisberg |
| 2011/0137669 A1 | 6/2011 | Bennett |
| 2011/0152635 A1 | 6/2011 | Morris et al. |
| 2011/0152696 A1 | 6/2011 | Ryan |
| 2011/0161100 A1 | 6/2011 | Peak et al. |
| 2011/0172744 A1 | 7/2011 | Davis et al. |
| 2011/0183305 A1 | 7/2011 | Orbach |
| 2011/0196212 A1 | 8/2011 | Peters et al. |
| 2011/0201960 A1 | 8/2011 | Price |
| 2011/0213664 A1 | 9/2011 | Osterhout et al. |
| 2011/0238591 A1 | 9/2011 | Kerr et al. |
| 2011/0257537 A1 | 10/2011 | Alatriste |
| 2011/0269601 A1 | 11/2011 | Nelson et al. |
| 2011/0270135 A1 | 11/2011 | Dooley et al. |
| 2011/0275939 A1 | 11/2011 | Walsh et al. |
| 2011/0285146 A1 | 11/2011 | Kozinsky et al. |
| 2011/0295466 A1 | 12/2011 | Ostu et al. |
| 2011/0295656 A1 | 12/2011 | Venkatasubramanian et al. |
| 2012/0007367 A1 | 1/2012 | Chang |
| 2012/0010488 A1 | 1/2012 | Henry et al. |
| 2012/0035433 A1 | 2/2012 | Chance |
| 2012/0040799 A1 | 2/2012 | Jaquish et al. |
| 2012/0052971 A1 | 3/2012 | Bentley |
| 2012/0071731 A1 | 3/2012 | Gottesman |
| 2012/0075483 A1 | 3/2012 | Paoletti |
| 2012/0086249 A1 | 4/2012 | Hotary et al. |
| 2012/0117020 A1 | 5/2012 | Davis et al. |
| 2012/0122430 A1 | 5/2012 | Hutchings et al. |
| 2012/0127157 A1 | 5/2012 | Adler et al. |
| 2012/0130196 A1 | 5/2012 | Jain et al. |
| 2012/0139731 A1 | 6/2012 | Razoumov et al. |
| 2012/0143031 A1 | 6/2012 | Belalcazar et al. |
| 2012/0143374 A1 | 6/2012 | Mistry et al. |
| 2012/0146795 A1 | 6/2012 | Margon et al. |
| 2012/0154277 A1 | 6/2012 | Bar-Zeev et al. |
| 2012/0203465 A1 | 8/2012 | Callewaert et al. |
| 2012/0203491 A1 | 8/2012 | Sun et al. |
| 2012/0209563 A1 | 8/2012 | Takeda et al. |
| 2012/0215076 A1 | 8/2012 | Yang et al. |
| 2012/0215976 A1 | 8/2012 | Inoue |
| 2012/0253484 A1 | 10/2012 | Burich et al. |
| 2012/0271121 A1 | 10/2012 | Della Torre et al. |
| 2012/0271143 A1 | 10/2012 | Aragones et al. |
| 2012/0283929 A1 | 11/2012 | Wakita et al. |
| 2012/0289793 A1 | 11/2012 | Jain et al. |
| 2012/0290215 A1 | 11/2012 | Adler et al. |
| 2012/0302910 A1 | 11/2012 | Freeman et al. |
| 2012/0323590 A1 | 12/2012 | Udani |
| 2013/0009761 A1 | 1/2013 | Horseman |
| 2013/0009993 A1 | 1/2013 | Horseman |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1* | 1/2013 | Horseman ........... G06F 19/3418 600/301 |
| 2013/0012789 A1 | 1/2013 | Horseman |
| 2013/0012790 A1 | 1/2013 | Horseman |
| 2013/0012802 A1 | 1/2013 | Horseman |
| 2013/0013327 A1 | 1/2013 | Horseman |
| 2013/0013331 A1 | 1/2013 | Horseman |
| 2013/0056981 A1 | 3/2013 | Mullins et al. |
| 2013/0097093 A1 | 4/2013 | Kolber et al. |
| 2013/0158423 A1 | 6/2013 | Kapoor |
| 2013/0178960 A1 | 7/2013 | Sheehan et al. |
| 2013/0217350 A1 | 8/2013 | Singh |
| 2013/0226413 A1 | 8/2013 | Cuddihy et al. |
| 2013/0234826 A1 | 9/2013 | Sekiguchi et al. |
| 2013/0243208 A1 | 9/2013 | Fawer |
| 2013/0281798 A1 | 10/2013 | Rau et al. |
| 2013/0282609 A1 | 10/2013 | Au et al. |
| 2013/0289889 A1 | 10/2013 | Yuen et al. |
| 2013/0297219 A1 | 11/2013 | Bangera et al. |
| 2013/0297344 A1 | 11/2013 | Cosentino et al. |
| 2013/0308099 A1 | 11/2013 | Stack |
| 2013/0331993 A1 | 12/2013 | Detsch et al. |
| 2013/0334851 A1 | 12/2013 | Hoell et al. |
| 2014/0041105 A1 | 2/2014 | Zemlak |
| 2014/0067001 A1 | 3/2014 | Schwibner et al. |
| 2014/0100464 A1 | 4/2014 | Kaleal et al. |
| 2014/0107718 A1 | 4/2014 | Foote et al. |
| 2014/0129401 A1 | 5/2014 | Kruz et al. |
| 2014/0156259 A1 | 6/2014 | Dolan et al. |
| 2014/0172461 A1 | 6/2014 | Rogers |
| 2014/0222095 A1 | 8/2014 | Einy |
| 2014/0304020 A1 | 10/2014 | Casper |
| 2014/0317914 A1 | 10/2014 | Shaker |
| 2014/0372133 A1 | 12/2014 | Austrum |
| 2015/0025928 A1 | 1/2015 | Kang et al. |
| 2015/0050623 A1* | 2/2015 | Falash ..................... G09B 9/24 434/38 |
| 2015/0134347 A1 | 5/2015 | Faurie et al. |
| 2015/0199494 A1 | 7/2015 | Koduri et al. |
| 2015/0222096 A1 | 8/2015 | Nakayama et al. |
| 2015/0338265 A1 | 11/2015 | Carreel et al. |
| 2015/0375028 A1 | 12/2015 | Oteman et al. |
| 2016/0132046 A1 | 5/2016 | Beoughter et al. |

(56) References Cited

U.S. PATENT DOCUMENTS

| | | | |
|---|---|---|---|
| 2016/0321935 | A1 | 11/2016 | Mohler et al. |
| 2017/0245806 | A1 | 8/2017 | Elhawary et al. |
| 2017/0290516 | A1 | 10/2017 | Nguyen et al. |

FOREIGN PATENT DOCUMENTS

| | | | |
|---|---|---|---|
| CN | 101115438 | A | 1/2008 |
| CN | 201127606 | Y | 10/2008 |
| CN | 101454050 | A | 6/2009 |
| CN | 101930125 | A | 12/2010 |
| DE | 102005048496 | A1 | 4/2007 |
| EP | 1407713 | B1 | 9/2008 |
| EP | 2151355 | A1 | 2/2010 |
| EP | 2248461 | A2 | 11/2010 |
| EP | 2924674 | A1 | 9/2015 |
| JP | 05049603 | A | 3/1993 |
| JP | H07204168 | A | 8/1995 |
| JP | H10312241 | A | 11/1998 |
| JP | H11328593 | A | 11/1999 |
| JP | 2000037357 | A | 2/2000 |
| JP | 2000342537 | A | 12/2000 |
| JP | 2001187030 | A | 7/2001 |
| JP | 2001209717 | A | 8/2001 |
| JP | 2001236141 | A | 8/2001 |
| JP | 2001356849 | A | 12/2001 |
| JP | 2002065630 | A | 3/2002 |
| JP | 2002109061 | A | 4/2002 |
| JP | 2002159052 | A | 5/2002 |
| JP | 2002183647 | A | 6/2002 |
| JP | 2002215880 | A | 8/2002 |
| JP | 2002259120 | A | 9/2002 |
| JP | 2002291952 | A | 10/2002 |
| JP | 2003070774 | A | 3/2003 |
| JP | 2003091598 | A | 3/2003 |
| JP | 2003521972 | A | 7/2003 |
| JP | 2003235813 | A | 8/2003 |
| JP | 2003247991 | A | 9/2003 |
| JP | 2003256578 | A | 9/2003 |
| JP | 2003310580 | A | 11/2003 |
| JP | 2004113581 | A | 4/2004 |
| JP | 2004135829 | A | 5/2004 |
| JP | 3109753 | U | 6/2005 |
| JP | 2005287688 | A | 10/2005 |
| JP | 2005321869 | A | 11/2005 |
| JP | 2006085262 | A | 3/2006 |
| JP | 2006106952 | A | 4/2006 |
| JP | 2006178805 | A | 7/2006 |
| JP | 2006239157 | A | 9/2006 |
| JP | 2008099834 | A | 1/2008 |
| JP | 2008110032 | A | 5/2008 |
| JP | 2008178546 | A | 8/2008 |
| JP | 2008230366 | A | 10/2008 |
| JP | 2008264188 | A | 11/2008 |
| JP | 2008304978 | A | 12/2008 |
| JP | 2009171544 | A | 7/2009 |
| JP | 2009532072 | A | 9/2009 |
| JP | 2009301360 | A | 12/2009 |
| JP | 2010003070 | A | 1/2010 |
| JP | 2010181324 | A | 8/2010 |
| JP | 2010538701 | A | 12/2010 |
| JP | 2011067708 | A | 4/2011 |
| JP | 2011120787 | A | 6/2011 |
| JP | 2011123579 | A | 6/2011 |
| WO | 9601585 | A1 | 1/1996 |
| WO | 2001028416 | A1 | 4/2001 |
| WO | 2001086403 | A2 | 11/2001 |
| WO | 03077110 | A2 | 9/2003 |
| WO | 2005064447 | A2 | 7/2005 |
| WO | 2006022465 | A2 | 3/2006 |
| WO | 2008044325 | A1 | 4/2008 |
| WO | 2010048145 | A1 | 4/2010 |
| WO | 2010051037 | A1 | 5/2010 |
| WO | 2010067275 | A1 | 6/2010 |
| WO | 2014023422 | | 2/2014 |

OTHER PUBLICATIONS

"Augmented Reality", retrieved from <http://en.wikipedia.org/wiki/Augmented_reality>, May 30, 2012. pp. (1-18).
"Biofeedback—MayoClinic.com", retrieved from <http://www.mayoclinic.com/health/biofeedback/MY01072>, May 7, 2012. (pp. 1-2).
"Cardinus Risk Management | Ergonomic & DSE Risk Assessments", retrieved from <http://www.cardinus.com/>, Sep. 12, 2012. (pp. 1-2).
"Chronic diseases and health promotion" Centers for Disease Control and Prevention, 2011, <http://www.cdc.gov/chronicdisease/overview> [Accessed Feb. 2, 2011].
"Clever toilet checks on your health", retrieved from <http://articles.cnn.com/2005-06-28/tech/spark.toilet_1_toilet-toto-bathroom?_s=PM:TECH>, Jun. 28, 2005. (pp. 1-2).
"Electroencephalography (EEG)", retieved from <http://www.emedicinehealth.com/script/main/art.asp?articlekey-59319&pf=3&page=1>, Jun. 11, 2012. (pp. 1-4).
"Emotiv|EEG System|Electroencephalography", retrieved from <www.emotiv.com/index.asp>, Jun. 11, 2012. (pp. 1-2).
"EmotivEPOC Software Devlopment Kit", retrieved from <www.emotiv.com/store/hardware/epoc-bci-eeg/developer-neuroheadset/>, Jun. 11, 2012. (pp. 1-2).
"Kinect—Xbox.com", retrieved from <http://www.xbox.com/en-US/kinect>, Jun. 11, 2012. (pp. 1-3).
"Making a Difference", World Health Organisation, Geneva: WHO, 1999, pp. 1-136.
"MomToBe: The Pregnancy Assistant 3.0", retreved from <http://3d2f.com/programs/4-230-momtobe-the-pregnancy-assistant-download.shtml>, Jun. 11, 2012. (pp. 1-2).
"Murray Hill, WellMed Team to Offer Next Generation Online Preventive Health Services" ProQuest, PR Newswire, New York, Nov. 3, 1999, 3 pages.
"National Health Expenditure Data", Centers for Medicare & Medicaid Services, available at: <https://www.cms.gov/Research-Statistics-Data-and-Systems/Statistics-Trends-and-Reports/NationalHealthExpendData/index.html>, accessed Nov. 18, 2013, pp. 1-2.
"Office Athlete Software Prevents Common Repetitive Stress Injuries", retrieved from <http://www.officeathlete.com/>, Sep. 14, 2012. (pp. 1-2).
"OSHA Ergonomic Solutions: Computer Workstations eTool—Checklists", retrieved from <www.osha.gov/SLTC/etools/computerworkstations/checklist.html>, Jun. 11, 2012. (pp. 1-5).
"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).
"OSHA Ergonomic Solutions: Computer Workstations eTool—Work Process and Recognition", retrieved from <www.osha.gov/SLTC/etools/computerworkstations/workprocess.html>, Jun. 11, 2012. (pp. 1-2).
"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).
"Osha Ergonomic Solutions: Computer Workstations eTool—Workstations eTool", retrieved from <www.osha.gov/SLTC/etools/computerworkstations/index.html>, Jun. 11, 2012. (p. 1).
"Philips Research—Download Pictures", retrieved from <http://www.research.philips.com/downloads/pictures/healthcare-personal.html>, May 7, 2012. (pp. 1-2).
"Philips Research Technology Backgrounder—MyHeart project", retrieved from <http://www.research.philips.com/technologies/heartcycle/myheart-gen.html>, May 7, 2012. (pp. 1-3).
"Piezo Electric Energy Harvester", Mide Technology Corporation, retrieved Nov. 18, 2013, pp. 1-2.
"Research programs—Philips Research", retrieved from <http://www.research.philips.com/programs/index.html>, May 7, 2012. (pp. 1-2).
"RJL Systems, Products", retrieved from <http://www.rjlsystems.com/products.shtml>, May 7, 2012. (p. 1).

(56) References Cited

OTHER PUBLICATIONS

"Signal Conditioning Piezoelectric Sensors", (PDF) Texas Instruments, Application Report SLOA033A, Sep. 2000, pp. 1-6.
"SmartHeart SE102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).
"Speedy Assessment I Chiropractic Assessment and Patient Education", retrieved from <http://speedyassessment.com/>, May 7, 2012. (pp. 1-3).
"Stress Thermometer", retrieved from <http://www.biof.com/onlinestore/stressthermometer.asp?redirect=yes>, May 7, 2012. (pp. 1-4).
"The Wellness Imperative, Creating More Effective Organizations", World Economic Forum, 2010. (pp. 1-20).
"Wireless measurement devices—Philips", retreved from <http://www.healthcare.philips.com/us_en/products/telehealth/Products/devices.wpd>, May 7, 2012. (pp. 1-2).
"WorkPace : RSI Injury Prevention Software, Stretch Break Exercise Reminder Software", retrieved from <http://www.workpace.com/>, Sep. 14, 2012. (p. 1).
"Workrave", retrieved from <http://www.workrave.org/>, Sep. 14, 2012. (p. 1).
"www.mydailyhealth.com" retrieved from Internet Archive Wayback Machine, 1999, 20 pages.
"Footrests—Adjustable Footrest Solutions for the Office", Ergo in Demand, Aug. 20, 2009, pp. 1-4, Ergo in Demand Inc., www.ergoindemand.com/footrest.html.
"Pulse Oximetry" SparkFun Electronics, Oct. 7, 2005 (p. 1).
"Statement in accordance with the Notice from the European Patent Office dated Oct. 1, 2007 concerning business methods" Nov. 1, 2007, 1 page, XP002456414.
Abstract for "Psychosocial job factors and symptoms from the locomotor system—a multicausal analysis", retrieved from <http://www.ncbi.nlm.nih.gov/pubmed/1962160>, May 7, 2012. (p. 1).
Abstract for "Signal Characteristics of EMG at Different Levels of Muscle Tension", retrieved from <http://onlinelibrary.wiley.com/doi/10.1111/j.1748-1716.1976.tb10195.x/abstract>, May 7, 2012. (p. 1).
Aldana, S., "Financial Impact of health promotion programs: a comprehensive review of the literature", American Journal of Health Promotion,155, 2001, pp. 296-320.
Aldana, S., Merrill, R., Price, K, Hardy, A., and Hager, R., "Financial impact of a comprehensive multi-site worksite health promotion program", Preventive Medicine, 40, Jul. 2004, pp. 131-137.
Alfredo Vazquez Carazo, "Novel Piezoelectric Transducers for High Voltage Measurements", Jan. 2000, pp. 1-277.
Amato, Neil, "Top 20 companies for leadership development" CGMA Magazine, Sep. 23, 2013; available as of Dec. 13, 2015 at the website: http://www.cgma.org/magazine/news/pages/20138765.aspx?TestCookiesEnabled=redirect; pp. 1-5.
Baicker, K., Cutler, D., Song, Z., "Worksite wellness programs can generate savings", Health Affairs 29(2), Jan. 2010, pp. 1-8.
Bed-Check Co., Bed-Check Monitoring Systems, 2006.
Berger et al. 'Investing in Healthy Human Capital'—J Occup Environ Med. (JOEM) vol. 45, No. 12, dated Dec. 2003; pp. 1213-1225.
Berry, Leonard et al., "What's the Hard Return on Employee Wellness Programs?", Harvard Business Review, Dec. 2010. (pp. 1-10).
Brown et al, "Prowess Proactive Wellness Environment Support System", Dec. 10, 2009, pp. 1-19, www.hsi.gatech.edu/onsitecenter/index.php/PROWESS.
Burkus, David, "For Leaders, Looking Healthy Matters More than Looking Smart" Harvard Business Review, Jan. 2, 2015; available as of Dec. 13, 2015 at the website: https://hbr.org/2015/01/for-leaders-looking-healthy-matters-more-than-looking-smart.
Campbell et al., "The Rise of People-Centric Sensing", IEEE Computer Society, 2008, pp. 12-21, IEEE.
Chapman, L., "Expert opinions on 'best practice' in worksite health promotion (WHP)", Jul./Aug. 2004, pp. 1-13.
Chapman, L. "Meta-evaluation of worksite health promotion economic return studies: 2012 Update", Mar./Apr. 2012, pp. 1-13.
Chapman, Larry S. MPH, "Meta-evaluation of Worksite Health Promotion Economic Return Studies: 2005 Update", Jul./Aug. 2005. (pp. 1-11).
Collins English Dictionary, definition of mat, 2008, retrieved at www.collinsdictionary.com.
Edington, D.W., "Emerging research: a view from one research centre", American Journal of Health Promotion, 15(5), May/Jun. 2001, pp. 341-349.
Edington, M., Karjalainen, T., Hirschland, D., Edington, D.W., "The UAW-GM Health Promotion Program: Successful Outcomes", American Association of Occupational Health Nursing Journal.50, Jan. 2002, pp. 26-31.
EPO: "Notice from the European Patent Office dated Oct. 1, 2007 concerning business methods" Official Journal EPO, vol. 30, No. 11, Nov. 1, 2007, pp. 592-593, XP007905525.
Georgia Tech, "Prowess Proactive Wellness Environment Support System", Dec. 12, 2009, pp. 1-27, www.hsi.gatech.edu/onsitecenter/index.php/PROWESS.
Goetzel et al. "The Relationship Between Modifiable Health Risks and Health Care Expenditures: An Analysis of the Multi-Employer HERO Health Risk and Cost Database" Journal of Occupational Environmental Medicine, vol. 40, No. 10, Oct. 1998, 30 pages.
Goetzel et al. 'Estimating the Return-on-Investment From Changes in Employee Health Risks on TheDow Chemical company's Health Care Costs'—J Occup Environ Med. (JOEM) vol. 47, No. 8, dated Aug. 2005; pp. 759-768.
Goetzel et al. 'Health, Absence, Disability, and Presenteeism Cost Estimates of Certain Physical and MentalHealth Conditions Affecting U.S. Employers'—J Occup Environ Med. (JOEM) vol. 46, No. 4, dated Apr. 2004; pp. 398-412.
Goetzel et al. 'Second-Year Results of an Obesity Prevention Program at TheDow Chemical Company'—J Occup Environ Med. (JOEM) vol. 52, No. 3, dated Mar. 2010; pp. 291-302.
Goetzel et al. 'The Health and Productivity Cost Burden of the "Top 10" Physical and Mental HealthConditions Affecting Six Large U.S. Employers in 1999'—J Occup Environ Med. (JOEM) vol. 45, No. 1, dated Jan. 2003; pp. 5-14.
Goetzel et al. 'The Long-Term Impact of Johnson & Johnson's Health & Wellness Program onEmployee Health Risks'—J Occup Environ Med. (JOEM) vol. 44, No. 5, dated May 2002; pp. 417-424.
Goetzel et al. 'The Workforce Wellness Index'—J Occup Environ Med. (JOEM) vol. 55, No. 3, dated Mar. 2013; pp. 272-279.
Goetzel et al. The Predictive Validity of the HERO Scorecard in Determining Future Health Care Cost and Risk Trends—J Occup Environ Med. (JOEM) vol. 56, No. 2, dated Feb. 2014; pp. 136-144.
Health/Medical Writers eHealthcareWorld 2000. (May 1). MyDailyHealth.com (pp. 1-3).
Hemp, P., "Presenteeism: At Work—But Out of It", Harvard Business Review, Oct. 2004, pp. 49-58.
Hill, Jr., Randall W.; "How Virtual Humans Can Build Better Leaders" Harvard Business Review Jul. 25, 2014; pp. 1-4.
Horseman, S. J ., "Healthy Human Capital as a Business Strategy: The Saudi Aramco Wellness Program (SAWP)", American Society of Safety Engineers (ME Chapter), (9) Conference Proceedings. Bahrain. Feb. 2010, pp. 178-185.
Horseman, S.J., "ErgoWELL : An Integrative Strategy", SPE Paper #: SPE-152629. Society of Petroleum Engineers, MEHSSE. Paper and Workshop, Abu Dhabi, 2012, pp. 1-17.
Horseman, Samantha, et al.; "Gamefication of Health, Safety and the Environment {HSE): An Avatarial Solution" American Society of Safety Engineers 11th Professional Development Conference & Exhibition, Bahrain, Mar. 2014;pp. 1-10.
Index for "Micro-NanoMechatronics and Human Science (MHS), 2010 International Symposium Nov. 2010", retrieved from <http://ieeexplore.ieee.org/xpl/mostRecentIssuejsp?punumber=5658189> Ma 7, 2012. (pp. 1-5).
International Preliminary Report on Patentability for International Application No. PCT/US2012/045395, dated Jan. 7, 2014. (pp. 1-12).

(56) References Cited

OTHER PUBLICATIONS

International Preliminary Report on Patentability for International Application No. PCT/US2012/045401 dated Jan. 7, 2014. (pp. 1-9).
International Preliminary Report on Patentability for International Application No. PCT/US2012/045407 dated Jan. 7, 2014. (pp. 1-8).
International Preliminary Report on Patentability for International Application No. PCT/US2012/045410 dated Jan. 7, 2014. (pp. 1-8).
International Preliminary Report on Patentability for International Application No. PCT/US2012/045414 dated Jan. 7, 2014. (pp. 1-8).
International Preliminary Report on Patentability for International Application No. PCT/US2012/045419 dated Jan. 7, 2014. (pp. 1-11).
International Preliminary Report on Patentability for International Application No. PCT/US2012/045427 dated Jan. 7, 2014. (pp. 1-10).
International Preliminary Report on Patentability for International Application No. PCT/US2012/045435 dated Jan. 7, 2014. (pp. 1-10).
International Preliminary Report on Patentability for International Application No. PCT/US2012/045442 dated Jan. 7, 2014. (pp. 1-10).
International Preliminary Report on Patentability for International Application No. PCT/US2012/045447 dated Jan. 7, 2014. (pp. 1-8).
International Preliminary Report on Patentability for International Application No. PCT/US2012/045452 dated Jan. 7, 2014. (pp. 1-9).
International Search Report & Written Opinion for International Application No. PCT/US2012/045401, dated Feb. 5, 2013. (pp. 1-13).
International Search Report & Written Opinion for International Application No. PCT/US2012/045407, dated Jan. 23, 2013. (pp. 1-15).
International Search Report & Written Opinion for International Application No. PCT/US2012/045410, dated Jan. 31, 2013. (pp. 1-13).
International Search Report & Written Opinion for International Application No. PCT/US2012/045414, dated Mar. 25, 2013. (pp. 1-13).
International Search Report & Written Opinion for International Application No. PCT/US2012/045435, dated Jan. 25, 2013. (pp. 1-14).
International Search Report & Written Opinion for International Application No. PCT/US2012/045447, dated Jan. 18, 2013. (pp. 1-12).
International Search Report and Written Opinion for International Application No. PCT/US2004/045442, dated Nov. 7, 2012, pp. 1-14.
International Search Report and Written Opinion for International Application No. PCT/US2012/045395, dated Dec. 3, 2012, pp. 1-16.
International Search Report and Written Opinion for International Application No. PCT/US2012/045419, dated Dec. 6, 2012, pp. 1-16.
International Search Report and Written Opinion for International Application No. PCT/US2012/045427, dated Dec. 3, 2012, pp. 1-14.
International Search Report and Written Opinion for International Application No. PCT/US2012/045452, dated Dec. 3, 2012, pp. 1-14.
International Search Report and Written Opinion for PCT/US2014/056427 dated Apr. 22, 2015.
International Search Report and Written Opinion for PCT/US2014/069498 dated Apr. 1, 2015.
Agarabit Mina, et al., "A sEMG-based Method for Assessing the Design of Computer Mice" 26th Annual International Conference of the IEEE EMBS, Sep. 1-5, 2004; pp. 2450-2453.
Robertini, Nadia, et al., "Capture of Arm-Muscle Deformations using a Depth-Camera" 10 European Conference on Visual Media Production, London, UK, Nov. 6-7, 2013; pp. 1-10.
Anonymous: "Automated analyser"—Wikipedia, Jan. 16, 2015; https: ex.php?title=Automated_analyser&oldid=642687889 retrieved on Feb. 8, 2017; XP055343828 (pp. 1-4).
Hacker, et al. "Representation and visualization of variability in a 3D anatomical atlas using the kidney as an example." Medical Imaging. International Society for Optics and Photonics, 2006. XP055342027 (pp. 1-7).
International Search Report and Written Opinion for International Application No. PCT/US2016/064518; International Filing Date Dec. 2, 2016; Report dated Feb. 17, 2017; (pp. 1-16).
International Search Report and Written Opinion for International Application No. PCT/US2016/065042; International Filing Date Dec. 6, 2016; Report dated Mar. 17, 2017; pp. 1-15.
International Search Report and Written Opinion for International PCT application PCT/US2016/064520; International Filing Date Dec. 2, 2016; Report dated Mar. 27, 2017; pp. 1-10.
International Search Report and Written Opinion for International PCT application PCT/US2016/064521; International Filing Date Dec. 2, 2016; Report dated Mar. 20, 2017; pp. 1-17.
Stephens: "I am 38. My heart is only 33, but my lungs are aged 52. Why?" Mail Online; http://www. dailymail.co.uk/health/article-1249009/I-38-My-heart-only33-lungs-aged-52-Why.html; retrieved on Feb. 3, 2017; XP055342045 (pp. 1-7).
Jamison, Dean T., et al.; "The World Health Report 1999" World Health Organization, WHO Library Cataloguing in Publication Data, 1999; pp. 1-136.
Johns, G., "Presenteeism in the Workplace: A review and research agenda", Journal of Organizational Behavior, Jul. 31, 2009, pp. 519-542.
Kelly et al. The Novartis Health Index: A Method for Valuing the Economic Impact of Risk Reduction in a Workforce—J Occup Environ Med. (JOEM) vol. 52, No. 5, dated May 2010; pp. 528-535.
Kuriyama, Shigeru "Visualization model for a human action based on a visual perception" Measurement and Control, Japan, Journal of the Society of Instrument and Control Engineers, Dec. 10, 2006, vol. 45, No. 12, pp. 1024-1029.
Kymissis et al. "Parasitic Power Harvesting in Shoes" Digest of Papers, Second International Symposium on Wearable Computers, Pittsburgh, PA, Oct. 19-20, 1998, pp. 132-139, XP032385438.
Lamkin, Paul; "The best VR headsets: Oculust Rift, PlayStation VR, Gear VR, HTC Vive...virtual reality is back baby" 10 Sep. 16, 2015; available as of Oct. 21, 2015 at the website: http://www.wearable.com/headgear/the-best-ar-and-vrheadsets;pp. 1-1.
Myatt, Mike, "The #1 Reason Leadership Development Fails" Forbes, Dec. 19, 2012; available as of Dec. 13, 2015 at the website: http://www.forbes.com/sites/mikemyatt/2012/12/19/the-1-reason-leadership-development-fails/#7e53fcd834ce; pp.
Nintendo of America Inc., Wii Balance Board Operations Manual, 2008, pp. 1-10.
Nintendo of America Inc., Wii Fit Instruction Booklet, 2008, pp. 1-28.
Nintendo Wii Fit, https://www.youtube.com/watch?v=-Taruqvk30E, May 11, 2008.
Ovans, Andrea; What Resilience Means, and Why it Matters Harvard Business Review Jan. 5, 2015; pp. 1-6.
Priya, S., "Advances in Energy Harvesting Using Low Profile Piezoelectric Transducers", Materials Science & Engineering, Springer, Mar. 2007, pp. 165-182.
Prochaska et al. 'The Well-Being Assessment for Productivity'—J Occup Environ Med. (JOEM) vol. 53, No. 7, dated Jul. 2011; pp. 735-768.
Qlik Technology Partners available as of Oct. 21, 2015 at the website: http://www.qlik.com/us/partners/technologypartners;pp. 1-21.
Quick, James Campbell, et al. "Executive health: Building strength, managing risks" Academy of Management Executive, May 2000, vol. 14, No. 2, pp. 33-45.
Rao, Leena; "Backed by Google Ventures and Eric Schmidt, Urban Engines Wants to Solve Urban Congestion Using Data Intelligence" available as of Oct. 2, 2015 at the website: http://www.techcrunch.com/2014/05/15/backed-by-google-entures-and-eric-schmidt-urban.
Ready, Douglas A., et al.; "Are You a High Potential?" Harvard Business Review Jun. 2010; pp. 1-13.

(56) References Cited

OTHER PUBLICATIONS

Reidel, J.E., Baase, C., "The effect of disease prevention & health promotion on worksite productivity: a literature review", American Journal of Health Promotion, 15:3, Jan./Feb. 2001, pp. 167-191, 243.
Roberts, R.O.,Bergstralh, E.J., Schmidt, L, Jacobsoen,S.J., "Comparison of Self Reported and Medical Record Health Care Utilization Measures", Journal of Clinical Epidemiology, 49:9, Feb. 1996, pp. 989-995.
Seligman, Martin E.P., "Building Resilience" Harvard Business Review from the Apr. 2011 issue; available as of Dec. 13, 2015 at the website: https://hbr.org/2011/04/building-resilience; pp. 1-15.
Slater et al., "Taking Steps: The Influence of a Walking Technique on Presence in Virtual Reality", ACM Transactions on Computer-Human Interaction, Sep. 1995, pp. 201-219, vol. 2 No. 3.
Spisak, Brian R., et al., "A face for all seasons: Searching for context-specific leadership traits and discovering a general preference for perceived health" Frontiers in Human Neuroscience; Nov. 5, 2014; available as of Dec. 13, 2015 at the web.
Sullivan 'Making the Business Case for Health and Productivity Management'—J Occup Environ Med. (JOEM) vol. 16, No. 6 suppl, dated Jun. 2004; pp. S56-S61.
The American Heritage Dictionary of the English Language, definition of planar, 2000.
The constitution of the World Health Organization, World Health Organization, WHO Chronicle, 1947, pp. 1-202.
Veeva Systems and Zinc Ahead Join Forces available as of Oct. 2, 2015 at the website: http://www.veeva.com; pp. 1-6.
Withings, The Internet connected Body Scale, retrieved with the Wayback Machine using link at www.withings.com, Jan. 11, 2010.
World Economic Forum 'The Workplace Wellness Alliance-Making the Right Investment: Employee Health and the Power of Metrics' dated Jan. 2013; pp. 1-35.
Knikou, Maria, "The H-reflex as a probe: Pathways and pitfalls" Elsevier Journal of Neuroscience Methods 171 (2008), pp. 1-12.
Duke, Sean, "A 'smartphone' based defibrillator" Science Spin, Jan. 11, 2011; pp. 1-2.
Marois, Rene, et al., "Capacity limits of information processing in the brain" Trends in Cognitive Sciences, vol. 9 No. 6 Jun. 2005, pp. 296-305.
Ivanoff, Jason, et al., "fMRI Evidence for a Dual Process Account of the Speed-Accuracy Tradeoff in Decision-Making" PLoS One 3(7): e2635. doi:10.1371/journal.p. one002635, Jul. 9, 2008; pp. 1-14.
Dux, Paul E., et al., "Traning Improves Multitasking Performance by Increasing the Speed of Information Processing in Human Prefrontal Cortex" Neuron 63, Jul. 16, 2009, Elsevier Inc.; pp. 127-138.
Dux, Paul E. and Marois, Rene, "The attentional blink: A review of data and theory" Attention, Perception & Psychophysics 2007, 71 (8); pp. 1683-1700.
Asplund, Christopher L., et al. "A central role for the lateral prefrontal cortex in goal-directed and stimulus-driven attention" Nature Neuroscience vol. 13, No. 4, Apr. 2010; pp. 507-517.
Fougnie, Daryl and Marois, Rene, "What Limits Working Memory Capacity? Evidence for Modality-Specific Sources to the Simultaneous Storage of Visual and Auditory Arrays" Journal of Experimental Psychology: Learning, Memory, and Cognition, doi: 10.1037/a0024834, Aug. 22, 2011; pp. 1-14.
Filmer, Hannah L., et al. "Disrupting Prefrontal Cortex Prevents Performance Gains from Sensory-Motor Training" The Journal of Neuroscience, Nov. 20, 2013 33(47): pp. 18654-18660.
Asplund, Christopher L., et al. "The Attentional Blink Reveals the Probabilistic Nature of Discrete Conscious Perception" Psychological Science published online Jan. 16, 2014, DOI: 10.1177/0956797613513810; pp. 1-20.
Simmonds, Bethany, et al., "Objectively Assessed Physical Activity and Subsequent Health Service Use of UK Adults Aged 70 and Over: A Four to Five Year Follow up Study" PLoS One 9(5): e97676. doi: 10.1371/journal.pone.0097676, May 2014, vol. 9, Issue 5, e97676; pp. 1-9.
Fadjo, Cameron L., et al., "Pedagogy and Curriculum for Video Game Programming Using Scratch" Institute for Learning Technologies, Teachers College, Columbia University, New York, NY, presented at the Scratch Conference Aug. 13, 2010; pp. 1-2.
Moreno, Roxana, et al., "Interactive Multimodal Learning Environments" Educ Psychol Rev (2007) 19:309-326, DOI 10.1007/510648-007-9047-2, published online Jun. 22, 2007; pp. 309-326.
Moreno, Roxana "Learning in High-Tech and Multimedia Environments" Association for Psychological Science, vol. 15-No. 2, 2006; pp. 63-67.
Fadel, Charles, et al., "Multimodal Learning Through Media: What the Research Says" Cisco Systems, Inc. 2008, pp. 1-24.
Moreno, Roxana, et al., "Cognitive Load and Learning Effects of Having Students Organize Pictures and Words in Multimedia Environments: The Role of Student Interactivity and Feedback" ETR &D, vol. 53, No. 3, 2005, ISSN 1042-1629; pp. 35-45.
Elliott, Stephen N., et al., "Cognitive Load Theory: Instruction-based Research with Applications for Designing Tests" presented at the National Association of School Psychologists' Annual Convention, Boston, MA, Feb. 24, 2009; pp. 1-22.
Wang, Xiaoning, "An Empirical Study of Optimizing Cognitive Load in Multimedia Integrated English Teaching" CS Canada Studies in Literature and Language, vol. 9, No. 3, 2014, DOI: 10.3968/6152; pp. 70-76.
Rosen, Yigal, "The effects of an animation-based on-line learning environment on transfer of knowledge and on motivation for science and technology learning" Journal of Educational Computing Research, 40(4), 2009; pp. 451-467.
Rimor, Rikki, et al., "Complexity of Social Interactions in Collaborative Learning: the Case of Online Database Environment" Interdisciplinary Journal of E-Leaming and Learning Objects, IJELLO special series of Chais Conference 2010 best papers, vol. 6, 2010; pp. 355-365.
Raybourn, Elaine M., et al., "Adaptive Thinking & Simulation Game Training for Special Forces Officers" Interservice/Industry Training, Simulation, and Education Conference (I/ITSEC) 2005; pp. 1-9.
Borah, Jack "Jake", "Conceptual Modeling—The Missing Link of Simulation Development" AEgis Technologies Group; pp. 1-7.
"Electric double-layer capacitor" Wikipedia; available at the website: http://en.wikipedia.org/wiki/Electric_double-layer_capacitor as of Dec. 5, 2014; pp. 1-8.

\* cited by examiner

SYSTEMS, COMPUTER MEDIUM AND METHODS FOR MANAGEMENT TRAINING SYSTEMS

RELATED APPLICATIONS

This application is related to U.S. patent application Ser. No. 13/540,300 filed on Jul. 2, 2012 and titled "SYSTEMS, COMPUTER MEDIUM AND COMPUTER-IMPLEMENTED METHODS FOR MONITORING HEALTH OF EMPLOYEES USING MOBILE DEVICES", U.S. patent application Ser. No. 13/540,153 filed on Jul. 2, 2012 and titled "SYSTEMS AND METHOD TO MONITOR HEALTH OF EMPLOYEE WHEN POSITIONED IN ASSOCIATION WITH A WORKSTATION", U.S. patent application Ser. No. 13/540,028 filed on Jul. 2, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. patent application Ser. No. 13/540,067 filed on Jul. 2, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,095 filed on Jul. 2, 2012 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,124 filed on Jul. 2, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,180 filed on Jul. 2, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. patent application Ser. No. 13/540,208 filed on Jul. 2, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. patent application Ser. No. 13/540,335 filed on Jul. 2, 2012 and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", U.S. patent application Ser. No. 13/540,374 filed on Jul. 2, 2012 and titled "SYSTEMS, COMPUTER MEDIUM AND COMPUTER-IMPLEMENTED METHODS FOR MONITORING HEALTH AND ERGONOMIC STATUS OF DRIVERS OF VEHICLES" (now U.S. Pat. No. 8,872,640), and/or U.S. patent application Ser. No. 13/540,262 filed on Jul. 2, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", the disclosures of which are incorporated herein by reference in their entireties.

FIELD OF THE INVENTION

The present invention relates generally to training systems and more particularly to systems, machines, non-transitory computer medium having computer program instructions stored thereon, and methods for providing training systems.

BACKGROUND OF THE INVENTION

Training systems can assist in the training of individuals. For example, Management Training Systems (MTSs) can aid users' training in the skills necessary for management and leadership. For example, such training may relate to resolving conflicts, negotiating, identifying and mitigating health and safety hazards, among other topics. Within the field of management development and training, use of technology is increasing, including the use of virtual reality simulations. Virtual reality simulations may be used by professional development trainers to provide a user with experiential training, rather than training that relies only on rote or didactic learning.

Experiential training enables users to develop leadership skills, competencies, experiences, and behaviors. During a virtual reality training session, a user may guide a digital avatar through a series of simulated scenarios and make decisions at various points during the virtual reality training session. Such virtual reality training sessions are most effective when the user is highly engaged. For this reason, post-training reviews often request that a user reports on a number of personal metrics (such as engagement, interest, etc.) to gauge the effectiveness of the virtual reality simulation.

SUMMARY OF THE INVENTION

The Applicant has recognized that self-reported and/or post-training measurements may not provide sufficient accuracy to determine the effects and efficacy of a training system. The Applicant has recognized the need for methods for providing a training systems and for determining the effectiveness of training provided through training systems.

Having recognized that, in some cases, biometrics offer a more precise gauge of user engagement during a virtual simulation than self-reports while advantageously avoiding expected population biases, embodiments of the invention include systems, methods, processor-readable media, and electronic interfaces to enhance use of virtual reality training systems by incorporating biometric feedback.

Where a conventional virtual reality simulation training method may provide a three-dimensional (3D) training environment, embodiments of the present invention can be considered to provide a four-dimensional (4-D) system using through the use of real-time, biometric feedback during the virtual simulation to better assess the user's response to the training being provided. For example, a user's engagement with the virtual simulation, as well as a variety of other information, such as the user's stress level and emotions during the virtual simulation may be recorded and used to tailor the virtual reality simulation itself, post-training actions, and/or further training. In addition to providing real-time feedback, the user's biometric feedback may be recorded and stored for later analysis, and the stored data may indicate points in time within the virtual simulation session at which the biometric data was recorded. The correlated, stored data may then be used by other users, such as a trainee's supervisor, for example, to provide recommended behavioral modification or coaching in the context of specific simulated scenarios.

Generally, a system according to an embodiment can include one or more processors and one or more input and output units in communication with the one or more processors. The one or more input and output units can further be in communication with one or more communication networks. A system can also include one or more sensors in communication with the one or more input and output units, for instance. For example, a system can include one or more heart rate sensors, one or more respiratory rate sensors, one or more skin conductivity sensors, one or more blood glucose sensors, and one or more blood pressure sensors. Further, a system can include one or more neural sensors (such as electrocephalography (EEG) sensors) in communication with the one or more input and output units. Each of the one or more EEG devices may include a plurality of EEG electrodes and be adapted to be positioned on a head of a user, for instance. A system also can include one or more facial recognition sensors in communication with the one or more input and output units. The facial recognition sensors can be positioned to capture images of physical facial features, for example. A system can still further include one or more databases in communication with the one or more processors, one or more displays in communication with the one or more processors, and non-transitory memory medium in communication with the one or more processors.

According to a first aspect described herein, there is provided a training system which includes one or more processors and one or more input and output units in communication with the one or more processors. The training system further includes one or more sensors in communication with the one or more input output units. For example, the sensors may include one or more heart rate sensors, one or more respiratory rate sensors, one or more skin conductance sensors, one or more blood glucose sensors, one or more blood pressure sensors, one or more neural sensors, and/or one or more facial recognition sensors. The facial recognition sensors may be positioned to capture images of physical facial features. The system may also include one or more displays in communication with the one or more processors, and one or more non-transitory processor-readable media in communication with the one or more processors having processor-readable instructions stored therein.

The processor-readable instructions are arranged to, when executed, cause the training system to provide a virtual reality training session and to obtain biometric data from a first user during the virtual reality training session. The obtaining may include converting measurements from the one or more heart rate sensors into electronic heart rate data. The obtaining may include converting respiratory rate measurements from the one or more respiratory rate sensors into electronic respiratory rate data. The obtaining may include converting skin conductance measurements from the one or more skin conductance sensors into electronic skin conductance data. The obtaining may include converting blood glucose measurements from the one or more blood glucose sensors into electronic blood glucose data. The obtaining may include converting blood pressure measurements from the one or more blood pressure sensors into electronic blood pressure data. The obtaining may include converting neural signals measured by the one or more neural sensors into electronic neural data. The obtaining may include converting physical facial features captured by the one or more facial recognition sensors into electronic facial data indicative of one or more of gender, age, and emotion of the first user. The obtaining may include determining a stress level of the first user responsive to analysis of at least the electronic heart rate data, the electronic respiratory rate data, the electronic skin conductance data, the electronic blood glucose data, and the electronic blood pressure data. The obtaining may include determining a level of interest, a level of engagement, a level of alertness, and a level of excitement responsive to analysis of at least the electronic neural data and the electronic facial data.

The processor-readable instructions are arranged to, when executed, cause the training system to display, in real time on the one or more displays, a first indication of one or more of the electronic heart rate data, the electronic respiratory data, the electronic skin conductance data, the electronic blood glucose data, the electronic blood pressure data, the electronic neural data, the electronic facial data, the determined stress level, and the determined levels of interest, engagement, alertness, and excitement.

The displaying step may include displaying the first indication within a virtual reality interface associated with the virtual reality training session. The virtual reality interface may be configured to include display of an avatar representing the first user. Displaying the first indication may include determining one or more graphical operation based upon at least a portion of the obtained biometric data and applying the one or more graphical operation to the displayed avatar.

The non-transitory processor-readable media may have processor-readable instructions stored therein that when executed cause the training system to monitor one or more of the one or more heart rate sensors, the one or more respiratory rate sensors, the one or more skin conductance sensors, the one or more blood glucose sensors, the one or more blood pressure sensors, the one or more neural sensors and the one or more facial recognition sensors for changes in the obtained biometric data, to determine one or more further graphical operation responsive to determining a change in the obtained biometric data and apply the one or more further graphical operation to the displayed avatar.

The non-transitory processor-readable media may have processor-readable instructions stored therein that when executed cause the training system to provide a second indication of one or more of the electronic heart rate data, the electronic respiratory data, the electronic skin conductance data, the electronic blood glucose data, the electronic blood pressure data, the electronic neural data, the electronic facial data, the determined stress level, and the determined levels of interest, engagement, alertness, and excitement to a second user.

Providing the second indication to a second user may include providing at least the second indication to the second user in real-time during the virtual reality training session.

The non-transitory processor-readable media may have processor-readable instructions stored therein that when executed cause the training system to store at least a portion of the obtained biometric data. Providing the second indication to the second user may include transmitting the stored at least a portion of the obtained biometric data to the second user for review.

The non-transitory processor-readable media may have processor-readable instructions stored therein that when executed cause the training system to generate one or more alerts responsive to obtaining the biometric data.

Providing an indication of obtained biometric data to a user may include providing the one or more alerts to the user.

The non-transitory processor-readable medium may have processor-readable instructions stored therein that when executed cause the system to monitor the obtained biometric data in real-time to determine whether one or more biometric boundary conditions are exceeded.

Generating one or more alerts may be responsive to determining that one or more biometric boundary conditions are exceeded.

Providing the virtual reality training session may include: receiving a receiving data indicating a selected training module from one of a plurality of training modules and determining biometric data required by the selected training module. Obtaining biometric data may be responsive to determining the biometric data required by the selected training module.

The non-transitory processor-readable media may have processor-readable instructions stored therein to cause the training system to provide a plurality of virtual reality training modules. For example, such training modules may include one or more of an empowerment training module, a conversations training module, a decision-making training module and a collaboration training module and wherein each of the plurality of training modules.

A virtual reality simulation of the virtual reality training session may include a plurality of paths, and the method further includes selecting one or more of the plurality of paths responsive to obtaining the biometric data. In this way, the training provided by the training system may be made more effective through dynamic adaptation in response to the biometric feedback provided by the sensors.

According to a second aspect described herein, there is provided a method of providing training in a training system. The method includes obtaining biometric data from a first user during a virtual reality training session. The obtaining may include converting measurements from one or more heart rate sensors into electronic heart rate data. The obtaining may include converting respiratory rate measurements from one or more respiratory rate sensors into electronic respiratory rate data. The obtaining may include converting skin conductance measurements from one or more skin conductance sensors into electronic skin conductance data. The obtaining may include converting blood glucose measurements from one or more blood glucose sensors into electronic blood glucose data. The obtaining may include converting blood pressure measurements from one or more blood pressure sensors into electronic blood pressure data. The obtaining may include converting neural signals measured by one or more neural sensors into electronic neural data. The obtaining may include converting physical facial features captured by one or more facial recognition sensors into electronic facial data indicative of one or more of gender, age, and emotion of the first user. The obtaining may include determining a stress level of the first user responsive to analysis of one or more of the electronic heart rate data, the electronic respiratory rate data, the electronic skin conductance data, the electronic blood glucose data, and the electronic blood pressure data. The obtaining may include determining a level of interest, a level of engagement, a level of alertness, and a level of excitement responsive to analysis of at least the electronic neural data and the electronic facial data.

The method may further include displaying, in real time on the one or more displays, a first indication of one or more of the electronic heart rate data, the electronic respiratory data, the electronic skin conductance data, the electronic blood glucose data, the electronic blood pressure data, the electronic neural data, the electronic facial data, the determined stress level, and the determined levels of interest, engagement, alertness, and excitement.

The method may include displaying an avatar representing the first user within a virtual reality interface associated with the virtual reality training session. The may also include determining on or more graphical operation based upon at least a portion of the obtained biometric data and applying the one or more graphical operation to the displayed avatar.

The method may include monitoring the one or more heart rate sensors, the one or more respiratory rate sensors, the one or more skin conductance sensors, the one or more blood glucose sensors, the one or more blood pressure sensors, the one or more neural sensors and the one or more facial recognition sensors for a change in the obtained biometric data. The method may further include determining one or more further graphical operation responsive to determining a change in the obtained biometric data and apply the one or more further graphical operation to the displayed avatar.

The method may include providing a second indication of one or more of the electronic heart rate data, the electronic respiratory data, the electronic skin conductance data, the electronic blood glucose data, the electronic blood pressure data, the electronic neural data, the electronic facial data, the determined stress level, and the determined levels of interest, engagement, alertness, and excitement to a second user.

The method may include monitoring the obtained biometric data in real-time to determine whether one or more biometric boundary conditions are exceeded. The method may include generating one or more alerts responsive to determining that one or more biometric boundary conditions are exceeded.

Providing an indication of obtained biometric data to a user may include providing the one or more alerts to the user.

According to a third aspect described herein, there is provided non-transitory processor-readable media having processor-readable instructions thereon arranged to cause a training system to carry out a method according to the second aspect.

BRIEF DESCRIPTION OF THE DRAWINGS

So that the manner in which the features and advantages of the invention may be understood in more detail, a more particular description of the invention briefly summarized above may be had by reference to embodiments thereof, which are illustrated in the appended drawings. It is to be noted, however, that the drawings illustrate only various exemplary embodiments of the invention and are therefore not to be considered limiting of the invention's scope as it may include other effective embodiments.

DETAILED DESCRIPTION

Figure 1:
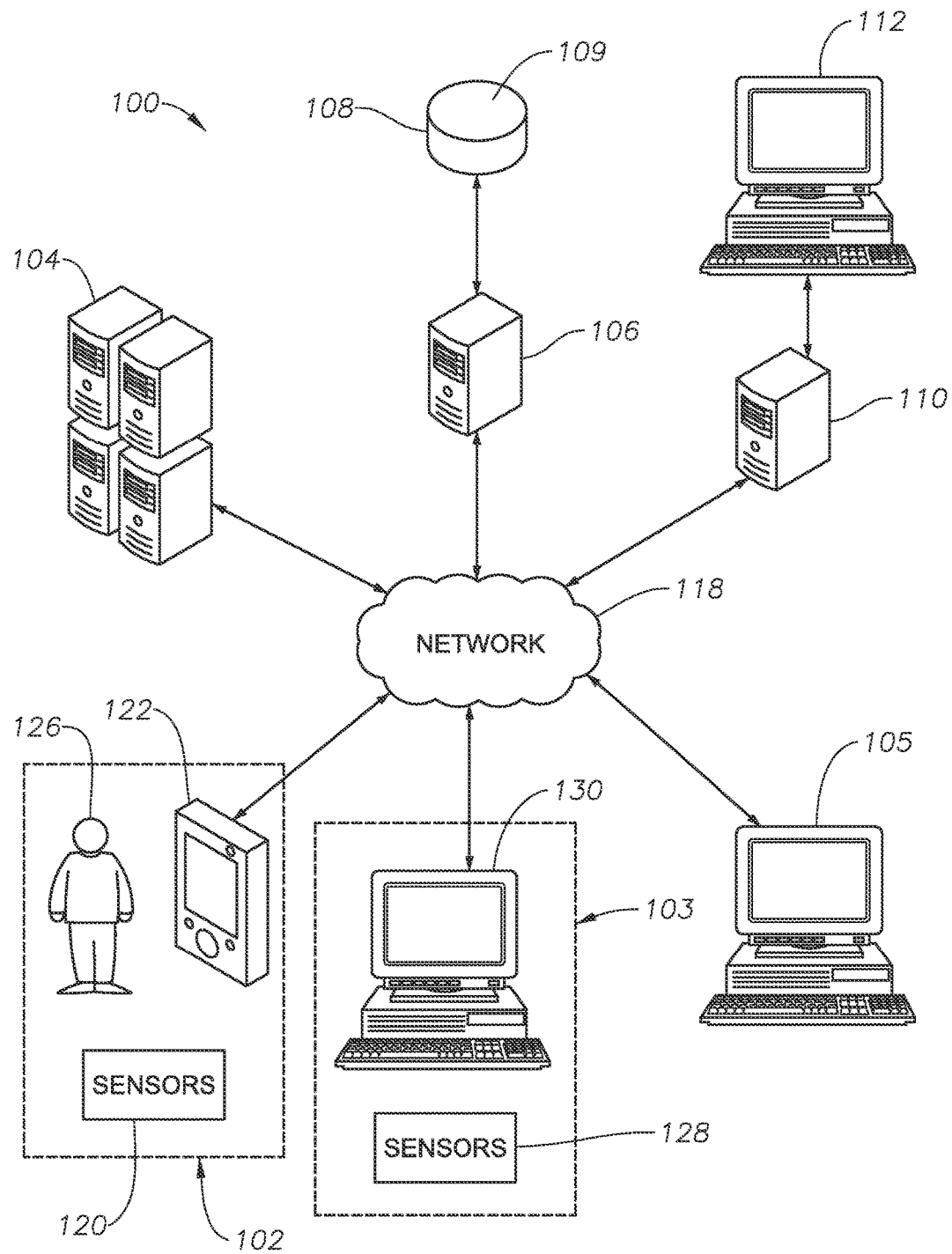
FIG. 1 is a block diagram that illustrates a network that may be used to provide a training system in accordance with one or more embodiments of the present invention.

Exemplary embodiments of the invention are now described with reference to the accompanying drawings. This invention may, however, be embodied in forms other than those shown in the drawings. As such, the invention should not be construed as limited to the illustrated embodiments described herein.

Certain embodiments provide training systems that allow real-time biometric feedback to be provided to the user during training. A training system according to some embodiments is operable to provide training by way of one or more virtual reality-based training sessions (virtual reality training sessions) with which a user interacts. During training, a plurality of the user's biometrics, for example, physiological and neurological attributes, are monitored in real-time. The monitored biometrics are used to provide feedback to the user. In some embodiments described herein, a virtual reality-based training session may present a user with a scenario that simulates a scenario that may be encountered in the "real world". For example, where the user is to perform a task in a potentially hazardous environment, a virtual reality training session may simulate the environment and hazards that may be encountered. In this way, the user may become familiar with the potential hazards which he or she may encounter before encountering those hazards.

FIG. 1 is a block diagram that illustrates an exemplary training system ("system") 100 in accordance with one more embodiments of the present invention. As depicted, training system 100 may include one or more training stations such as a mobile training station 102 and a stationary training station 103. The training stations 102, 103 may be used by one or more first users 126 of which one is depicted in FIG. 1. The first users 126 may be users that are accessing training through the training system 100. In FIG. 1 the user 126 is depicted using the training station 102, however it will be appreciated that this is merely exemplary. The training system 100 further includes one or more trainer computers, such as trainer computer 105. The trainer computer 105 may be used by second users (not shown). The second users may use the trainer computer 105 for providing, overseeing, guiding, contributing to and/or reviewing real-time and/or completed training undertaken by the first user 126 using the training system 100. It is to be understood that while referred to as trainer computers herein, the trainer computers may be used by users other than training providers, for example employers, where the first users 126 are trainees, employees or prospective employees, etc.

The depicted training system 100 further includes one or more servers 104 (of which one is depicted), one or more file servers 106 (of which one is depicted) coupled to one or more datastores 108 (of which one is depicted), and one or more web servers 110 (of which one is depicted) connected to one or more remote computers 112 (of which one is depicted). In some embodiments and as depicted, the entities of the training system 100 are communicatively coupled via a network 118. Datastore 108 may store training information 109 (including e.g., personal profile information, health profile information, collected user biometrics associated with particular training sessions, and/or the like) for one or more users.

In some embodiments, the network 118 includes an element or system that facilitates communications between entities of training system 100. For example, the network 118 may include an electronic communications network, such as the Internet, a local area network ("LAN"), a wide area ("WAN"), a wireless local area network ("WLAN") a cellular communications network or the like. In some embodiments, the network 118 includes a single network or combination of networks. For example, the training stations 102, 103, the trainer computer 105, the server 104, the file server 106, and/or the web server 110, may be networked using a private/LAN, with the remote computers 112 (e.g., user home computers, external service provider computers and/or the like) connected to the web server 110 via a WAN.

As described in more detail below, the training stations 102, 103 may include sensors 120, 128 for monitoring and collecting user data for use during and after a training session. In some embodiments, the collected data may include data that can be used to assess various biometrics (e.g. physiological, neurological, etc.) of the user. By way of example, the collected data may include one or more of heart rate, respiratory rate, skin conductance, blood glucose, electrical activity (e.g. brain and nerve activity), blood pressure, and facial features (e.g. shapes, positions, sizes, etc.). It is to be understood that while the following description is particularly concerned with the aforementioned collected data, the sensors 120, 128 may include sensors for monitoring and collecting data relating to other user biometrics, including but not limited to body temperature, body weight, body fat, blood oxygen saturation (e.g., blood oxygenation), and/or the like. It is to be understood that the term "biometric sensors" is used herein to refer to both sensors that are used to acquire measurements relating to any one or more of neurological, emotional, electrical, biomechanical, behavioral, etc. attributes of a user.

As discussed in more detail below, the training stations 102, 103 may further include user computers, such as the computer 130 of the training station 103 and the user computer 122 of the training station 102. The computers 122, 130 may be operable to receive biometric data from the various sensors 120, 128 and to use the received biometric data in the provision of training feedback and/or to forward received data to the server 104 for use in provision of training feedback. For example, in response to determining that biometric data needs to be collected (e.g., based on a request from the server 104, based on a request from a user, a predetermined training schedule, and/or the like), the computer 122 may monitor sensors 120 to collect data (e.g., measurements) from the sensors 120, and forward the data to server 104 for use in monitoring the user's biometrics during a training simulation.

Although certain embodiments are described herein with regard to the computers 122, 130 forwarding biometric data to the server 104, it will be appreciated that in other embodiments, some or all of the biometric data is provided directly to the server 104 (i.e., without having to pass the data through the user computer 130). For example, the sensors 120 may be communicatively coupled to the server 104 via the network 118 (e.g., via a WLAN) such that they can transmit biometric data directly to the server 104. In other embodiments, data is not passed to the server 104, for example, where training and feedback is provided through a "standalone" training station.

Figure 2:
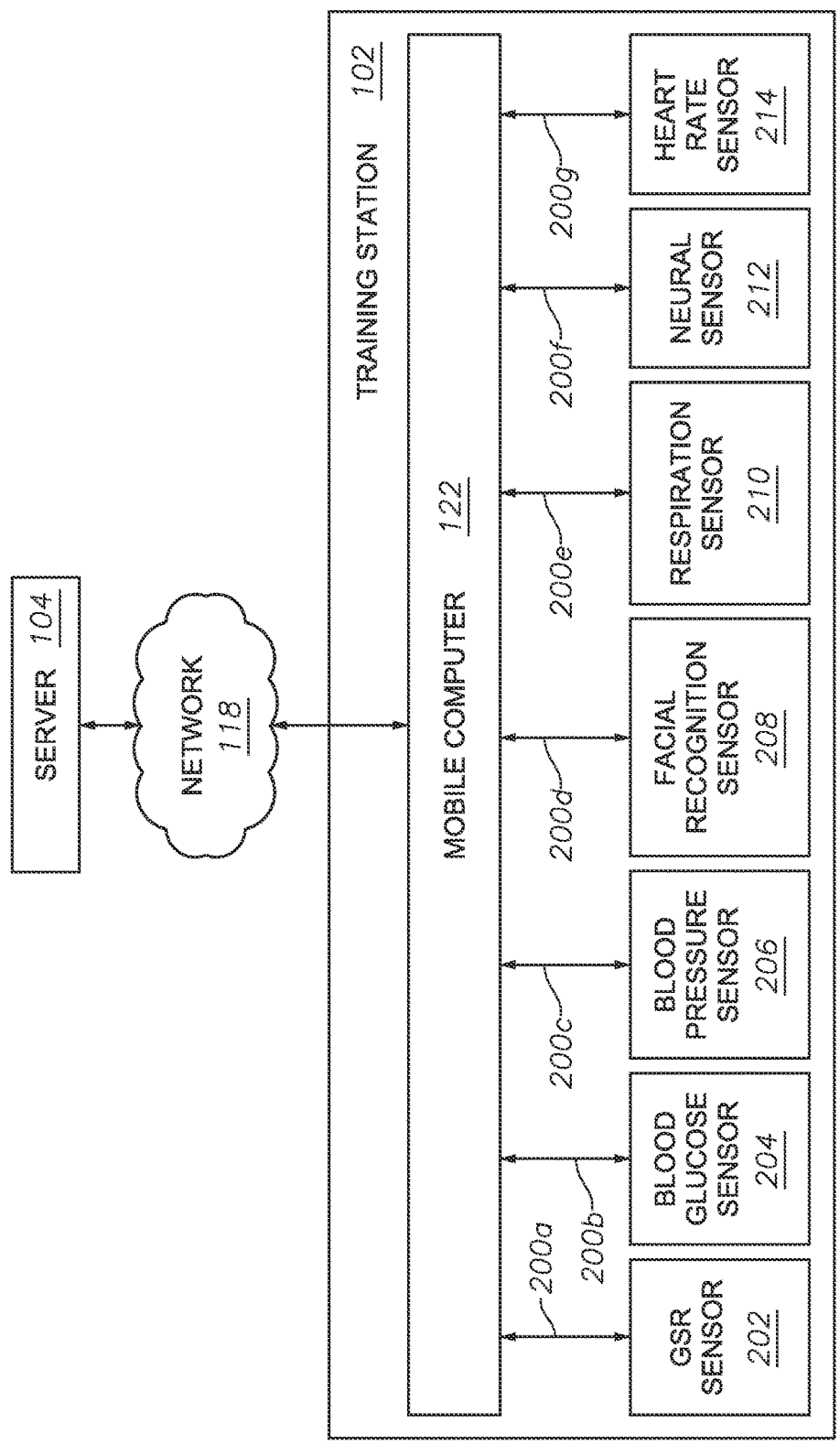
FIG. 2 is a block diagram that illustrates a training system training station connected to a server in accordance with one or more embodiments of the present invention.

FIG. 2 is a block diagram that schematically illustrates the training station 102 connected to the server 104 via the network 118 in accordance with one or more exemplary embodiments. In some embodiments the training station 102 includes the user computer 122 communicatively coupled to the one or more sensors 120 for taking measurements to provide biometric data 200. For example, the training station 102 may be communicatively coupled to one or more skin conductance (sometimes referred to as galvanic skin response (GSR)) sensors 202, one or more blood glucose sensors 204, one or more blood pressure sensors (e.g., a blood pressure cuff) 206, one or more facial recognition sensors 208, one or more respiration sensors 210, one or more neural sensors 212 and one or more heart rate sensors 214 (e.g., a heart rate monitor). Measurements taken from the sensors are converted into electronic biometric data 200 for use by the training system 100. For example, in the arrangement of FIG. 2, measurements taken by the skin conductance sensor 202 are converted into electronic skin conductance data 200a, measurements taken by the blood glucose sensor 204 are converted into electronic blood glucose data 200b, measurements taken by the blood pressure sensor 206 are converted into electronic blood pressure data 200c, measurements taken by the facial recognition sensor 208 are converted into electronic facial recognition data 200d, measurements taken by the respiration sensor 210 are converted into electronic respiratory rate data 200e, measurements taken by the neural sensor 212 are converted into electronic neural data 200f (including, for example, data indicative of one or more brain signals such as alpha, beta, delta, gamma, etc.), and measurements taken by the heart rate sensor 214 are converted into electronic heart rate data 200g. Measurements taken by respective sensors 120 may be converted into electronic biometric data by the sensor itself, by the user computer 122, or by another entity within the training system 100.

The sensors 120 may include other arrangements and may not necessarily contain all of the sensors indicated in FIG. 2. Additionally, the sensors 120 may include sensors other than those depicted in FIG. 2. By way of example only, the sensors 120 may further include one or more temperature sensors (e.g., thermocouples, IR sensors, etc.), one or more blood condition sensors (e.g., pulse oximeters), one or more force sensors (e.g., force transducers), one or more body fat sensors (e.g., conductive contacts), one or more body position sensors (e.g., three-dimensional ("3D") image/video camera), one or more audio sensors (e.g., microphone) and/or the like for collecting biometric data.

In some embodiments, the user computer 122 may be communicatively coupled to the sensors 120 via a wired connection. For example, some or all of the sensors 120 may include a communication cable extending between each of the respective sensors 120 and the user computer 122. In some embodiments, the user computer 122 may be communicatively coupled to the sensors 120 via a wireless connection. For example, some or all of the sensors 120 may communicate with the user computer 122 via a wireless connection (e.g., a Bluetooth connection, a WLAN of network 118, and/or the like). In some embodiments, biometric data 200 (e.g., 200a-200g) may be transmitted from the sensors 120 to the user computer 122 via the wired or wireless connection. In some embodiments, some of the biometric data 200 may be transferred between devices of training system 100 via a non-transitory storage medium such as a universal serial bus ("USB") memory stick (e.g., a flash drive). For example, the biometric data 200 acquired from the sensors 120 may be downloaded from the sensors 120 and/or the user computer 122 to a USB memory stick and may be uploaded from the USB memory stick to another device of training system 100, such as the user computer 122, the trainer computer 105, the file server 106, the remote workstation 112, and/or the sever 104.

Figure 3:
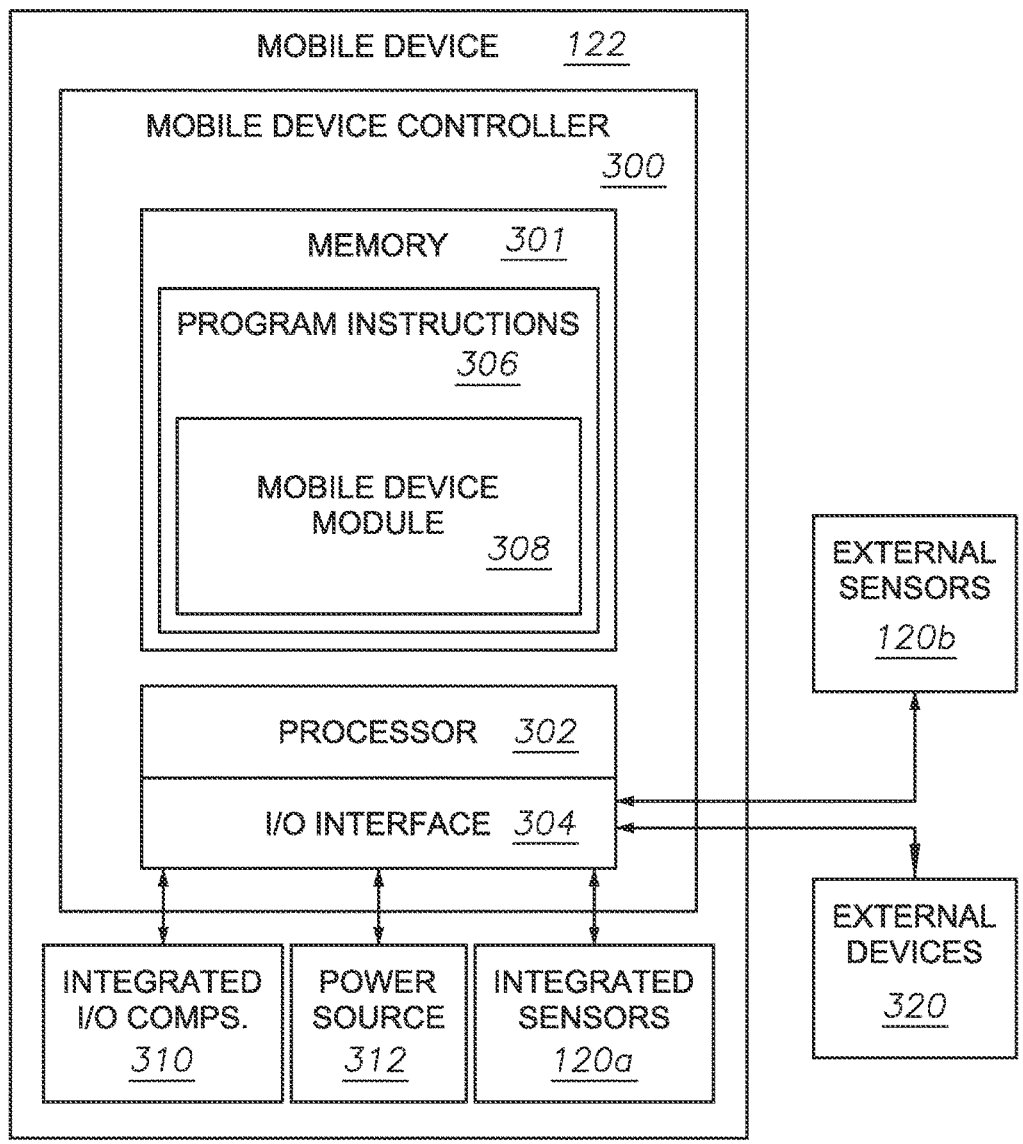
FIG. 3 is a block diagram that illustrates components of a training system training station in accordance with one or more embodiments of the present invention.

FIG. 3 is a block diagram that schematically illustrates components of the user computer 122 in accordance with one or more embodiments of the present invention. In some embodiments, the user computer 122 includes a mobile device controller 300 for controlling the operational aspects of the user computer 122. For example, the mobile device controller 300 may provide for allocating power to integrated devices, collecting biometric data 200 from the various sensors 120 and/or transmitting the collected biometric data 200 to the server 104. In some embodiments, the mobile device controller includes a memory 301, a processor 302 and an input/output (I/O) interface 304.

The memory 301 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 301 may include a non-transitory processor-readable storage medium having program instructions 306 stored thereon that are executable by a computer processor (e.g., the processor 304) to cause the functional operations (e.g., methods/routines/processes) described herein with regard to the user computer 122. The program instructions 306 may include a mobile device module 308 including program instructions that are executable by the processor 302 to provide some or all of the functionality described herein with regard to the user computer 122.

The processor 302 may be any suitable processor capable of executing/performing program instructions. The processor 302 may include a central processing unit (CPU) that carries out program instructions (e.g., of the mobile device module 308) to perform arithmetical, logical, and input/output operations of the user computer 122, including those described herein.

The I/O interface 304 may provide an interface for connection of one or more I/O devices to the user computer 122. I/O devices may include integrated I/O components (e.g., buttons, microphone, speaker, graphical display (e.g., a touch screen), cameras, and/or the like) 310, a power source 312 (such as a battery), integrated sensors 120a, external devices 320 (including, for example, external display devices, the server 104), and/or the like. The integrated I/O components 310 and/or the external devices 320 facilitate interaction by the user with a training session provided on the training station 102. For example, as will be described in more detail below, visuals may be displayed on a graphical display (e.g. of the training station 102 or an external device) to illustrate scenarios to which the user must respond. Keypads, touchscreens, microphones, buttons, etc. may be provided to allow the user to respond to scenarios presented to the user during a training session simulation.

The external devices 320 may be connected to I/O interface 304 via a wired or wireless connection. For example, the external devices 320 may be connected to the I/O interface via wireless connection to the network 118. In some embodiments, the integrated sensors 120a include sensors 120 that are physically integrated with the user computer 122. For example, as described in more detail below, the integrated sensors 120a may include conductive contacts integrated into the exterior of the user computer 122 such that a measurement (e.g., temperature measurement, a skin conductance measurement, and/or the like) can be acquired via the conductive contacts while the user is grasping the exterior of the user computer 122. In some embodiments, the external sensors 120b include the sensors 120 that are remote from the user computer 122. For example, external sensors 120b may include facial recognition sensors 208, blood pressure sensors 206, respiratory sensors 206, or the like that are worn by the user to take measurements at various locations on the user's body. It is to be understood that any of the sensors 120 may be integrated sensors 120a or external sensors 120b.

The user computer 122 may be employed to collect biometric data 200 from the various sensors 120 (e.g., integrated sensors 120a and/or external sensors 120b) and/or forward corresponding biometric data 200 to the server 104 for use in monitoring the user's biometrics. For example, in response to determining that biometric data 200 (e.g., skin conductance data, blood glucose data, blood pressure data, facial recognition data, respiration data, electronic neural data 200f and/or heart rate data) needs to be collected (e.g. upon initialization of, or preparation for, a training simulation), the user computer 122 may employ, or otherwise monitor, one or more of the particular sensors 120 capable of sensing/measuring the needed biometric data 200. The user computer 122 may collect/store the biometric data 200 (e.g., store/queue the acquired biometric data 200 in memory 301), and/or the user computer 122 may forward the biometric data 200 to another entity in the training system 100 (such as the server 104) for use in monitoring the user's biometric state.

In some embodiments, the user computer 122 may process the raw/acquired biometric data to generate corresponding processed biometric data. For example, where the user computer 122 receives raw biometric data (e.g., electronic skin conductance data 200a including a current indicative of a sensed skin conductance), the user computer 122 may process the raw biometric data to generate a corresponding value (e.g., using a look-up table, equation, and/or the like to identify a skin conductance value corresponding to the current) that may be included in any biometric data 200 transmitted to other entities of the training system 100 (such as the server 104). Accordingly, in some embodiments, the biometric data 200 may include the raw/acquired biometric data (e.g., a current value) and/or the processed biometric data corresponding thereto (e.g., the skin conductance value corresponding to the voltage value). Similar processing may be provided for the other types of biometric data.

In some embodiments, the user computer 122 may forward the biometric data 200 as the corresponding biometric data is received. For example, the user computer 122 may receive biometric data 200 from sensors 120 and immediately forward the biometric data 200 with little to no delay such that a continuous stream of biometric data 200 is provided to the server 104 for use in monitoring the user's biometrics. In some embodiments, the user computer 122 may store (e.g., queue or buffer) at least some of the biometric data 200 for transmission at a later time. For example, where a training simulation requires that the user computer 122 transmit a batch of biometric data 200 at the end of the training simulation, transmit a batch of biometric data 200 at a regular interval (e.g., every ten minutes), or the like, the biometric data 200 received may be stored in memory 301 of the user computer 122 and may be queued-up or buffered in memory local to the user computer 122 for transmission, as a batch of biometric data 200, to server 104 at the end of the training simulation, at the regular interval, or the like as required.

In some embodiments, a skin conductance sensor 202 may include any suitable skin conductance sensor. During use, the skin conductance sensor may transmit biometric data 200 indicative of a conductance sensed by the skin conductance sensor 202. For example, where a skin conductance sensor 202 is positioned to acquire a user's skin conductance at a given location (e.g., a user's fingertips, wrist, etc.), the user computer 122 may receive, from the skin conductance sensor 202, the electronic skin conductance data 200a indicative of the skin conductance at the given location. Skin conductance is effected by an amount of sweat that produced by a user, which is governed by the sympathetic nervous system in response to stimuli. As such, the skin conductance measurement may be used in the determination of an emotional state of the user. For example, the electronic skin conductance data 200a may be used in determining a stress level indicating a level of stress experienced by the user.

In some embodiments, the blood glucose sensor 204 may include any suitable blood glucose sensor. For example, the blood glucose sensor 204 may include one or both of a lancet/glucose-meter sensor system and a continuous blood-glucose monitoring sensor system (e.g. an embedded system). The blood glucose sensor 204 may further or alternatively include non-invasive blood glucose monitoring sensors using, for example, infrared, ultrasound, etc. to monitor a blood glucose level of a user. In some embodiments, a blood glucose sensor may use photonic glucose crystal sensing/photoplethysomography to detect blood glucose as will be understood by those skilled in the art. During use, the user computer 122 may receive biometric data 200 indicative of blood characteristics sensed by the blood glucose sensor 204. For example, where a lancet is used to draw blood from a user's fingertip, the blood may be provided to a glucose meter. The user computer 122 may receive, from the glucose meter, electronic blood glucose data 200b indicative of the level of glucose in the user's blood. As blood glucose may be effected by stress, the electronic blood glucose data 200b may be used in determining an emotional state of the user. For example, the electronic blood glucose data 200b may be used in determining a stress level indicating a level of stress experienced by the user.

In some embodiments, a blood pressure sensor 206 may include blood pressure cuffs and/or the like. By way of example only, the blood pressure sensor 206 may include the UA-789PC Extra Large Cuff sold by LifeSource™, the CMS-08A Professional Upper Arm Blood Pressure Monitor manufactured by CMS™, or similar. During use, the user computer 122 may receive biometric data 200 indicative of the user's blood pressure sensed by the blood pressure sensor 206. For example, where a blood pressure cuff is positioned about the user's wrist/arm, the user computer 122, may receive, from the blood pressure cuff, electronic blood pressure data 200c indicative of the user' blood pressure sensed at the user's wrist/arm.

In some embodiments, a facial recognition sensor 208 may include image sensors (such as cameras) operable to record images of a user's face during a training simulation, in combination with facial recognition processing. For example, in some embodiments the facial recognition sensor 208 may utilize the SHORE™ system from Fraunhofer IIS to detect faces in images captured by an image sensor. In some embodiments, the facial recognition processing may be performed on the user computer 122, or may be performed by a processor integral with the facial recognition sensor 208. Alternatively, the facial recognition processing may be performed by another entity within the training system 100. In some embodiments, therefore, the facial recognition sensor 206 may include a plurality of distributed components, including, for example, the user computer 122. In some embodiments, during use, the user computer 122 may the received electronic facial recognition data 200d (using, for example, the SHORE™ system) to determine one or more of a gender, age, and emotion of a user.

In some embodiments, respiration sensor 210 may include a device for sensing the user's respiration rate (e.g., number of breaths taken within a set amount of time, typically sixty seconds). During use, the user computer 122 may receive biometric data 200 indicative of the respiration rate ("RR") of the user sensed by the respiration sensor 210. For example, the user computer 122 may receive, from the respiration sensor 210, electronic respiratory rate data 200e indicative of number of breaths taken by the user over sixty seconds.

In some embodiments, neural sensor 212 may include a device (e.g., an electrode) for sensing neural activity (e.g., brain activity) of the user. In some embodiments, the neural sensors 212 may employ electroencephalography ("EEG") to measure neuro-signal voltage fluctuations resulting from ionic current flows within the neurons of the brain. EEG may refer to recording of the brain's spontaneous electrical activity over a short period of time (e.g., twenty-forty minutes) from a plurality of neural sensors 212 disposed on the user's scalp. For example, the neural sensor 212 may include a plurality of electrodes (e.g., sixteen neural sensors/channels) to be disposed about the user's scalp to detect neuro-signals (e.g., such as alpha, beta, gamma, and delta waves) that can be used to determine information relating to, for example, the user's emotional state (e.g., happy, sad, excited, etc.), the user's thoughts (e.g., cognitive thoughts, subconscious thoughts, intent, etc.), the user's facial movements (e.g., facial expressions), motor functions and/or the like. During use, the user computer 122 may receive biometric data 200 indicative of the user's neural activity sensed by the neural sensor 212. For example, the user computer 122 may receive, from the neural sensor 212, electronic neural data 200f indicative of the sensed neuro-signals.

In some embodiments, a heart rate sensor 214 may include a heart rate monitor. During use, the user computer 122 may receive biometric data 200 indicative of the user's heart rate sensed by the heart rate sensor 214. For example, where a heart rate monitor is positioned about the user's torso, the user computer 122 may receive, from the heart rate monitor, electronic heart rate data 200g indicative of the user's hear rate (e.g., 80 beats per minute ("BPM")).

In some embodiments, some or all of the sensors 120 may be located at or near the user 126 (e.g., worn by the user) and/or physically integrated with the user computer 122. For example, various ones of the sensors 120 may be provided in the user's apparel, such as their clothing (e.g., shirt and pants, gloves, etc.), footwear (e.g., work boots), head wear (e.g., a safety helmet), and eyewear (e.g., safety glasses) and/or various ones of the sensors 120 may be located in the user computer 122. In some embodiments one or more of the sensors may be provided by a multi-sensing device worn by the user. For example, in some embodiments, the skin conductance sensor 202, respiratory sensor 210, and the heart rate sensor 214 may include a Basis™, or a Basis Peak™ wrist-worn tracking device from Basis Science Inc. In some embodiments, the neural sensor 212 may include an Emotiv EPOC or EPOC+ from Emotiv Systems Inc.

Figure 4:
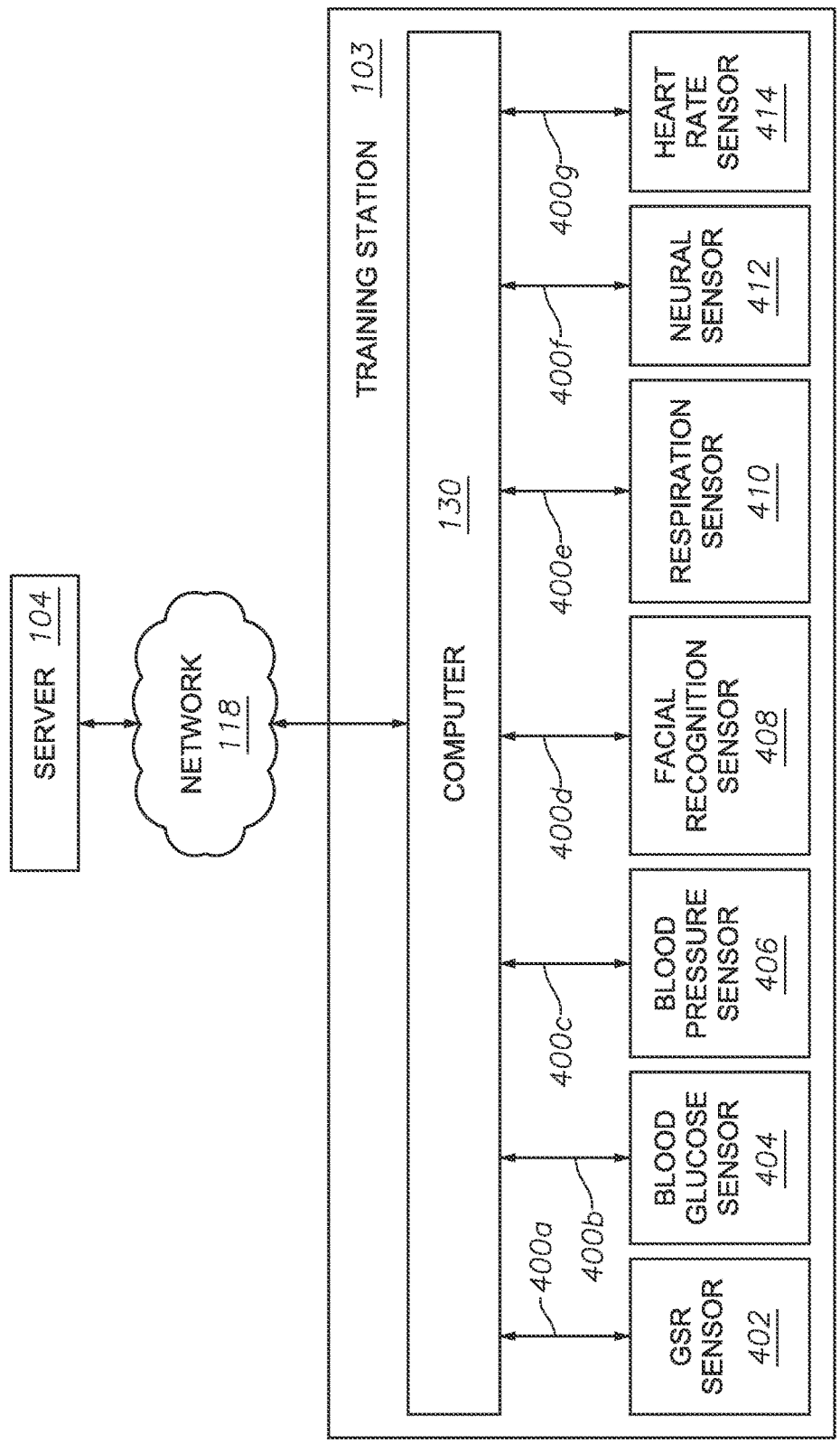
FIG. 4 is a diagram that illustrates an exemplary training system training station in accordance with one or more embodiments of the present invention.

The training station 103 may be arranged similarly to the training station 102. FIG. 4 is a block diagram that illustrates the training station 103 connected to the server 104 in accordance with one or more embodiments of the present invention. In some embodiments the training station 103 includes the training station 103 communicatively coupled to one or more of the sensors 128 for collecting biometric data 400. For example, the training station 103 may be communicatively coupled to one or more skin conductance sensors (e.g. galvanic skin response sensors) 402, one or more blood glucose sensors 404, one or more blood pressure sensors (e.g., a blood pressure cuff) 406, one or more facial recognition sensors 408, one or more respiration sensors 410, one or more neural sensors 412 and one or more heart rate sensors 414 (e.g., a heart rate monitor). In the arrangement of FIG. 4, the biometric data 400 includes electronic skin conductance data 400a, electronic blood glucose data 400b, electronic blood pressure data 400c, electronic facial recognition data 400d, electronic respiratory rate data 400e, electronic neural data 400f (including, for example, alpha, beta, delta, gamma and theta brain signals), and electronic heart rate data 400g, collected from the corresponding sensors 128.

The sensors 128 may include other arrangements and may not necessarily contain all of the sensors indicated in FIG. 4. Additionally, the sensors 128 may include sensors other than those depicted in FIG. 4. By way of example only, the sensors 128 may further include one or more temperature sensors (e.g., thermocouples, IR sensors, etc.), one or more blood condition sensors (e.g., pulse oximeters), one or more force sensors (e.g., force transducers), one or more body fat sensors (e.g., conductive contacts), one or more body position sensors (e.g., three-dimensional ("3D") image/video camera), one or more audio sensors (e.g., microphone) and/or the like for collecting biometric data.

In some embodiments, the training station 103 is communicatively coupled to the sensors 128 via a wired connection. For example, some or all of the sensors 128 may include a communication cable extending between the respective sensor 128 and the training station 103. In some embodiments, training station 103 is communicatively coupled to the sensors 128 via a wireless connection. For example, some or all of the sensors 128 may communicate with the training station 103 via a wireless connection (e.g., a Bluetooth connection, a wireless connection to a WLAN of network 118, and/or the like). In some embodiments, the biometric data 400 is transmitted from the sensors 128 to the training station 103 via the wired or wireless connection (e.g., a Bluetooth connection, a WLAN of network 118, and/or the like). In some embodiments, the biometric data 400 is transferred between devices of the training system 100 via a physical memory medium such as a universal serial bus ("USB") memory stick (e.g., a flash drive). For example, the biometric data 400 acquired from the sensors 128 may be downloaded from the sensors 128 and/or the training station 103 to a USB memory stick and may be uploaded from the USB memory stick to another device of the training system 100, such as the training station 103, the trainer computer 105, and/or the sever 104.

The sensors 128 may be provided by any configuration of suitable sensors, and may, by way of example, be as described above with reference to the sensors 120 of the training station 102. For example, in some embodiments one or more of the sensors 128 may include a multi-sensing device worn by the user. For example, in some embodiments, the skin conductance sensor 402, respiratory sensor 410, and the heart rate sensor 414 may include a Basis™, or a Basis Peak™ wrist-worn tracking device from Basis Science Inc., or other similar biometric tracking device. In some embodiments, the neural sensor may include an Emotiv EPOC or EPOC+ from Emotiv Systems Inc., or similar.

Figure 5:
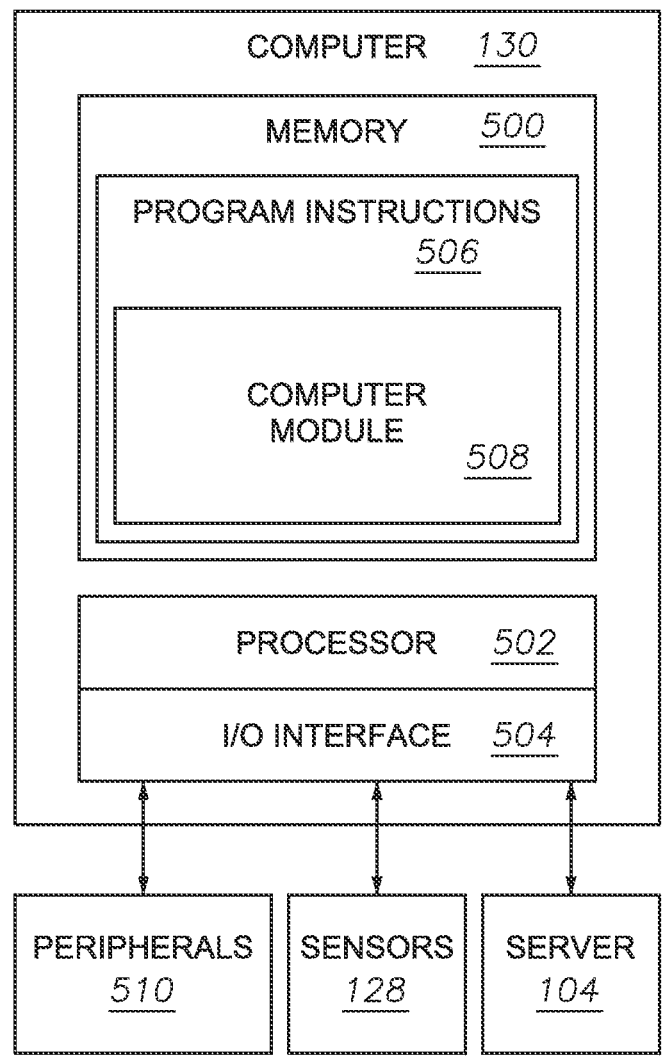
FIG. 5 is a block diagram that illustrates a training system training station in accordance with one or more embodiments of the present invention.

FIG. 5 is a block diagram that illustrates components of the user computer 130 in accordance with one or more embodiments of the present invention. In some embodiments, the user computer 130 includes a memory 500, a processor 502 and an input/output (I/O) interface 504.

The memory 500 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 500 may include a non-transitory processor-readable storage medium having program instructions 506 stored thereon that are executable by a computer processor (e.g., the processor 502) to cause the functional operations (e.g., methods/routines/processes) described herein with regard to the user computer 130. The program instructions 506 may include a computer module 508 including program instructions that are executable by the processor 502 to provide some or all of the functionality described herein with regard to the user computer 130.

The processor 502 may be any suitable processor capable of executing/performing program instructions. The processor 502 may include a central processing unit (CPU) that carries out program instructions (e.g., program instruction of the computer module 508) to perform arithmetical, logical, and input/output operations of the user computer 130, including those described herein.

The I/O interface 504 may provide an interface for connection of one or more I/O devices to the user computer 530. I/O devices may include peripherals 510, the sensors 128, the server 104, and/or the like. The peripherals 510 may include, for example, graphical user interface displays (e.g., a virtual reality headset, a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, and/or the like. The I/O devices (e.g., the peripherals 510, the sensors 128, and the server 104) may be connected to the I/O interface 504 via a wired or wireless connection. The peripherals 510 facilitate interaction by the user with a training session provided on the training station 103. For example, as will be described in more detail below, visuals may be displayed on a display device to illustrate scenarios to which the user must respond. Keyboards, touchpads, mice, etc. may be provided to allow the user to respond to scenarios presented as part of a training session.

The user computer 130 may be employed to collect the biometric data 400 from the various sensors 128 and/or forward corresponding biometric data 400 to the server 104 for use during or after a training session. For example, in response to determining that biometric data 400 needs to be collected, the user computer 130 may employ one or more of the sensors 128 capable of sensing/acquiring the needed biometric data 400 to acquire the needed biometric data 400. The user computer 130 may collect/store the acquired biometric data 400 (e.g., store/queue the acquired biometric data 200 in the memory 500), may process the biometric data 400 (e.g. for use in providing training) and may forward the acquired biometric data 400 to the server 104 for use in monitoring the user's biometric state during a training session.

As described above with reference to the user computer 122, the user computer 130 may process raw/acquired biometric data 400 to generate the corresponding processed biometric data 400. Indeed, it is to be understood that the acquisition of user biometric data 400 from the training station 103 may be implemented in any appropriate way and may be generally equivalent to the described acquisition of biometric data 200 from the user station 102.

Figure 6:
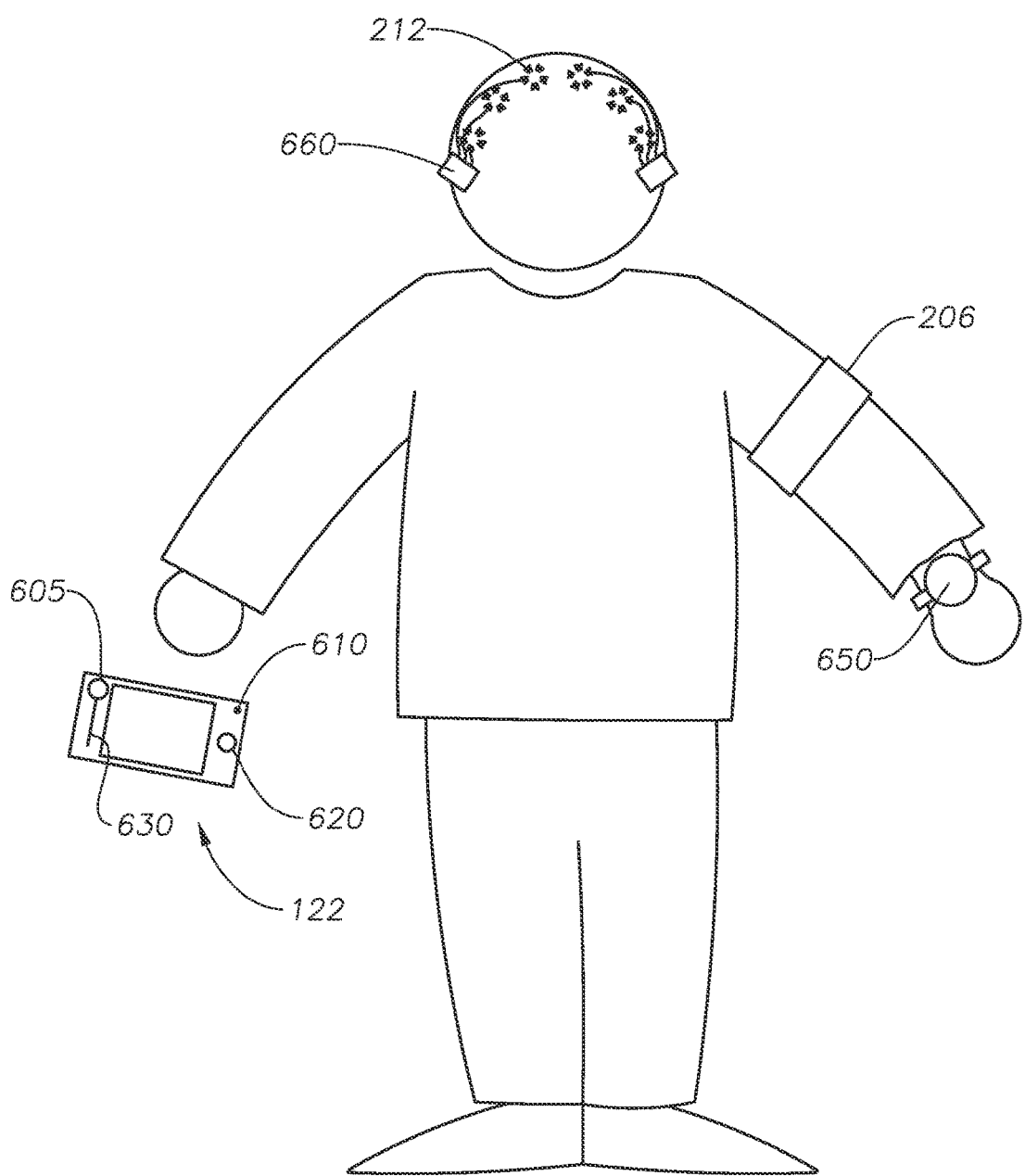
FIG. 6 illustrates a user wearing various sensors of the training station of FIG. 2 in accordance with one or more embodiments of the present invention.

In some embodiments, some or all of the sensors 120, 128 may be located throughout the user's environment on and surrounding the training stations 102, 103. For example, various ones of the sensors 128 may be located at or near the user's desk, chair, computer, or the like, while various ones of the sensors 120 may be integrated into the user computer 122 or be arranged for placement around an area in which the user computer 122 is intended for use. FIG. 6 is a diagram that illustrates the user 126 wearing various of the sensors 120 of the mobile training station 102 in accordance with one or more embodiments of the present invention. The user 126 holds the user computer 122. In some embodiments, the mobile user computer 122 includes a screen 610, which may be a touchscreen to allow the user to both view and interact with a virtual reality simulation. In some embodiments, a separate screen (not shown) may be provided which is in communication (e.g. wired or wireless) with the mobile user computer 122 for use instead or in combination with an integrated screen (where an integrated screen is provided). For example, in some embodiments, visuals of a virtual reality simulation may be provided on an external screen (for example, an LCD screen, a virtual reality headset, etc.), while the integrated touchscreen 610 is utilized for user input for interaction with the virtual reality simulation. In some embodiments, the mobile user computer 122 includes one or more buttons 620 to allow the user 126 to provide inputs to the mobile user computer 122, such as for interaction with a provided virtual reality simulation.

In some embodiments of the user computer 122, the facial recognition sensor 208 is provided in the form of an integrated camera 605. In some embodiments, the integrated camera 605 of the mobile computer 122 may include a two-dimensional still/video camera, a three-dimensional ("3D") still/video camera and/or the like that includes all or part of the facial recognition sensor 208. For example, the camera 605 may be used to acquire images of the face of the user 126 and provide those images for processing on the user computer 122 to generate the electronic facial recognition data 200d. In some embodiments, an external camera is provided instead of or in addition to the integrated camera 605.

In some embodiments, the user computer 122 includes an integrated speaker 630, which may be used in the provision of sound components of a virtual reality simulation and/or instructions from a second user (e.g., a training provider/overseer, etc.). In some embodiments, an external speaker may be provided instead of or in addition to the integrated speaker 630. In some embodiments, the user computer 122 includes an integrated microphone 640 which may be employed as an audio sensor. For example, the microphone 640 may be used to acquire audio data (e.g., words spoken by the user 126). In this way, for example, the user 126 may interact with a virtual reality simulation and/or a second user (e.g., a training provider/overseer, etc.) using audio input. In some embodiments, an external microphone may be provided in addition to or instead of the integrated microphone 640.

In some embodiments, a multi-sensor device 650 is provided. In the depicted embodiment, the multi-sensor device 650 is worn around the wrist of the user 126. For example, as described above, a multi-sensor device such as the Basis® or Basis Peak® from Basis Science Inc. may be provided. Additionally or alternatively, any other multi-sensor devices may be utilized, such as chest mounted multi-sensor devices. The multi-sensor device 650 may provide a plurality of the sensors 120 in a convenient and compact arrangement. For example, the multi-sensor device 650 may provide the skin conductance sensor 202, the respiration sensor 210 and the heart rate sensor 214. It will be appreciated, however, that the multi-sensor device 650 may provide any number of the sensors 120 and/or additional sensors. In other embodiments, a plurality of multi-sensor devices may be provided. Such an integration of a plurality of the sensors 120 within one or more multi-sensor devices, and within the training station environment may help to reduce the physical profile of the sensors 120, reduce distractions to the user 126 that may otherwise be caused by the presence of the sensors 120 and/or enhance the ease of use of the training station 102 to the user 126 by allowing the biometric data 200 to be acquired while the user 126 is engaging in the training session. For example, at least some of the sensors 120 may be able to passively acquire biometric data 200 without requiring the user to take special efforts to facilitate the acquisition of the biometric data 200. It will be apparent to one skilled in the art, however, that the sensors 120, 128 may be implemented in any appropriate manner and need not be provided in a multi-sensor device.

In some embodiments, a blood glucose sensor 204 is disposed at the user's finger. For example, the blood glucose sensor 204 may include a lancet for extracting a small sample of blood from a finger of the user 216 coupled with a glucose meter disposed about the user's body or within the surrounding area of the mobile training station 102. Other embodiments may include any number of blood glucose sensors provided in any suitable configuration and any number of suitable locations such as the user's earlobe, toe and/or the like. In some embodiments, other types of blood glucose sensor may be provided for use instead of or in addition to the depicted blood glucose sensor. For example, an infrared sensor (not shown) may be used to provide a blood glucose sensor. In some embodiments, a passive blood glucose sensor may be used in combination with the depicted lancet-based blood glucose sensor. For example, an initial reading may be provided using the lancet-based blood glucose sensor to calibrate a passive blood glucose sensor prior to initializing a training session, with in-training blood glucose measurements being taken by a passive blood glucose sensor.

In some embodiments, a blood pressure sensor 206 is disposed at the user's arm/wrist. For example, the blood pressure sensor 206 may include a blood pressure cuff 410 secured about the user's wrist. In some embodiments, the blood pressure cuff 410 may be integrated into a sleeve of the user's shirt. Other embodiments may include any number of blood pressure sensors provided in any number of suitable locations such as the user's upper-arm and/or the like.

In some embodiments, one or more neural sensors 212 are disposed about the user's head/scalp on a neuro-headset 660. In some embodiments, the neuro-headset 660 includes a plurality of neural sensors 212 (e.g., sixteen neural sensors 212) integrated therein. The neuro-headset 660 may provide for positioning of the neural sensors 212 in discrete neural sensor locations about the user's head. Where the display screen 610 includes a virtual reality headset, the neuro-headset 660 may from a part of the virtual reality headset. That is, in some embodiments, both the neuro-headset 660 and a display screen 610 in the form of a virtual reality headset may be provided in an integrated unit.

Figure 7:
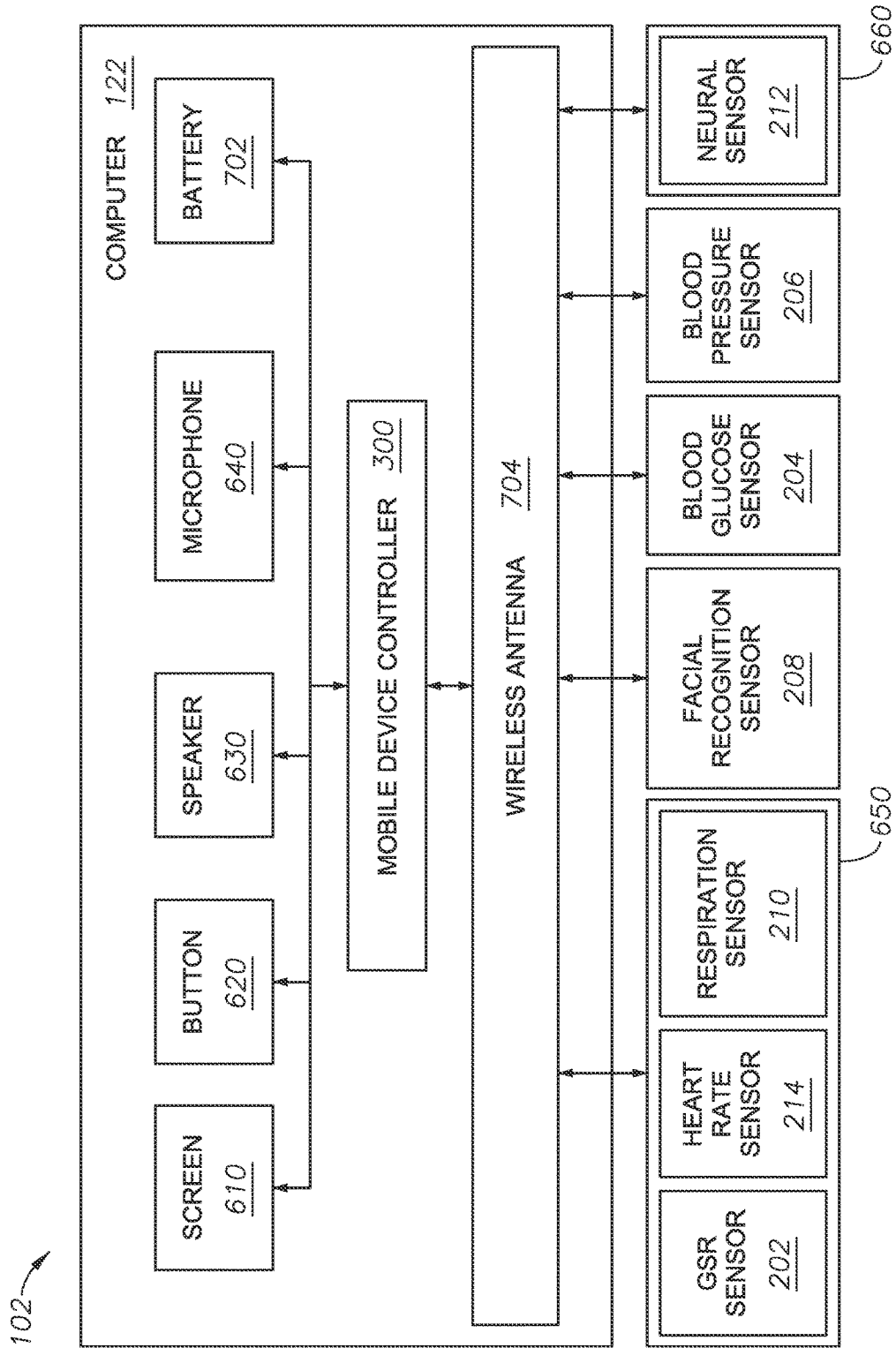
FIG. 7 is a block diagram that illustrates a training system training station including a multi-sensing device in accordance with one or more embodiments of the present invention.

FIG. 7 is a is a block diagram illustrating the exemplary embodiment of FIG. 6. In the embodiment depicted in FIG. 6, the training station 102 includes the multi-sensing device 650. The multi-sensing device 650 includes the skin conductance sensor 202, the respiration sensor 210 and the heart rate sensor 214. The training station 102 further includes the neuro-headset 660 including the neural sensor 212. The training station 102 further includes the blood glucose sensor 204 and the blood pressure sensor 206. Each of the multi-sensing device 650, the neuro-headset 660, the blood glucose sensor 204 and the blood pressure sensor 206 are connected to the mobile user computer 122 via a wireless antenna 704 of the user computer 122. The user computer 122 includes the mobile device controller 300 coupled to the display screen 610, the speaker 630, the microphone 640, the selection button 620, the camera 605, a battery 702 and the wireless antenna 704.

In some embodiments, the mobile device controller 300 may employ one or more of the integrated sensors 120a (e.g., the camera 605 as part of the facial recognition sensor 208, and any other integrated sensors 120a not depicted in FIG. 7) and/or one or more of the external sensors 120b (e.g., one or more skin conductance sensors 202, one or more blood glucose sensors 204, one or more blood pressure sensors 206, one or more facial recognition sensors 208 (where externally provided), one or more respiration sensors 210, one or more neural sensors 212, and/or one or more heart rate sensors 214) to collect corresponding biometric data 200. For example, the mobile device controller 300 may be operable to provide commands to the ones of the sensors 120 to cause measurements to be taken by the respective ones of the sensors 120 and for those measurements to be provided to the mobile device controller 300 for processing.

In some embodiments, the wireless antenna 704 may include a Bluetooth transceiver, a network transceiver (e.g., WLAN transceiver, cellular transceiver, and/or the like), and/or similar wireless transceiver to enable wireless communication between the mobile device controller 300 and the network 118, between the mobile device controller 300 and the external sensors 120*b*, and/or the like. For example, as will be understood by those skilled in the art, where external sensors 120*b* and the wireless antenna 704 include Bluetooth transceivers, the sensors 120*b* may communicate measurements to the mobile device controller 300 via the wireless antenna 704 using Bluetooth wireless communication protocol. As a further example, where the wireless antenna includes a cellular/WLAN transceiver, the mobile device controller 300 may be able to communicate with the server 104 via the wireless antenna 704 and the cellular/WLAN network 118.

While one particular embodiment of the mobile training station 102 has been described above with reference to FIGS. 6 and 7, it is to be understood that other embodiments may be arranged in any appropriate manner. In some embodiments, for example, the mobile training station 102 may be arranged similarly to one or more of the mobile workstation arrangements described in U.S. patent application Ser. No. 13/540,300 filed on Jul. 2, 2012 and titled "SYSTEMS, COMPUTER MEDIUM AND COMPUTER-IMPLEMENTED METHODS FOR MONITORING HEALTH OF EMPLOYEES USING MOBILE DEVICES". In this way, training simulations may, for example, be provided to the user 126 at a remote work location, such as an oil-field or building site. Training simulations (such as safety training simulations) may therefore be conducted immediately prior to engaging in activities that will utilize the skills acquired during such training simulations (such as engaging in potentially hazardous activities).

Figure 8:
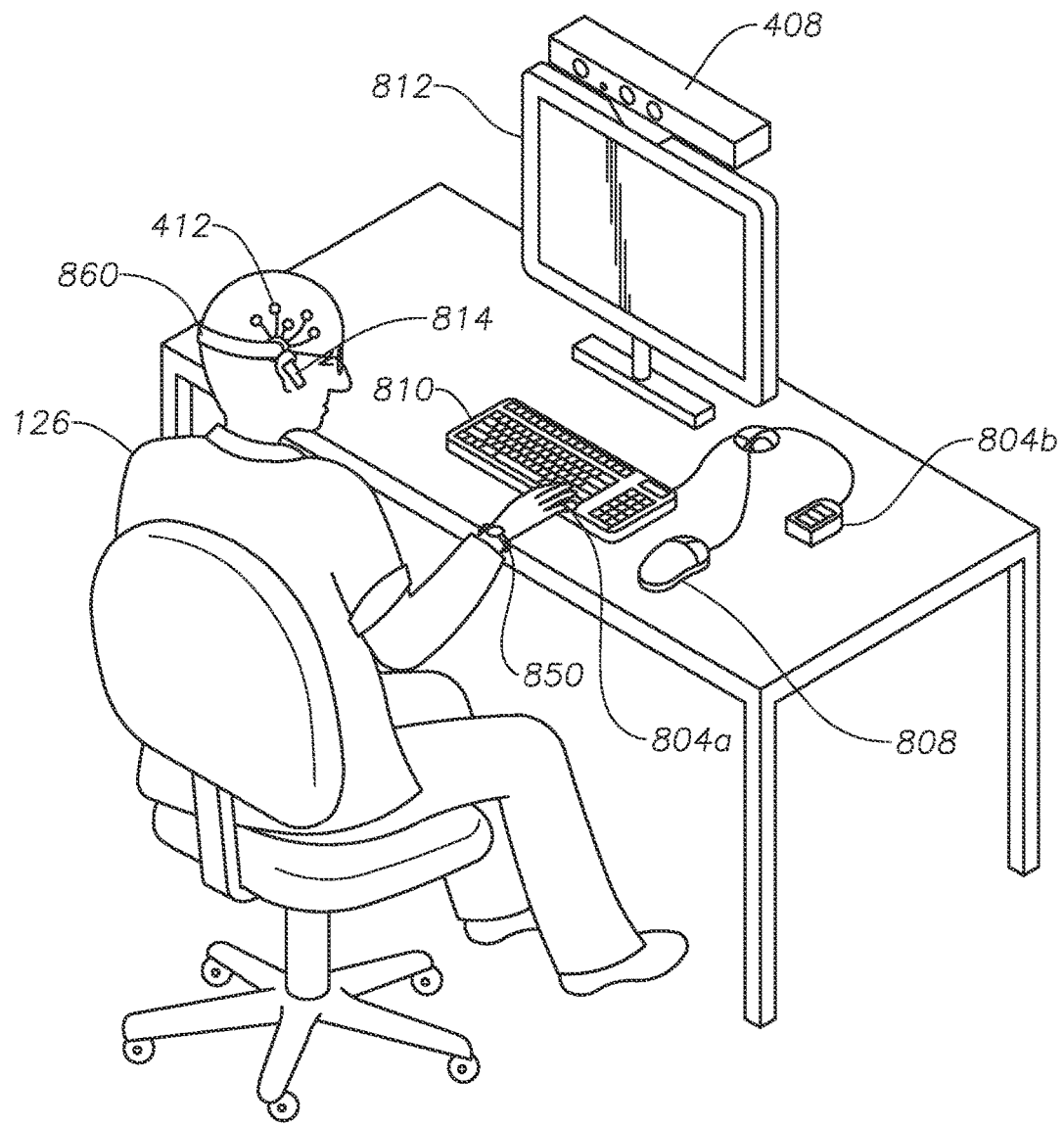
FIG. 8 illustrates a user at the training station of FIG. 4 in accordance with one or more embodiments of the present invention.

FIG. 8 is a diagram that illustrates one exemplary embodiment of the training station 103. The training station 103 may include devices, furniture and the like that facilitate the user in undertaking a training session. In some embodiments, the training station 103 may include various peripherals, such as a computer mouse ("mouse") 808, a computer keyboard 810, a display (e.g., computer monitor) 812, an audio headset 814 (e.g., a Bluetooth headset including a speaker and/or a microphone), or the like, so that the user 126 is able to receive and interact with a virtual reality simulation. In some embodiments, the facial recognition sensor 408 may be provided by a camera connected to the computer 130. In the depicted embodiment, the facial recognition sensor 408 includes a camera unit mounted atop the display 812. In some embodiments, facial recognition sensor 408 may include a two-dimensional still/video camera, a three-dimensional ("3D") still/video camera and/or the like that includes all or part of the facial recognition sensor 408.

The training station 103 includes one or more of the sensors 128 for acquiring biometrics of a user. In some embodiments, the sensors 128 are arranged similarly to the sensors 120 described above in connection with the mobile training station 102. For example, the user 126 may wear a wrist-mounted multi-sensor device 850. Alternatively, other multi-sensor devices may be utilized, such as chest mounted multi-sensor devices. The multi-sensor device 850 may provide a plurality of the sensors 128 in a convenient and compact arrangement. For example, the multi-sensor device 850 may provide the skin conductance sensor 402, the heart rate sensor 414 and the respiration sensor 410. It will be appreciated, however, that the multi-sensor device 850 may provide any number of the sensors 128 (and/or additional sensors). In other embodiments, a plurality of multi-sensor devices may be provided.

In some embodiments, a blood glucose sensor 404 may include a lancet component 804*a* disposed at the user's finger and a glucose meter 804*b* provided at the training station 103. Other embodiments may include any number of blood glucose sensors provided in any suitable configuration and any number of suitable locations such as the user's earlobe, toe and/or the like. In some embodiments, other types of blood glucose sensor may be provided for use instead of or in addition to the depicted blood glucose sensor 804*a*, 804*b*. For example, an infrared sensor (not shown) may be used to provide a blood glucose sensor. In some embodiments, a passive blood glucose sensor may be used in combination with the blood glucose sensor 804*a*, 804*b*. For example, an initial reading may be provided using the lancet-based blood glucose sensor to calibrate a passive blood glucose sensor prior to initializing a training session, with in-training blood glucose measurements being taken by a passive blood glucose sensor.

In some embodiments, a blood pressure sensor 406 is disposed at the user's arm/wrist. For example, the blood pressure sensor 406 may include a blood pressure cuff secured about the user's arm. In some embodiments, the blood pressure cuff may be integrated into a sleeve of the user's shirt. Other embodiments may include any number of blood pressure sensors provided in any number of suitable locations such as the user's upper-arm and/or the like.

In some embodiments, one or more neural sensors 412 are disposed about the user's head/scalp on a neuro-headset 860. In some embodiments, the neuro-headset 860 includes a plurality of neural sensors 412 (e.g., sixteen neural sensors 412) integrated therein. The neuro-headset 860 may provide for positioning of the neural sensors 412 in discrete neural sensor locations about the user's head.

Figure 9:
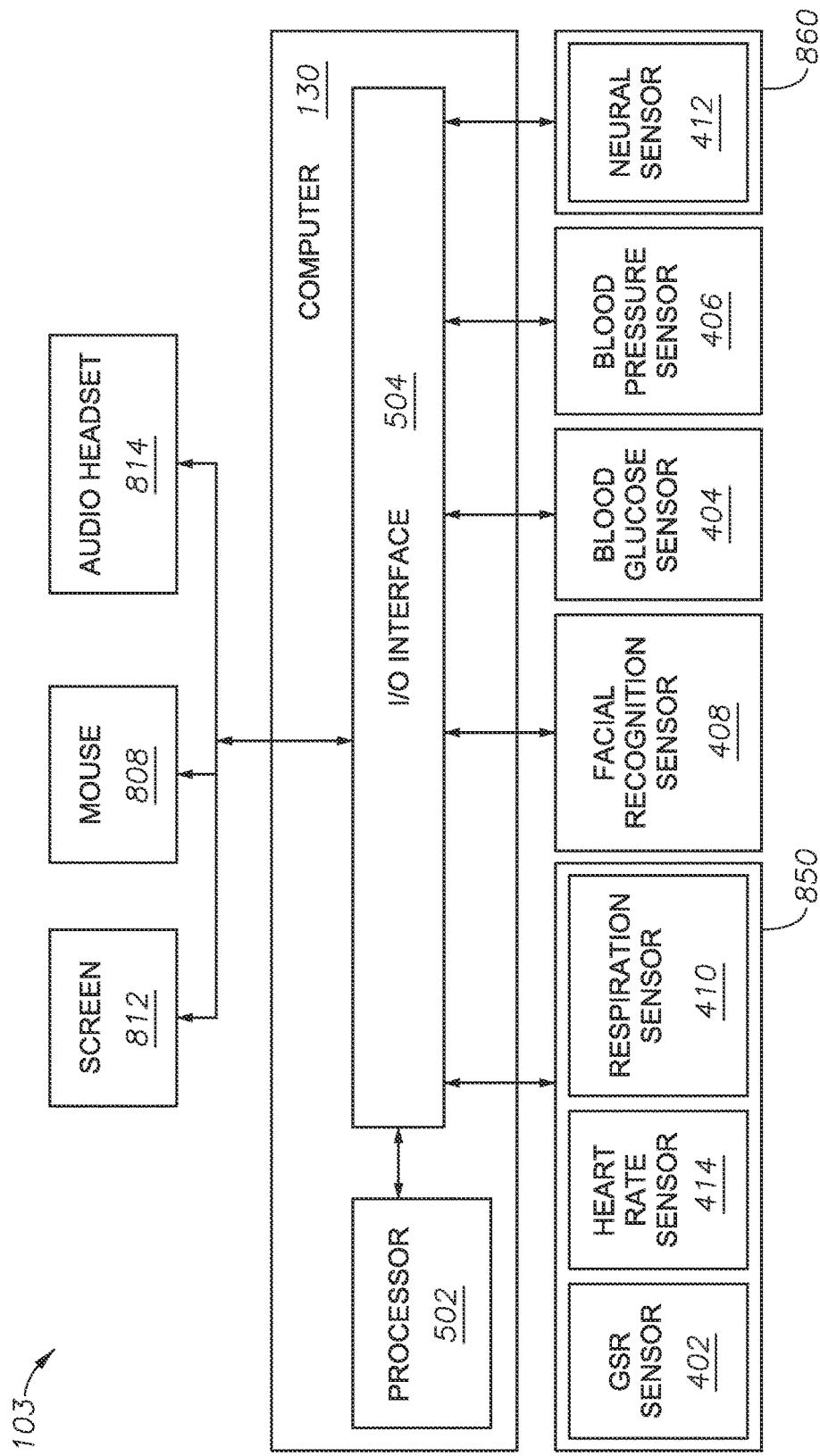
FIG. 9 is a block diagram that illustrates a training system training station including a multi-sensing device in accordance with one or more embodiments of the present invention.

FIG. 9 is a is a block diagram that illustrates the training station 103 in accordance with the particular embodiment depicted in FIG. 8, in which particular embodiment it can be seen that the computer 130 does not include integrated sensors. Rather, each of the multi-sensing device 650, the neuro-headset 660, the blood glucose sensor 204 and the blood pressure sensor 206 connect to an I/O interface 504 of the computer 130. While a particular example embodiment of the training station 103 is illustrated in FIGS. 8 and 9, it is to be understood that in other embodiments, a training station may be arranged in any appropriate manner. For example, a training station may be arranged similarly to one or more of the workstation arrangements described in U.S. patent application Ser. No. 13/540,153 filed on Jul. 2, 2012 and titled "SYSTEMS AND METHOD TO MONITOR HEALTH OF EMPLOYEE WHEN POSITIONED IN ASSOCIATION WITH A WORKSTATION". In this way, training simulations may, for example, be provided to the user 126 at their place of work. Such an arrangement may make regular and/or periodic training particularly efficient to arrange and complete.

It will be appreciated from the above that the while arranged differently, each of the training stations 102, 103 allow a user 126 to interact with a training simulation while biometric information of the user may be monitored. In the example embodiments described above, the mobile training station 102 may be conveniently used where a user cannot attend a specific testing center. For example, a mobile training station such as the training station 102 may be used in a user's own home and may utilize a user's own mobile device. Stationary training stations, such as the training station 103 may, in some embodiments, be used in an office or a dedicated training center.

To aid clarity in the following description, reference is generally made to the training station 102 and the biometric data 200. It is to be understood, however, that the following description applies equally to the training station 103 and the biometric data 400.

Figure 10:
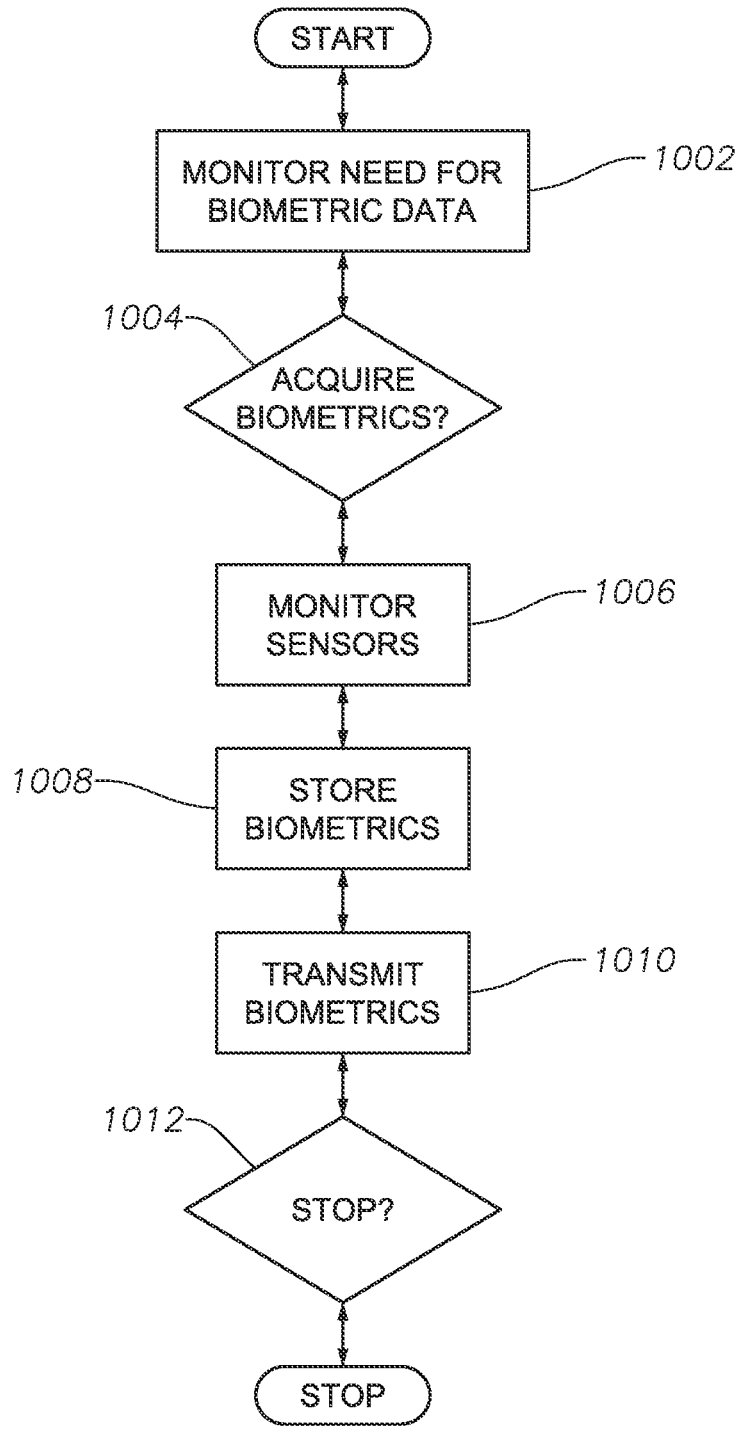
FIG. 10 is a flowchart that illustrates a method of collecting biometric data at a training station in accordance with one or more embodiments of the present invention.

FIG. 10 is a flowchart that illustrates a method of collecting biometric data 200 that may be carried out by the training station 102 in accordance with one or more embodiments of the present invention. The method of FIG. 10 may, for example, be executed by the mobile device module 308 to provide for collecting biometric data 200 by the training station 102. For example, where the method is carried out by the mobile computer 122, the mobile computer 122 may execute a routine for collecting biometric data 200 upon the user 126 successfully logging into a training application, for example, and/or upon starting a training simulation. In some embodiments, biometric data 200 may be obtained before starting a training simulation in order to obtain "baseline" biometric data with which to compare biometric data obtained during a training simulation. Similarly, in some embodiments biometric data may continue to be obtained after completion of a training simulation.

The method of FIG. 10 may include monitoring, at block 1002 the need for biometric data 200 to be obtained. In some embodiments, the need for biometric data 200 to be obtained may be identified based on a request from another component of training system 100. For example, where training is to take place using the training station 102, the mobile computer 122 may determine that there is a need to collect biometric data 200 in response to initialization of a training application portion of the mobile device module 308. Alternatively or additionally a request for biometric data may be received from the server 104 and/or the user 126.

In some embodiments, the need for biometric data 200 may be identified based on a training schedule/routine. For example, where a training schedule requires collection of biometric data 200 at 12:00 pm, it may be determined that biometric data 200 is needed if the current time is 12:00 pm. In some embodiments, the need for biometric data 200 may be determined based upon receiving signals from one or more of the sensors 120. For example, one or more of the sensors 120 may be periodically polled (or continuously monitored) to determine whether biometric data can be obtained from those one or more sensors (e.g., whether facial features are detected by a facial recognition sensor 208, or whether a current is detected at the skin conductance sensor 202). Where it is determined that biometric data can be obtained, the processing at block 1002 may determine that biometric data 200 should be obtained. It will be appreciated that in other embodiments, other criteria for determining whether biometric data 200 should be obtained may be used.

Where it is determined at block 1004 that biometric data 200 need not be obtained, the method may loop back to block 1002. As such, processing may loop through blocks 1002 and 1004 until it is determined that biometric data 200 should be obtained.

Where it is determined, at block 1004, that biometric data 200 should be obtained, the method may include proceeding to monitor one or more of the sensors 120 to collect the biometric data 200, as depicted at block 1006. In some embodiments, monitoring the sensors 120 to collect the biometric data 200 includes monitoring and/or querying the particular sensors 120 that provide the particular biometric data 200 needed. For example, different training simulations and/or different training providers, employers, users, etc., may require the collection of different biometric data 200. For example, where a training simulation simulates a hazardous environment, it may be desirable to determine a stress level to indicate a level of stress experienced by the user 126 during the simulation. Determining such a stress level may, for example, utilize the one or more neural sensors 212 and/or the one or more facial recognition sensors 208. The processing at block 1006 may therefore receive an indication as to which biometric data 200 is required for a particular training session.

In some embodiments, monitoring of the sensors 120 at block 1006 may include providing prompts to the user 126 to take any actions necessary in order to obtain particular desired biometric data 200. For example, where it is desired to obtain electronic blood glucose data 200*b*, and where the blood glucose sensor requires the user 126 to provide a blood sample, a prompt may be displayed (e.g., on the display screen 610) or played (e.g., using the speaker 630) requesting that the user 126 provide the required blood sample. Similarly, if it is detected that a particular one of the biometric data 200 cannot be obtained, a suitable prompt may be provided to the user. For example, if electronic blood pressure data 200*c* cannot be obtained, a prompt may be displayed or played to assist the user in correctly utilizing the blood pressure sensor 206.

The method of FIG. 10 may include storing the biometric data 200, as depicted at block 1008. In some embodiments, storing the biometric data 200 may include storing the collected biometric data 200 in local or remote memory. For example, the mobile computer 122 may store the collected biometric data 200 in local memory 301. In some embodiments, storing the biometric data 200 may include buffering/queuing the biometric data 200 for transmission at a later time.

The method of FIG. 10 may include transmitting the biometric data 200, as depicted at block 1010. In some embodiments, transmitting the biometric data 200 may include transmitting the biometric data 200 to another component/entity of the training system 100. For example, the mobile computer 122 may transmit the biometric data 200 (e.g., the biometric data 200 stored in memory 301) to server 104 and/or to the trainer computer 105 for use in monitoring the biometric state of the user 126. In some embodiments, the biometric data 200 may be transmitted from the mobile computer 122 to the server 104 or the trainer computer 105 via network 118.

In some embodiments, after transmitting the biometric data 200, the method may progress to block 1004 to determine whether or not the acquisition of biometric data 200 should continue. Accordingly, the mobile computer 122 may collect the biometric data 200 from the various sensors 120 as required for use in monitoring the biometric state of users as training sessions are undertaken. It may be determined that acquisition of biometric data 200 should not continue if, for example, a signal has been received that acquisition of biometric data 200 should cease. Such a signal may be received, for example, in the event that a user logs out of a training application, or a training session is ended.

It will be appreciated that the method of FIG. 10 is an exemplary embodiment of methods that may be employed in accordance with techniques described herein. The method may be may be modified to facilitate variations of its implementations and uses. The method may be implemented in software, hardware, or a combination thereof. Some or all of the method may be implemented by one or more of the modules/applications described herein, such as mobile device module 308. The order of the method may be changed, and various elements may be added, reordered, combined, omitted, modified, etc.

The server 104 (see FIG. 1) may include a network entity that serves requests by other network entities. For example, the sever 104 may serve requests made by client entities, such as the user computer 122, the user computer 130, the trainer computer 105 and/or the like. The server 104 may host a content site, such as a website, a file transfer protocol (FTP) site, an Internet search website or other source of network content. In some embodiments, the server 104 may host one or more applications, such as a training simulation and monitoring application. Some or all of the training simulation and monitoring application may be executed locally on the server 104 and/or remotely by various other network entities, such as the user computers 122, 130 and/or the trainer computer 105. For example, the server 104 may cause or allow the execution of remote applications/processes on the user computers 122, 130 to provide training simulations to, and to collect biometric data 200, 400 from, one or more users. As a further example, the server 104 may cause or allow the execution of remote applications/processes on the trainer computer 105 to allow a user of the trainer computer 105 to monitor one or more training sessions underway on the training stations 102, 103. The server 104 may also execute one or more local applications (e.g., a monitoring application) to conduct processing of the collected biometric data 200, 400 for use during and/or after the provided training session.

In some embodiments, the server 104, is connected to one or more of the user computers 122, 130, one or more file servers 106 and associated databases 108 for accessing and storing user training information 109, one or more user computers 105, one or more web servers 110 for connecting the computer server 104 to remote computers 112 (e.g., to provide communication with an offsite computer 112, for example to allow users to remotely access the training information 109 stored in database 108, to allow the server 104 to obtain external information, and/or the like).

As shown, one or more file server 106 may be employed by the system to manage the training information 109 and/or to allow the server 104, the user computers 122, 130, the trainer computer 105 and/or the remote workstation 112 to upload/download data (e.g., the training information 109) via the file server 106. The file server 106 may include or otherwise have access to the database 108. The database 108 may include a user biometric database for storing the training information 109 and/or a user access database that stores credential data and permissions data for verifying user's right to access the training system 100 based on the credentials and/or restricting access to the training system 100 based on corresponding permissions. The file server 106 and/or the database 109 may include network attached storage ("NAS"), storage area networks ("SAN"), or direct access storage ("DAS"), or any combination thereof, including, e.g., multiple hard disk drives. The file server 106 may have stored thereon a database management system, e.g. a set of software programs that controls the organization, storage, management, and retrieval of the data in the database(s) 108, such as the training information 109.

The database 108, and any other databases or files stored in the file server 106, may be a database separate from other user databases or the same database as other user databases, e.g., commingled in a database containing, for example, employee information (where the training system 100 is operated for employees). The training information 109 can also be stored in a plurality of databases (e.g., distributed databases, tables, or fields in separate portions of the file server memory). As one skilled in the art will appreciate, the file server 106 may provide the server 104, and the user computers 122, 130 access to the database 108 through, e.g., database management software or another application. A database server may be used to store the database 108 instead of or in addition to the file server 106.

In some embodiments, the computers 122, 130, 105 and/or 112 may include remote terminals that enable a user to interact with various processes being controlled by the server 104. For example, the operations described herein with regard to the user computers 122, 130 may be executed by the server 104 and the user computers 122, 130 may include network terminals that provides for user interaction with the operations provided by the server 104. Moreover, the computers 122, 130, 105 and/or 112 may provide access to computer program instructions stored on the server 104. For example, an application for providing user data running on the server 104 may be accessible via the user computers 122, 130 such that the user may provide access credentials to login into their account, the server 104 may verify their credentials/permissions, and the user may be able to enter, via the user computer 122, 130, any inputs may be required by the training system. Thus, for example, profile information provided via the user computers 122, 130 can be forwarded via the server 104 to the file server 106 for use in updating the user's information 109 stored in the database 108. In some embodiments, the computers 122, 105 can interface with different servers (e.g., the web or network servers 104, 106 or 110) for accessing the information 109 via the communications network 118.

The trainer computer 105 may provide a second user, such as a training provider, or an employer (e.g., the user's manager, the user's human resources manager, or the like) access to the training information 109 and/or corresponding reports for reviewing, in real-time or retrospect, the training sessions of one or more users. In some embodiments, the second user may use the trainer computer 105 to interact with a virtual reality simulation provided to a first user as part of a training session and/or to interact with a first user undertaking training with the training system 100. The trainer computer 105 may therefore provide input and output devices appropriate to allow the second user to interact with both a virtual reality simulation and with the first users.

Figure 11:
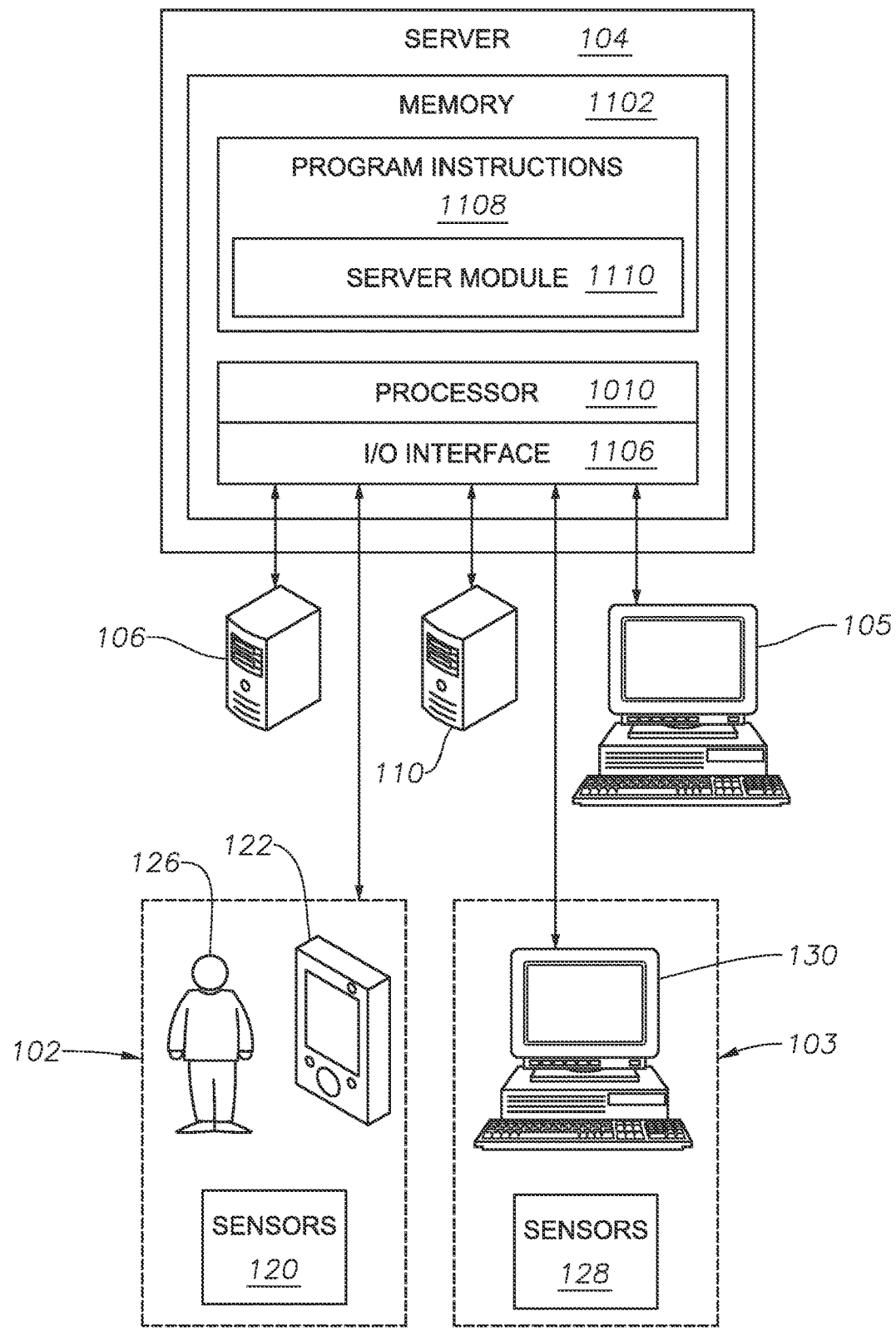
FIG. 11 is a block diagram illustrating components of a server in accordance with one or more embodiments of the present invention.

FIG. 11 is a block diagram illustrating components of the server 104 in accordance with one or more embodiments of the present invention. In some embodiments, the server 104 includes a memory 1102, a processor 1104 and an input/output (I/O) interface 1106. The memory 1102 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, harddrives), or the like. The memory 1102 may include a non-transitory processor-readable storage medium having program instructions 1108 stored thereon that are executable by a computer processor (e.g., the processor 1104) to cause the functional operations described herein with regard to the server 104. The program instructions 1108 may include a server module 1110 including program instructions that are executable by the processor 1010 to provide some or all of the functionality described herein with regard to the server 104.

The processor 1104 may be any suitable processor capable of executing/performing program instructions. The processor 1104 may include a central processing unit (CPU) that carries out program instructions (e.g., of the server module 1110) to perform arithmetical, logical, input/output and other operations of the server 104. The processor 1104 can be any commercially available processor, or plurality of processors, adapted for use in the computer server 104, such as those manufactured by Intel Corporation, AMD Corporation, or the like. As one skilled in the art will appreciate, the processor 1104 may also include components that allow the computer server 104 to be connected to peripherals (e.g., a display and keyboard that would allow direct access to the processor and the memory 1102, and/or application executing via the server 104).

The I/O interface 1106 may provide an interface for connection of one or more I/O devices to server 104. The I/O devices may include other network devices, such as the file server 106, the web server 110, the user computers 122, 130, the trainer computer 105, the sensors 120, 128 and/or the like. The I/O devices may be communicatively coupled to the I/O interface 1106 via a wired or wireless connection.

Figure 12:
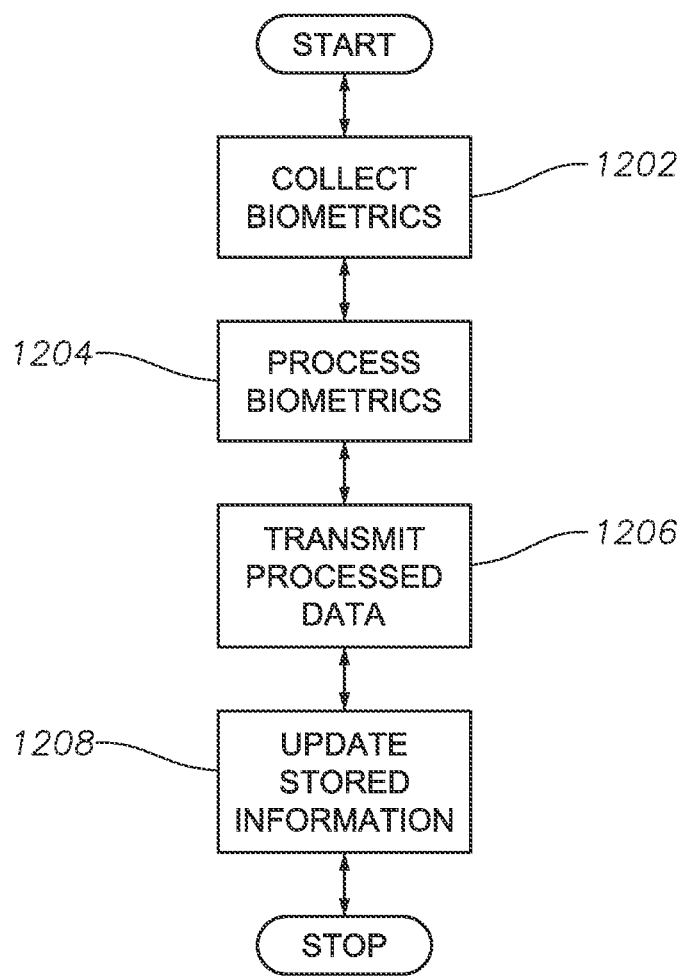
FIG. 12 is a flowchart that illustrates a method of collecting biometric data at the server of FIG. 11 in accordance with one or more embodiments of the present invention.

In some embodiments, the server 104 uses the biometric data 200, 400 collected by the sensors 120, 128 to monitor a biometric state of a user 126 before, during and/or after a training session. FIG. 12 is a flowchart that illustrates a method of monitoring the user's biometric state in accordance with one or more embodiments of the present invention. In other embodiments, monitoring of a user's biometric state is performed at the user computer 122, 130 of the training station 102, 103 from which the biometric data is acquired. In order to aid clarity, the following description refers, generally, to collecting biometric data 200 from the training station 102. It will be understood, however, that the following description applies equally to collection of biometric data from other training stations, such biometric data 400 from the training station 103.

The method of FIG. 12 may include collecting biometric data 200, as depicted at block 1002. In some embodiments, collecting biometric data may include collecting biometric data 200 from the training station 102. In some embodiments, collecting biometric data 200 may include an initialization protocol between the server 104 and the user computer 122. For example, suitable signals may be sent from the server 104 to the user computer 122 to indicate that biometric data 200 is required, thereby automatically causing the processing of FIG. 10 to progress from block 1004 to block 1006. In some embodiments, collecting biometric data 200 may include sending a suitable signal to the user computer 122 to display a prompt to the user 126 to request that the user 126 take action to initiate the collection of biometric data 200. In some embodiments, the collection of biometric data 200 by the server 104 may begin upon receiving a signal from user computer 122. For example, a signal may be received at block 1202 indicating that the server 104 should begin processing required to collect biometric data 200.

As described herein, the mobile computer 122 may collect the measurements from each of the sensors 120 of the training station 102 and transmit corresponding biometric data 200 to the server 104 for use in monitoring the biometric state of the user 126. In some embodiments, the data is collected and provided to the server 104 in real-time (e.g., within about 1 minute of being collected by the sensors 120). In some embodiments, the biometric data 200 for one or more users may be logged over time as part of the training information 109. For example, biometric data 200 may be collected for each of a group of users as those users undertake training through the training system 100. The training information 109 for each of the users may be updated to reflect the biometric data collected. Thus, a log of biometric data associated with training activity, may be generated for each of the users. In some embodiments, the log of biometric data for a given user may be used to generate a profile for the user. For example, the logged biometric data for the user 126 may be used to generate profiles and/or reports that are based on current/recent training that the user 126 has undertaken and the biometric data associated with that training. Additionally, or alternatively, the logged biometric data may be used to generate profiles and/or reports that are based on historical training that the user has undertaken and the biometric data 200 associated with that training. In this way, the effect, efficacy, etc., of training sessions may be monitored both for a particular individual user and between users.

The method of FIG. 12 may include processing the collected biometric data at block 1204. Processing at block 1204 may include processing raw biometric data 200 to enable the biometric data 200 to be used in providing training. For example, the collected biometric data 200 may be processed to determine one or more of a stress level, an indication of a user's level of interest, an indication of a user's level of engagement, an indication of a user's level of alertness and/or an indication of a user's level of excitement. In some embodiments, a stress level may be determine responsive to analysis of one or more of electronic heart rate data 200g, the electronic respiratory rate data 200e, the electronic skin conductance data 200a, the electronic blood glucose data 200b and the electronic blood pressure data 200c. In some embodiments, the stress level may be determined based upon analysis of others of the electronic biometric data 200, such as, for example, electronic facial recognition data 200d and the electronic neural data 200f. In some embodiments, the raw biometric data 200 is time-stamped, or otherwise associated with a time. In such an embodiment, the data (or at least a time-stamped segment of data) can be associated with one or more events during testing that occur at or near the time. For example, portions/segments of biometric data 200 with time stamps that fall within about 1:45:30 pm to about 1:46:00 pm may be associated with a stressful event that occurred during testing at about 1:45:30 pm. Thus, a response of the user 126 to the event can be determined using the portions of biometric data 200 that have time stamps that fall within about 1:45:30 pm to about 1:46:00 pm.

In some embodiments, a level of interest, engagement, alertness and/or excitement of the user 126 may be determined. For example, a level of interest, engagement, alertness and/or excitement may be determined responsive to analysis of the electronic neural data 200f, and/or the electronic facial recognition data 200d. In some embodiments, the a level of interest, engagement, alertness and/or excitement may be determined responsive to analysis of others of the electronic biometric data 200, such as, for example, electronic heart rate data 200g, the electronic respiratory rate data 200e, the electronic skin conductance data 200a, the electronic blood glucose data 200b and the electronic blood pressure data 200c.

In some embodiments, the processing at block 1204 includes generating visual representations of the electronic biometric data for display in real-time during a training session. The visual representations may include numerical representations, graphical representations and any other form of visual representations. In some embodiments, as described in more detail below, visual representations generated at the block 1204 may include an avatar for display on the user computer 122 and/or the trainer computer 105. For example, an avatar may provide a virtual representation of the user 126, and be updated to reflect the biometric state of the user 126 in a way that may be readily interpreted by the user 126. By providing feedback through an avatar, the skills and competencies that are being trained through the system 100 are better internalized by the user 126 such that training is more efficient and effective.

In some embodiments, the processing at block 1204 includes generating training reports 109 for storage in the database 108. The training reports 109 generated at block 1204 may include indications as to the types of training that the user 126 has undertaken and their corresponding biometric data, such as the biometric data 200, the determined stress levels, level of interest, engagement, alertness and/or excitement. In some embodiments, the training reports 109 can include the biometric data being time-aligned with events during the testing. This may enable a determination of the biometrics of the user 126 at specific times and events during the testing such that the biometric data, and corresponding responses, of the user 126 can be associated with specific times and events during the testing. In some embodiments, the reports allow the user, a training provider, an employer, etc., to review a training session undertaken by the user 126 and to determine how the user reacted, biometrically, to one or more scenarios presented during the training session. In this way, a user, training provider, employer, etc., may be able to determine further actions for that user. For some types of training, such as management training, for example, training reports may allow an employer to determine which users display particular qualities necessary for particular roles within an organization (such as management competencies, health and safety awareness, etc.).

In some embodiments, the server 104 may transmit processed biometric data, visual representations and/or reports, to other entities in the training system 100 as depicted at block 1206. For example, as described above, the server 104 may transmit visual representations to the user computers 122, 130 and/or trainer computer 105 for display to a user and/or a trainer. In some embodiments, the processed biometric data, visual representations and/or reports can be used to generate an overall profile of the user 126. In some embodiments, processed biometric data, visual representations, reports and/or user profile may be transmitted to the file server 106 for storage in the database 108 as training reports 109 (e.g., updating information already stored in the database 108). In some embodiments, a user profile can be generated and/or updated for the user(s) 126. For example, periodic (e.g., weekly, monthly, yearly, etc.) testing may be conducted for some or all of the users 126 in an organization, and their respective user profiles can be updated to reflect the results of the periodic testing. Such profiles (e.g., leadership ability profiles) can be useful, for example, to assess the developments of users 126 overtime in various areas, including leadership.

It will be appreciated that the method of FIG. 12 is an exemplary embodiment of methods that may be employed in accordance with techniques described herein. The method depicted in FIG. 12 may be may be modified to facilitate variations of its implementations and uses. The method may be implemented in software, hardware, or a combination thereof. Some or all of the method may be implemented by one or more of the modules/applications described herein, such as server module 1110. The order of the method may be changed, and various elements may be added, reordered, combined, omitted, modified, etc.

Figure 13:
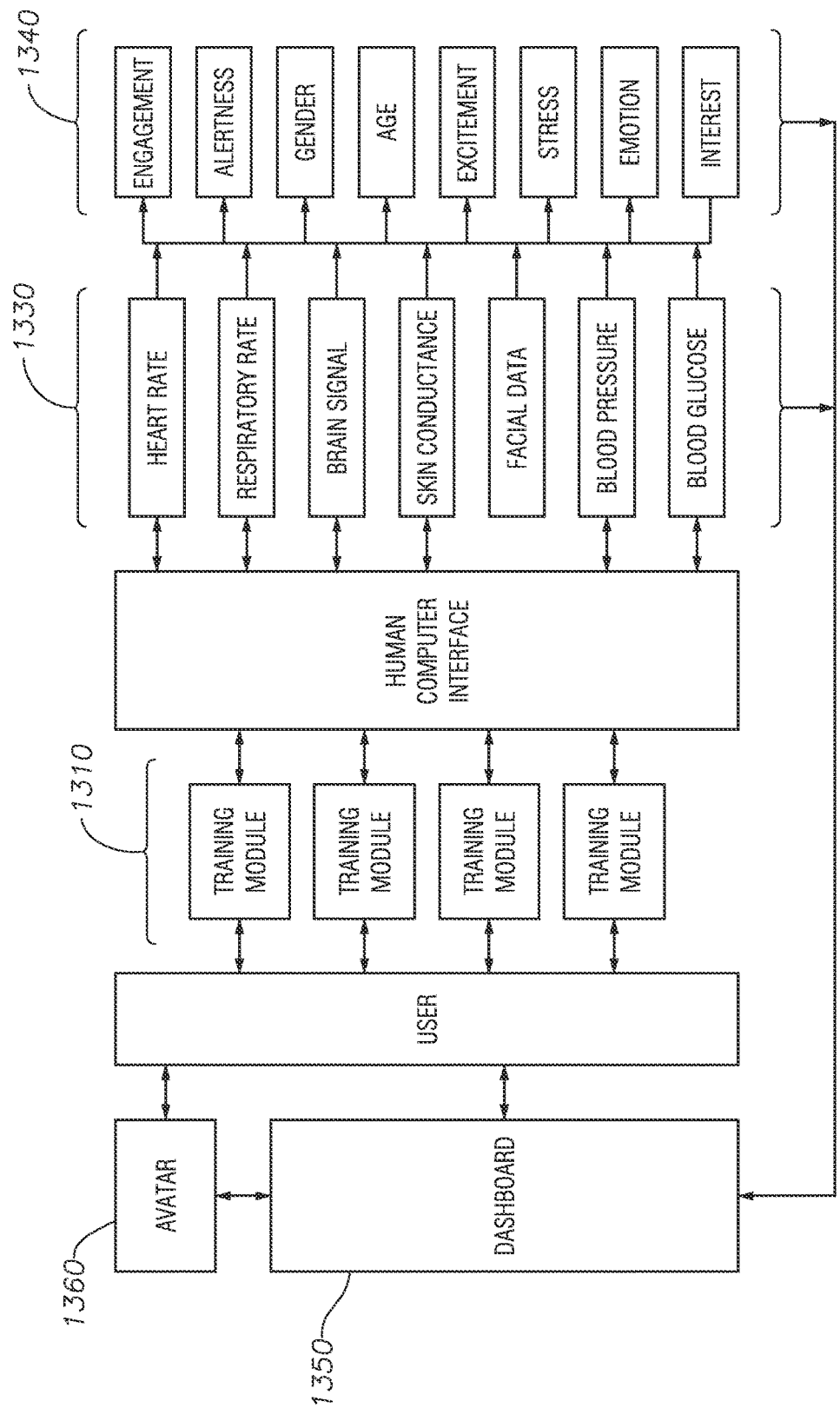
FIG. 13 is a block diagram illustrating dataflow between functional components of a training system in accordance with one or more embodiments of the present invention.

FIG. 13 schematically depicts information flow between functional components of the training system 100 in accordance with some embodiments. In the embodiment of FIG. 13, the user 126 is provided with access to one or more training modules 1310. In FIG. 13, four training modules are depicted, although it will be understood that this is merely exemplary and that any number of training modules 1310 may be provided. In some embodiments, the training system 100 is a management training system and one or more of the modules 1310 may be directed towards training the user 126 in various skills and competencies applicable to the management of people, systems, processes and/or the like. By way of example, management training modules may include an empowerment module, a people conversations module, a decision making module, a collaboration module, etc. Each module may include one or more sub modules, lessons, etc. (all referred to as modules herein for clarity) with particular training aims, tasks and requirements, etc. Each module may include one or more virtual reality simulations with which the user 126 interacts in order to complete the training provided by that module.

Each module utilizes a human computer interface 1320 in order to access biometric data 1330 provided by measurements taken by one or more of the plurality of sensors 120, 128. As described above, the biometric data 1330 provided by the sensors may be used to determine one or more further biometric states 1340. For example, one or more of the 1330 may be used to calculate a level of engagement 1341, an level of alertness 1342, a level of excitement 1343, a level of interest 1344, a gender indication 1345, an age indication 1346, an emotional state indication 1347 and a stress level 1348. It will be appreciated that determination of each of the further biometric states 1340 may utilize any one or more of the biometric data 1330. Each of the training modules 1310 may utilize different ones of the biometric data 1330, 1340 depending on the training aims and requirements of that training module. The biometric data 1330 may be referred to as biometric sensor data and the biometric data 1340 may be referred to as derived biometric data for convenience. It will be appreciated, however, that as described above, processing may be performed on data received directly from the sensors 120, 128 to obtain desired biometric data. As such, it will be understood that the terms sensor biometric data and derived biometric data do not indicate limitations as to the processing that is performed to obtain the respective biometric data.

The biometric data 1330 and/or the further biometric data 1340 may be used to provide the user 126 and/or a training provider, employer, etc., with a real-time view (e.g. in a dashboard 1350 displayed on a display of a user computer 122, 130) indicating one or more of the biometric states of the user 126 as the user 126 interacts with one of the virtual reality training simulation. By providing a real-time view of the biometric states of the user 126, the user (and/or a training provider, employer, etc.) is provided with a visual representation of the user's biometric response to the training. This biometric feedback therefore allows the user 126 to monitor their performance during the virtual reality training simulation. For example, while a training goal may be to practice handling difficult situations calmly, a user 126 may not always be aware of when their stress level, level of anger, etc., is increasing. By providing a visual representation of the user's biometrics, the user can use that feedback to practice calming measures during the training simulation and directly observe the result of those measures.

In some embodiments, the training system 100 may be operable to detect when one or more of the biometric states 1320, 1330 exceeds a boundary condition. Upon determining that one or more of the biometric states 1320, 1330 has exceeded a boundary condition, assistive prompts (or alerts) may be provided to the user 126. In some embodiments, a prompt may be automatically generated and provided directly to the user 126. For example, upon determining that a stress level has been exceeded, a prompt may be provided to the user to regulate their breathing. In some embodiments upon determining that one or more of the biometric states 1320 has exceeded a boundary condition, prompts may also or alternatively be provided to a training provider (e.g. via the trainer computer 105). For example, a training provider may be prompted to monitor the user 126 closely, or more specific prompts may be provided. For example, a prompt may be provided to a training provider to provide coaching for a specific training goal.

In some embodiments, one or more of the biometric boundary conditions (e.g., a maximum value of the stress level 1348) may be pre-set. For example, a user's heart rate may be compared to a known safe or desirable heart rate or heart rate range. Similarly, responses by the training system 100, such as particular prompts (or alerts) provided to the user 126 may be pre-set.

In some embodiments, one or more biometric boundary conditions, goals, and/or prompts to be provided to the user 126 may be dynamically determined. That is, by monitoring a user's interactions with the training system 100 over time, the training system 100 may automatically personalize the training that is provided to each individual user of the training system 100. By way of example, where a user is new to a particular training module or training aim, boundary conditions for that training aim may be set relatively widely (e.g. relatively high and/or low, depending on the biometric states 1330, 1340 being monitored). Where a user's training history indicates that the user is making progress with a particular training aim (e.g., displaying better regulation of their breathing, better stress management, etc.) boundary conditions for that training aim may be adjusted. In this way, the system 100 is able to adjust the biometric feedback provided to the user 126 in order to increase the effectiveness of ongoing training. Similarly, in some embodiments, particular training aims may be determined for the user 126 based on their biometric responses to previous training. For example, if a user performs particularly poorly on a training module designed to develop skills of stress management, additional stress management training may be suggested and/or provided. Similarly, in some embodiments, real-time prompts (e.g. textual, graphical, audible, etc.) may be selected in dependence upon a user's real-time biometric responses and/or their biometric response history.

In some embodiments, the system 100 may utilize other information about the user 126 to dynamically set biometric boundary conditions, to suggest training to be undertaken, to provide personalized in-training prompts, etc. For example, where one or more health profiles/reports are available for a user (such as, for example, described in U.S. patent application Ser. No. 13/540,300 filed on Jul. 2, 2012 and titled "SYSTEMS, COMPUTER MEDIUM AND COMPUTER-IMPLEMENTED METHODS FOR MONITORING HEALTH OF EMPLOYEES USING MOBILE DEVICES", and/or U.S. patent application Ser. No. 13/540,153 filed on Jul. 2, 2012 and titled "SYSTEMS AND METHOD TO MONITOR HEALTH OF EMPLOYEE WHEN POSITIONED IN ASSOCIATION WITH A WORKSTATION"), such health profiles/reports may be utilized in determining appropriate boundary conditions, feedback prompts, and training goals to be provided to the user. For example, where a training report indicates a particular health problem (e.g., persistently higher blood pressure), training may be suggested to help to improve that health problem (e.g., mindfulness training).

In some embodiments, the user's emotions, thoughts and facial movements may be determined based upon sensed brain signals (e.g., electronic neural data 200f, 400f). For example, a plurality of predetermined brain wave patterns may be associated with corresponding emotions, thoughts, facial movements and/or motor functions. During processing of the brain signals, the sensed/observed brain signals may be compared to the plurality of predetermined brain signal patterns to identify any matches or similarities. Upon detecting a match or similarity of the observed brain signals to one or more of the predetermined brain signal patterns, the user's emotion (e.g., happy, sad, excited, depressed, etc.), thoughts (e.g., engagement with the training, interest in the training, alertness, excitement, etc.), facial movements (e.g., facial gestures such as smiling) that correspond to the matching predetermined brain signal pattern may be recorded. In some embodiments an avatar module 1360 may be used to generate a real-time avatar which mimics the user's current emotional state and/or facial gesture. For example, when it is determined that the user is happy and/or smiling, a displayed avatar can be animated to smile, providing the user or other persons reviewing the user's biometric state (e.g., a training provider, an employer, etc.) with an indication of the user's current emotional state and/or facial expression. In some embodiments, the ability to determine the user's thoughts may be employed to assist the user with training, as described above.

In some embodiments, the avatar module 1360 may be operable to recreate an avatar after a training session from biometric states of the user 126 sampled during the training session. For example, the biometric states 1330, 1340 may be sampled at predetermined intervals and stored (e.g. as training information 109 in the database 108). The sampling and storage of one or more of the biometric states 1330, 1340 allows for a comprehensive review of the user's biometric states during a training session. The stored biometric samples may additionally be used by the avatar module 1360 to recreate the avatar that was displayed to the user 126 at the time corresponding to the sampled data, in order to provide a visual representation of the development of the user's biometric state during a training session. In some embodiments, an image of the avatar may be sampled at predetermined intervals (e.g. every second, every two seconds, etc.) during a training session and each sampled avatar image stored (e.g. as training information 109 in the database 108). The stored avatar image samples may then be played back as an animation during a post-training review, thereby providing a visual representation of the development of the user's biometric state during a training session. In this way, processing necessary to recreate an avatar may be reduced. Additionally, in some embodiments, storage of avatar image samples only, may allow for storage requirements to be reduced. This may be beneficial where a comprehensive review of one or more of the biometric states 1330, 1340 during a training session is not required.

In some embodiments, the avatar module 1360 may be configured to generate a coaching avatar that provides instructions, suggestions, and/or demonstrations that are intended to help coach the user during training. For example, as described herein, the avatar module 1360 may provide an avatar for demonstration of training techniques, such as breathing, meditation, etc. In some embodiments, the avatar module 1360 may be operable to provide audio information (e.g., via speakers of the computer 122, 130).

Figure 14A:
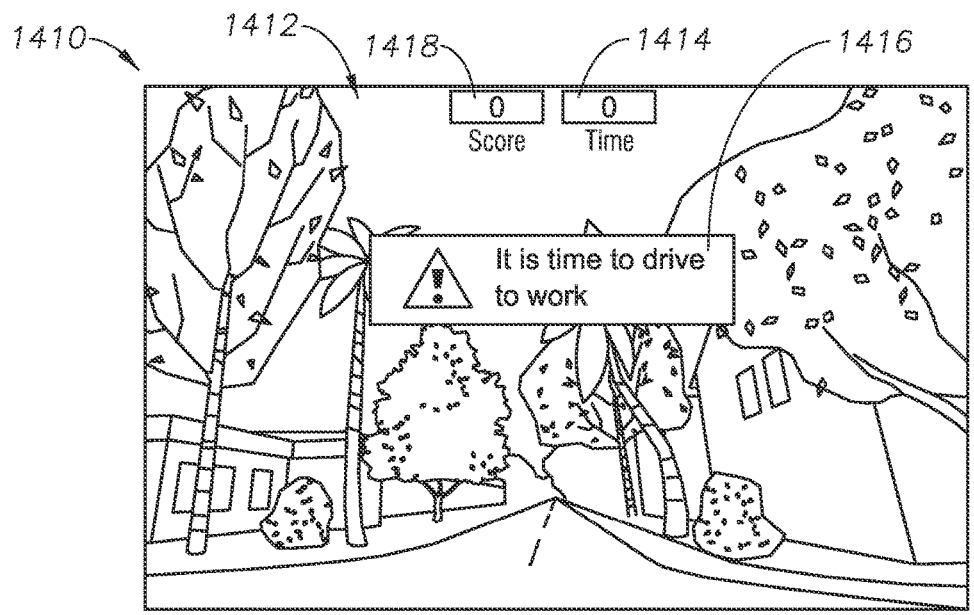
FIGS. 14A, 14B illustrate a virtual reality simulation that may be provided by a training system in accordance with one or more embodiments of the present invention.
Figure 14B:
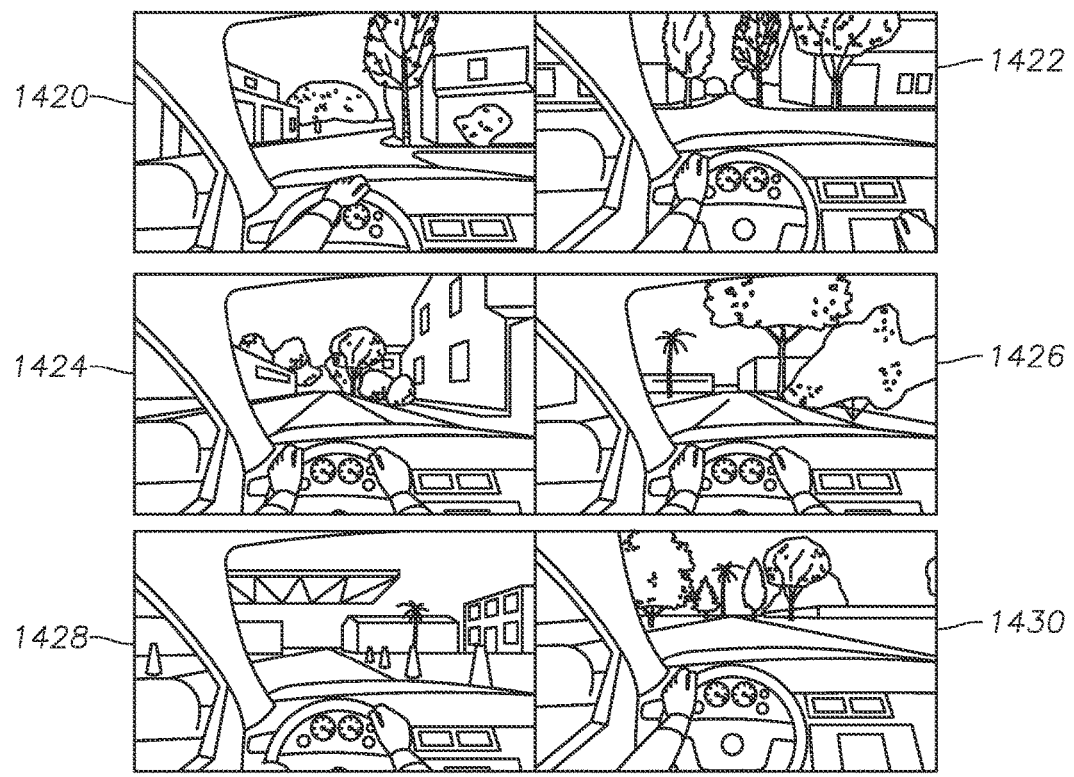

As described above, each training module 1310, sub module or lesson may include one or more virtual reality simulations. Each virtual reality simulation may present the user 126 with a simulated environment in which to undertake one or more training exercises. A user may interact with the virtual reality simulation in order to complete the training exercises. FIGS. 14A, 14B illustrate a virtual reality simulation which presents the user 126 with a driving simulation as part of a health and safety training module. FIG. 14A illustrates an initial view 1410 in which a scene 1412 of a road is displayed from a first person perspective. That is, from the point of view of the user 126, the user 126 views the scene 1412 through the eyes of an avatar (the user's manifestation within the virtual reality simulation) that is looking along the road. A dialogue box 1414 provides a textual indication ("It is time to drive to work") of a task that the user 126 is to perform. A timer 1416 in a top portion of the view 1410 indicates an amount of time that has elapsed during the training session and is shown in FIG. 14A with a value of "0". In some embodiments, the timer 1416 may display, or may be configurable to display, an amount of remaining time available for the user 126 to complete a task within the virtual reality simulation. A counter 1418 displays a score that has been accrued by the user 126 during the virtual reality simulation and is shown in FIG. 14A with a value of "0".

FIG. 14B illustrates six scenes 1420-1430 that may be displayed to the user 126 as he interacts and engages with the virtual reality simulation. In the scenes 1420-1430 the user 126 is presented with a first-person view from within a car. The user may provide inputs to the user computer 122 (or user computer 130) in order to simulate driving the car. It will be appreciated that any user input devices may be provided. In some embodiments, in order to accurately simulate a particular environment, input devices may be selected to match the tasks being simulated. For example, in the virtual reality simulation of FIGS. 14A, 14B, a steering wheel input device may be provided. Realistic input devices may allow the system 100 to provide a more immersive training experience, thereby contributing to associations made within the user's brain and increasing the training's efficacy. The system 100 may score the user 126 based upon actions taken within the virtual reality simulation. For example, if the user accelerates too rapidly, brakes too suddenly, or corners too sharply, points may be deducted. It will be appreciated that any appropriate scoring mechanism may be used and that the exact scoring mechanism will, generally, depend upon the particular virtual reality simulation and training being provided.

In some embodiments, one or more virtual reality simulations (or parts of virtual reality simulations) may not require user input to control the user's avatar. For example, with reference to FIGS. 14A, 14B, the user 126 may observe the scenes that are displayed on the display screen of the user computer 122 (or 130) without active control. In this case, the training may require the user to identify (e.g. by appropriate input such as touching the screen, pressing a key on a keyboard, etc.), when a health and safety issue arises. For example, points may be awarded for successful identification of valid health and safety issues, no points awarded for failure to identify a valid health and safety issue, and points deducted for identification of invalid health and safety issues. It will be appreciated that the example virtual reality simulations, user interfaces and scoring mechanisms shown in FIGS. 14A, 14B and described above are provided only by way of example and that embodiments any utilize any manner of virtual reality simulation, user interface and scoring mechanism as appropriate to one or more particular training aims. It is to be further understood that while the use of virtual reality simulations may provide for a particularly effective training method, other forms of training may be provided. For example, a conversational training module may be provided in a purely textual form.

One or more information dashboards may be displayed to the user 126, or to a training provider (or employer, etc.) during a virtual reality simulation. Such an information dashboard may be displayed, for example, overlaid on a portion of the virtual reality simulation, or on a different screen to the screen on which the virtual reality simulation is displayed (e.g. a screen of a training provider, employer, etc.). In some embodiments, information dashboards may be displayed subsequent to completion of a training session rather than, or in addition to, being displayed simultaneously with a training session. In some embodiments, an information dashboard may only be displayed simultaneously with a training session upon detection that one or more of the biometric parameters of the user 126 have exceeded one or more bounds. For example, where it is determined that a user's heart rate has exceeded a maximum heart rate, a heart rate indicator (and/or other indicators) may be displayed to the user.

Figure 15:
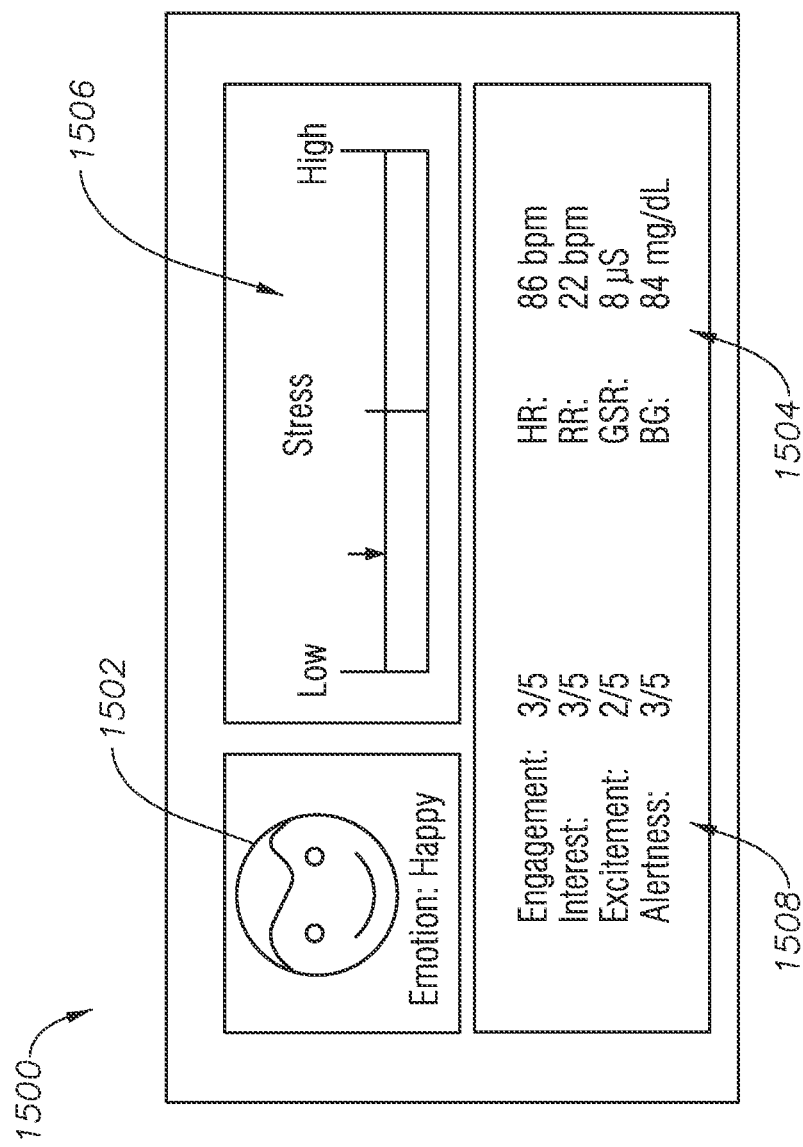
FIG. 15 illustrates an information dashboard that may be provided to a user of a training system in accordance with one or more embodiments of the present invention.

FIG. 15 illustrates an example of an information dashboard 1500 that may be provided in some embodiments. The dashboard 1500 may include an avatar 1502, a biometric summary 1504, a stress indicator 1506, a training response summary 1508, and/or the like. In some embodiments, the avatar 1502 includes a graphical depiction of the user's current emotional state, facial expression, gestures, and/or the like. For example, in response to determining that the user is smiling and/or happy (e.g., from the electronic neural data 200ƒ and/or the electronic facial recognition data 200d), the avatar 1502 may be dynamically updated to include a graphic illustration of a smile, as depicted, to mimic the current emotion and/or facial expression of the user. While the avatar 1502 is shown in FIG. 2 as including a depiction of a face, it will be appreciated that the avatar 1502 may be more detailed, and may include a depictions of other parts, or a whole, of a human body. In some embodiments more than avatar may be provided.

In some embodiments, the biometric summary 1504 displays of some or all of the current biometric states of the user based on the biometric data 200, 400 received from the sensors 120, 128. For example, in the illustrated embodiment, the biometric summary 1504 includes an indication of the user's heart rate (HR), respiratory rate (RR), skin conductance (GSR) and blood glucose (BG). In some embodiments, the stress indicator 1506 includes an indication of the current determined level of stress the user. In some embodiments, the training response summary 1508 displays some or all of a determined level engagement of the user 126, a determined level of interest of the user 126, a determined level of excitement of the user and a determined level of alertness. The levels of engagement, interest, excitement, and alertness are depicted as having a rating out of five ('5'), however, it will be appreciated that this is merely exemplary. The levels of engagement, interest, excitement, and alertness may be determined from the biometric data 200, 400 in any appropriate way as will be readily apparent to those skilled in the art. For example, level of engagement, interest, excitement and alertness may be determined at least in part from the neural data 200ƒ, 400ƒ and the electronic facial recognition data 200d, 400d. By way of further example, detection of an increase alpha waves and/or a relaxing of facial muscles, may indicate a reduction in engagement, interest, excitement and alertness.

In some embodiments, only portions of the dashboard 1500 may be displayed during a training session, for example, only the avatar 1502. As described above, a virtual reality simulation generally provides a simulation avatar which is the user's manifestation in the simulation. Additionally, or alternatively, therefore, where a virtual reality simulation provides perspectives in which all or part of the simulation avatar is visible, the user's biometric states may be reflected directly in the visible simulation avatar (in addition to, or instead of, the avatar 1502). For example, where the simulation avatar's face is visible, emotions of the user 126 may be reflected on the face of the simulation avatar within the virtual reality simulation.

Figure 16:
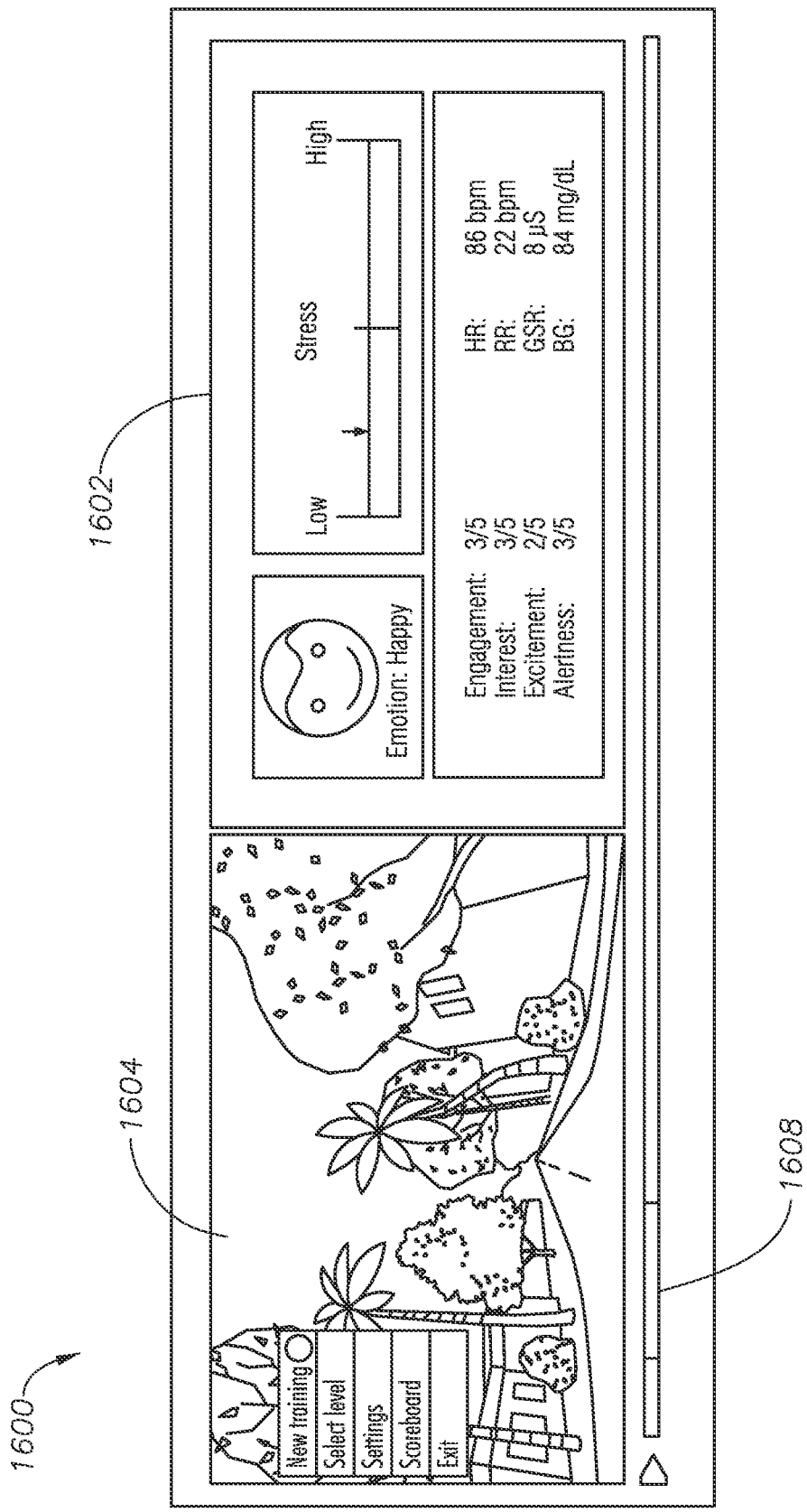
FIG. 16 illustrates a training review function that may be provided to a user of a training system in accordance with one or more embodiments of the present invention.

As indicated above, an information dashboard (or other presentation of biometric information) may be provided to the user 126 (or a training provider, employer, etc.) during a training session for real-time monitoring of the user 126, or after a training session for a post-training review of the user's performance during the training session. For example, as depicted in FIG. 16, a reviewer may be provided with a view 1600 including both an information dashboard 1602 and a recorded training session 1604. In this way, a reviewer can view a user's recorded biometric states together with the activity of the user in the training session. A progress bar 1606 may be provided to allow a reviewer of the training session (e.g. the user or a provider, etc.) to control playback and to select specific times of the training. In some embodiments, interest points, for example times at which a user's biometric parameters meet some predetermined criteria, may be noted during the training session. Navigation means may be provided to allow efficient location and playback of interest points during review. For example, in the embodiment depicted in FIG. 16, a plurality of markers 1608, 1610, 1612 are provided on the progress bar 1606 to indicate positions in the recording of the training session and biometric states of interest. The markers 1608-1612 may be selectable to allow a user to accurately navigate to the indicated periods of interest. It will be appreciated that any other navigable indicators for periods of interest may be provided, such as one or more lists.

Figure 17:
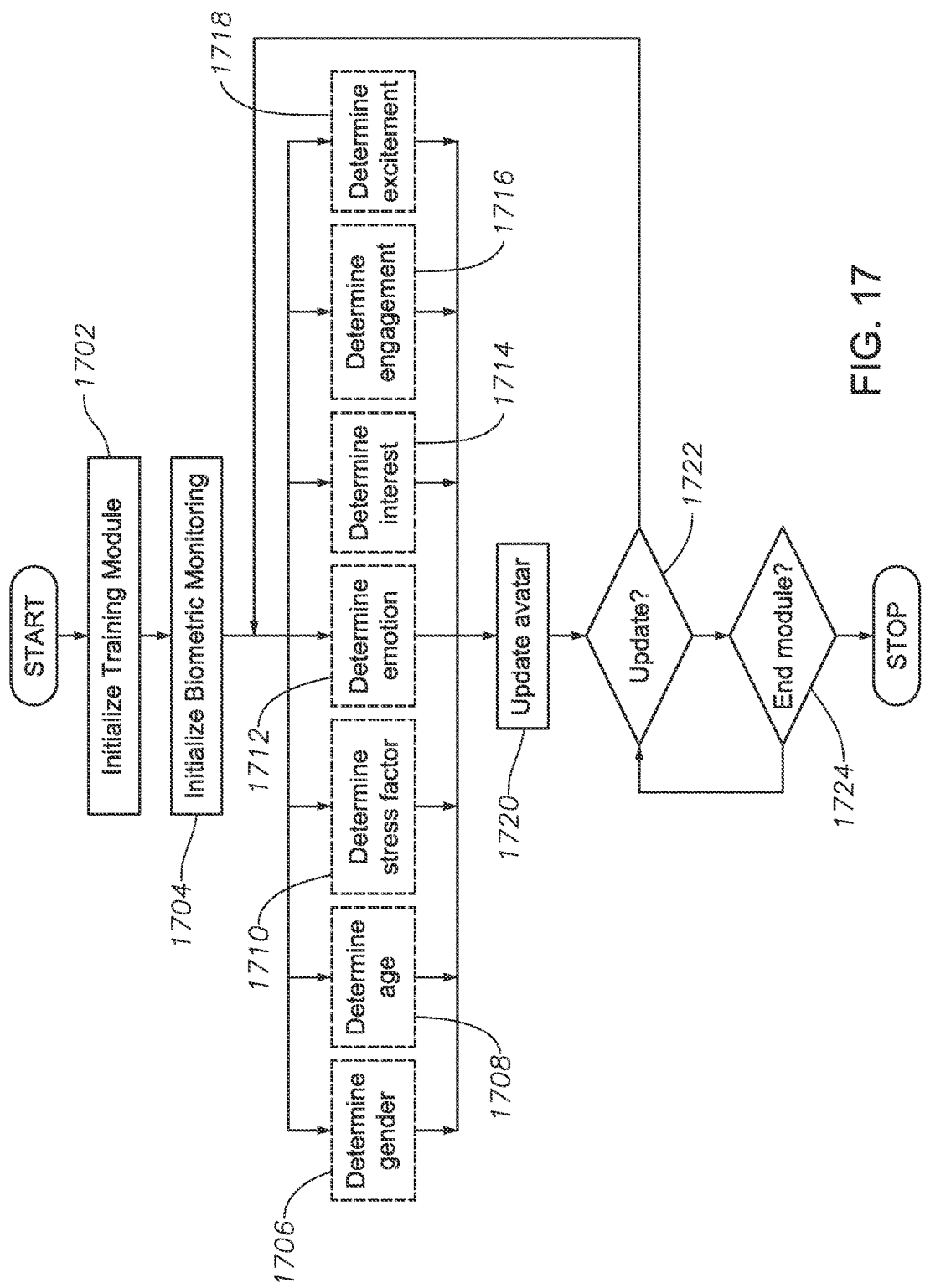
FIG. 17 is a flowchart that illustrates a method of updating an avatar in accordance with one or more embodiments of the present invention.

FIG. 17 shows a flowchart depicting example processing that may be performed by the training system 100 while a user is executing a training module in some embodiments. At block 1702 a training module is initialized. For example, the user 126 may use an input device of the training station 102 to select one of the training modules 1310 thereby causing execution of the selected training module on the training station 102 (or on the server 104, for example, where the selected training module is provided remotely over the network 118). At block 1704 biometric monitoring is initialized. For example, block 1704 may cause the process of FIG. 10 (or similar) to be initiated. After block 1704, one or more of blocks 1706, 1708, 1710, 1712, 1714, 1716, 1718 may be executed to determine one or more of the derived biometric states 1340. In particular, at block 1706, a gender of the user may be determined. For example, a gender of the user may be determined based on the electronic facial recognition data 200*d*. At block 1708 an age of the user may be determined, again, for example based on the electronic facial recognition data 200*d*. At block 1710 a stress level of the user may be determined based, for example, on one or more of the electronic heart rate data 200*g*, the electronic respiratory rate data 200*e*, the electronic skin conductance data 200*a*, the electronic blood glucose data 200*b* and the electronic blood pressure data 200*c*. At block 1712 an emotion of the user may be determined based, for example, on the electronic facial recognition data 200*d*. At blocks 1714, 1716 and 1718 a level of interest, engagement and excitement of the user, respectively, may be determined based, for example on the electronic neural data 200*f* and/or the electronic facial recognition data 200*d*. Where the derived biometric states 1340 are determined by another entity in the training system 100 (e.g. the server 104 during the processing of FIG. 10), the processing at blocks 1706-1718 may include obtaining the derived biometric states 1340 from the appropriate entity. Whether or not a particular one of blocks 1706 to 1718 is processed may be based upon a number of factors, such as, requirements of the particular training module that has been initialized and which biometric data 200 has been received.

At block 1720 an avatar (such as the avatar 1502, and/or a simulation avatar) may be updated based upon one or more of the determined gender, age, stress level, emotion, interest, engagement and excitement determined at blocks 1706 to 1718 or indeed based upon any of the biometric data 1330, 1340. Updating the avatar at block 1720 may include determining and applying one or more graphical update operations to be applied to the avatar based upon the biometric data 1330, 1340. For example, updating the avatar at block 1720 may include determining a current state of the avatar, determining a desired state of the avatar, and determining one or more graphical operations to transition the avatar from the current state to the desired state.

At block 1722 a determination may be made as to whether the avatar requires updating. For example, a determination may be made as to whether a predetermined length of time has elapsed since a last update to the avatar. A determination may be made as to whether new biometric data has been received since a last update of the avatar. A determination may be made as to whether any received biometric data differs from biometric data that was last used to update the avatar at step 1720. Other criteria that may be used for determining whether an update to the avatar is required will be readily apparent to the skilled person. If it is determined that an update to the avatar is required, one or more of blocks 1706 to 1718 may again be processed. If it is determined that an update is not required, a determination may be made at block 1724 as to whether the training module has ended. If it is determined that the training module has not ended, processing may loop between blocks 1722 and 1724 until it is determined that an update to the avatar is required or the training module has ended.

In some embodiments, the virtual simulation itself may be updated in response to processing of the biometrics obtained from the user 126. For example, one or more training virtual simulations may include one or more possible "paths". Paths may be selected in dependence upon a user's biometric response to events that are presented to the user in the virtual simulation. For example, where if it is determined, during a training session, that a user is doing well at a particular task (e.g. regulate breathing, control stress levels, etc.), a path may be taken that will challenge that user (e.g. the selected path may present more challenging events than other possible paths). Similarly, if it is determined that a particular simulation is not adequately stimulating or maintaining the attention of a user (e.g. based upon the determined levels of interest, excitement, engagement, alertness, emotion, etc.), paths may be selected through a virtual reality simulation to encourage a desired response. For example, paths may be selected that are expected to increase alertness. By improving user alertness/engagement, for example, the training provided by the training system may be more effective at causing skills and lessons to be internalized by users.

In some embodiments, where multiple users undertake training using the training system 100, scores obtained by each user during training sessions may be recorded and used to provide scoreboards to enable ranking of the users. Scoreboards may be provided to the first users (i.e. those undertaking training), and such scoreboards may serve to improve motivation and therefore efficacy of the training provided through the training system 100. Scoreboards may be provided to second users and may serve as a way to monitor training across a plurality of first users to determine, for example, where to focus future training. Rankings may also be beneficial for employers seeking to rank employees, candidate employees, etc. Multiple users may participate in training simultaneously (or substantially simultaneously having regard to, for example, network latency). For example, multiple first users may undertake training simultaneously, and/or a first user may undertake training while a second user oversees, guides or manages the training. Where a virtual reality simulation is provided, the multiple users may be represented in the virtual reality simultaneously such that the avatar of one user can interact with the avatar of one or more other users.

In some embodiments, machine learning is used to determine a set of desirable biometric responses to one or more of the training modules and/or virtual reality simulations of training modules. For example, one or more individuals may be selected to provide benchmarks. For example, individuals considered to be effective managers may be selected to provide benchmarks for a management training module. The selected individuals may use the training stations to undertake training and their biometrics may be measured and stored. Users undertaking training may then compare their own biometrics to those of the selected individuals. Additionally, the stored biometrics of the selected individuals may be used to form a training set for a neural network, for example. Such a trained neural network may then be operable to automatically analyze the biometrics of users. It will be appreciated that neural networks are provided only as an example of machine learning techniques that may be utilized with the training systems and techniques described herein.

While particular exemplary arrangements of the training stations 102, 103, and other entities of the training system 100 are described above, it is to be understood that the training stations 102, 103, and the other entities of the training system 100 may be implemented in any appropriate manner. For example, the user computer 130 (and the computers 105, 106, 110 112) may include personal computers (PC) as is known in the art. The user computer 122 may include a smartphone, a tablet computer, etc., as is known in the art. Each of the entities of the training system 100 may utilize any operating system compatible with the networked systems discussed herein. For example, the computers described herein may run UNIX, Linux, Windows®, OS X®, Android®, iOS®, etc. In the depicted exemplary embodiments, the training station 102 includes a generally stationary computer 130, while the training station 102 includes a mobile (or portable) computer 122. It will be appreciated, however, that this is merely one possible arrangement. For example, the training station 102 may include a "laptop" computer which may be stationary for the duration of a training session, but which is or may be re-located between training sessions.

Further, it is to be understood that while embodiments of a training system 100 have been described herein as including a network of entities, this is merely one exemplary embodiment. In some embodiments, a training system may be provided, for example, by a single device, or by two devices connected in a peer-to-peer arrangement. For example, in some embodiments, a training station (such as the training stations 102, 103) may be directly connected to a trainer computer (such as the trainer computer 105). In such an embodiment, processing that is described above as being performed by the server 104 may, for example, be performed by the user computer and/or by the trainer computer 105. By way of further example, while the datastore 108 is depicted in FIG. 1 as connected to a file server 106, it will be understood that the datastore 108 may be local to one or more of the other entities within the training system 100. For example, the datastore 108 may be local to the server 104 or the training station 102.

More generally, in the drawings and specification, there have been disclosed typical embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

As used throughout this application, the word "may" is used in a permissive sense (i.e., meaning having the potential to), rather than the mandatory sense (i.e., meaning must). The words "include", "including", and "includes" mean including, but not limited to. As used throughout this application, the singular forms "a", "an" and "the" include plural referents unless the content clearly indicates otherwise. Thus, for example, reference to "an element" may include a combination of two or more elements. Unless specifically stated otherwise, as apparent from the discussion, it is appreciated that throughout this specification discussions utilizing terms such as "processing", "computing", "calculating", "determining" or the like refer to actions or processes of a specific apparatus, such as a special purpose computer or a similar special purpose electronic processing/computer. In the context of this specification, a special purpose computer or a similar special purpose electronic processing/computer is capable of manipulating or transforming signals, typically represented as physical electronic or magnetic quantities within memories, registers, or other information storage devices, transmission devices, or display devices of the special purpose computer or similar special purpose electronic processing/computer.

The techniques described herein may include or otherwise be used in conjunction with techniques described in U.S. patent application Ser. No. 13/540,300 filed on Jul. 2, 2012 and titled "SYSTEMS, COMPUTER MEDIUM AND COMPUTER-IMPLEMENTED METHODS FOR MONITORING HEALTH OF EMPLOYEES USING MOBILE DEVICES", U.S. patent application Ser. No. 13/540,153 filed on Jul. 2, 2012 and titled "SYSTEMS AND METHOD TO MONITOR HEALTH OF EMPLOYEE WHEN POSITIONED IN ASSOCIATION WITH A WORKSTATION", U.S. patent application Ser. No. 13/540,028 filed on Jul. 2, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. patent application Ser. No. 13/540,067 filed on Jul. 2, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,095 filed on Jul. 2, 2012 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,124 filed on Jul. 2, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. patent application Ser. No. 13/540,180 filed on Jul. 2, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. patent application Ser. No. 13/540,208 filed on Jul. 2, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. patent application Ser. No. 13/540,335 filed on Jul. 2, 2012 and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", U.S. patent application Ser. No. 13/540,374 filed on Jul. 2, 2012 and titled "SYSTEMS, COMPUTER MEDIUM AND COMPUTER-IMPLEMENTED METHODS FOR MONITORING HEALTH AND ERGONOMIC STATUS OF DRIVERS OF VEHICLES" (now U.S. Pat. No. 8,872,640), and/or U.S. patent application Ser. No. 13/540,262 filed on Jul. 2, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", the disclosures of which are incorporated herein by reference in their entireties.

In this patent, certain U.S. patents, U.S. patent applications, or other materials (e.g., articles) have been incorporated by reference. The text of such U.S. patents, U.S. patent applications, and other materials is, however, only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference in this patent.

That claimed is:

1. A training system comprising:
   one or more processors;
   one or more input and output units in communication with the one or more processors;
   one or more heart rate sensors in communication with the one or more input and output units;
   one or more respiratory rate sensors in communication with the one or more input and output units;
   one or more skin conductance sensors in communication with the one or more input and output units;
   one or more blood glucose sensors in communication with the one or more input and output units;
   one or more blood pressure sensors in communication with the one or more input and output units;
   one or more neural sensors in communication with the one or more input and output units;
   one or more facial recognition sensors in communication with the one or more input and output units and positioned to capture images of physical facial features;
   one or more displays in communication with the one or more processors; and
   one or more non-transitory processor-readable media in communication with the one or more processors, the one or more non-transitory processor-readable media having processor-readable instructions stored therein that when executed cause the training system to perform the steps of:
   providing a virtual reality training session;
   obtaining biometric data from a first user during the virtual reality training session, the obtaining comprising the steps of:
      converting measurements from the one or more heart rate sensors into electronic heart rate data,
      converting respiratory rate measurements from the one or more respiratory rate sensors into electronic respiratory rate data,
      converting skin conductance measurements from the one or more skin conductance sensors into electronic skin conductance data,
      converting blood glucose measurements from the one or more blood glucose sensors into electronic blood glucose data,
      converting blood pressure measurements from the one or more blood pressure sensors into electronic blood pressure data,
      converting neural signals measured by the one or more neural sensors into electronic neural data,
      converting physical facial features captured by the one or more facial recognition sensors into electronic facial data indicative of one or more of: gender, age, and emotion of the first user,
      determining a stress level of the first user responsive to analysis of at least the electronic heart rate data, the electronic respiratory rate data, the electronic skin conductance data, the electronic blood glucose data, and the electronic blood pressure data, and
      determining a level of interest, a level of engagement, a level of alertness, and a level of excitement responsive to analysis of at least the electronic neural data and the electronic facial data;
   displaying, in real time on the one or more displays, a first indication of one or more of the electronic heart rate data, the electronic respiratory data, the electronic skin conductance data, the electronic blood glucose data, the electronic blood pressure data, the electronic neural data, the electronic facial data, the determined stress level, and the determined levels of interest, engagement, alertness, and excitement;
   determining, based on the biometric data obtained, avatar images indicative biometric states of the first user at different points in time during the virtual reality training session; and
   displaying a post-training review comprising display of an animation of the avatar images that provides a visual representation of development of the biometric state of the first user during the virtual reality training session.

2. The system of claim 1, wherein the displaying step comprises display of the first indication within a virtual reality interface associated with the virtual reality training session.

3. The system of claim 2, wherein the virtual reality interface is configured to include an avatar representing the first user, and wherein display of the first indication comprises determination of one or more graphical operation based upon at least a portion of the obtained biometric data and application of the one or more graphical operation to the avatar representing the first user.

4. The system of claim 3, wherein the non-transitory processor-readable media has processor-readable instructions stored therein that when executed cause the training system to monitor one or more of the one or more heart rate sensors, the one or more respiratory rate sensors, the one or more skin conductance sensors, the one or more blood glucose sensors, the one or more blood pressure sensors, the one or more neural sensors and the one or more facial recognition sensors for changes in the obtained biometric data; and determine one or more further graphical operation responsive to determination of a change in the obtained biometric data and apply the one or more further graphical operation to the displayed avatar.

5. The system of claim 1, wherein the non-transitory processor-readable media has processor-readable instructions stored therein that when executed cause the training system to provide a second indication of one or more of the electronic heart rate data, the electronic respiratory data, the electronic skin conductance data, the electronic blood glucose data, the electronic blood pressure data, the electronic neural data, the electronic facial data, the determined stress level, and the determined levels of interest, engagement, alertness, and excitement to a second user.

6. The system of claim 5, wherein providing the second indication to a second user comprises provision of at least the second indication to the second user in real-time during the virtual reality training session.

7. The system of claim 5, wherein the non-transitory processor-readable media has processor-readable instructions stored therein that when executed cause the training system to store at least a portion of the obtained biometric data; and wherein providing the second indication to the second user comprises transmission of the stored at least a portion of the obtained biometric data to the second user for review.

8. The system of claim 1, wherein the non-transitory processor-readable media has processor-readable instructions stored therein that when executed cause the training system to generate one or more alerts responsive to obtaining the biometric data.

9. The system of claim 8, wherein providing an indication of obtained biometric data to a user comprises provision of the one or more alerts to the user.

10. The system of claim 1, wherein the non-transitory processor-readable medium has processor-readable instructions stored therein that when executed cause the system to monitor the obtained biometric data in real-time to determine whether one or more biometric boundary conditions are exceeded.

11. The system of claim 10, wherein the non-transitory processor-readable media has processor-readable instructions stored therein that when executed cause the training system to generate one or more alerts responsive to obtaining the biometric data and wherein generating one or more alerts is responsive to determination that one or more biometric boundary conditions are exceeded.

12. The system of claim 1, wherein providing the virtual reality training session comprises:

receiving a selection of a training module from one of a plurality of training modules; and determining biometric data required by the selected training module;

wherein the step of obtaining biometric data is responsive to the determination of the biometric data required by the selected training module.

13. The system of claim 1, wherein a virtual reality simulation of the virtual reality training session comprises a plurality of paths, and the method further comprises selecting one or more of the plurality of paths responsive to the obtained biometric data.

14. A method of providing training in a training system, the method comprising:

obtaining biometric data from a first user during a virtual reality training session, the obtaining comprising:

converting measurements from one or more heart rate sensors into electronic heart rate data, converting respiratory rate measurements from one or more respiratory rate sensors into electronic respiratory rate data, converting skin conductance measurements from one or more skin conductance sensors into electronic skin conductance data, converting blood glucose measurements from one or more blood glucose sensors into electronic blood glucose data, converting blood pressure measurements from one or more blood pressure sensors into electronic blood pressure data, converting neural signals measured by one or more neural sensors into electronic neural data, converting physical facial features captured by one or more facial recognition sensors into electronic facial data indicative of one or more of: gender, age, and emotion of the first user, determining a stress level of the first user responsive to analysis of at least the electronic heart rate data, the electronic respiratory rate data, the electronic skin conductance data, the electronic blood glucose data, and the electronic blood pressure data, and determining a level of interest, a level of engagement, a level of alertness, and a level of excitement responsive to analysis of at least the electronic neural data and the electronic facial data; and displaying, in real time on the one or more displays, a first indication of one or more of the electronic heart rate data, the electronic respiratory data, the electronic skin conductance data, the electronic blood glucose data, the electronic blood pressure data, the electronic neural data, the electronic facial data, the determined stress level, and the determined levels of interest, engagement, alertness, and excitement;

determining, based on the biometric data obtained, avatar images indicative biometric states of the first user at different points in time during the virtual reality training session; and displaying a post-training review comprising display of an animation of the avatar images that provides a visual representation of development of the biometric state of the first user during the virtual reality training session.

15. The method of claim 14, further comprising the step of displaying an avatar representing the first user within a virtual reality interface associated with the virtual reality training session, determination of one or more graphical operation based upon at least a portion of the obtained biometric data and application of the one or more graphical operation to the displayed avatar.

16. The method of claim 15, further comprising the steps of:

monitoring one or more of the one or more heart rate sensors, the one or more respiratory rate sensors, the one or more skin conductance sensors, the one or more blood glucose sensors, the one or more blood pressure sensors, the one or more neural sensors and the one or more facial recognition sensors for a change in the obtained biometric data; and determination of one or more further graphical operation responsive to determination of a change in the obtained biometric data and application of the one or more further graphical operation to the displayed avatar.

17. The method of claim 14, further comprising the step of providing a second indication of one or more of the electronic heart rate data, the electronic respiratory data, the electronic skin conductance data, the electronic blood glucose data, the electronic blood pressure data, the electronic neural data, the electronic facial data, the determined stress level, and the determined levels of interest, engagement, alertness, and excitement to a second user.

18. The method of claim 14, further comprising a real-time determination of whether the obtained biometric data indicates that one or more biometric boundary conditions are exceeded; and generation of one or more alerts responsive to a determination that one or more biometric boundary conditions are exceeded.

19. The method of claim 18, wherein the step of providing an indication of obtained biometric data to a user comprises providing one or more of the one or more alerts to the user.

20. A non-transitory computer readable medium comprising program instructions stored thereon that are executable by one or more processors to cause the following operations for providing training in a training system:

obtaining biometric data from a first user during a virtual reality training session, the obtaining comprising:

converting measurements from one or more heart rate sensors into electronic heart rate data, converting respiratory rate measurements from one or more respiratory rate sensors into electronic respiratory rate data, converting skin conductance measurements from one or more skin conductance sensors into electronic skin conductance data, converting blood glucose measurements from one or more blood glucose sensors into electronic blood glucose data, converting blood pressure measurements from one or more blood pressure sensors into electronic blood pressure data, converting neural signals measured by one or more neural sensors into electronic neural data, converting physical facial features captured by one or more facial recognition sensors into electronic facial data indicative of one or more of: gender, age, and emotion of the first user, determining a stress level of the first user responsive to analysis of at least the electronic heart rate data, the electronic respiratory rate data, the electronic skin conductance data, the electronic blood glucose data, and the electronic blood pressure data, and determining a level of interest, a level of engagement, a level of alertness, and a level of excitement responsive to analysis of at least the electronic neural data and the electronic facial data;

displaying, in real time on the one or more displays, a first indication of one or more of the electronic heart rate data, the electronic respiratory data, the electronic skin conductance data, the electronic blood glucose data, the electronic blood pressure data, the electronic neural data, the electronic facial data, the determined stress level, and the determined levels of interest, engagement, alertness, and excitement, determining, based on the biometric data obtained, avatar images indicative biometric states of the first user at different points in time during the virtual reality training session; and displaying a post-training review comprising display of an animation of the avatar images that provides a visual representation of development of the biometric state of the first user during the virtual reality training session.

* * * * *